United States Patent [19]
Poovaiah et al.

[11] Patent Number: 6,077,991
[45] Date of Patent: Jun. 20, 2000

[54] COMPOSITIONS AND METHODS FOR PRODUCTION OF MALE-STERILE PLANTS

[75] Inventors: Bachettira W. Poovaiah; Zhihua Liu, both of Pullman, Wash.; Shameekumar Patil, Lincoln, Nebr.; Daisuke Takezawa, Sapporo, Japan

[73] Assignee: Washington State University Research Foundation, Pullman, Wash.

[21] Appl. No.: 08/655,352

[22] Filed: May 23, 1996

Related U.S. Application Data

[60] Provisional application No. 60/014,743, Mar. 28, 1996.
[51] Int. Cl.$^7$ .............................. A01H 5/00; A01H 1/02; C12N 15/29; C12N 15/82
[52] U.S. Cl. .......................... 800/278; 800/286; 800/298; 800/303; 435/69.1; 435/194; 435/320.1; 435/419; 435/468; 536/23.6; 536/24.5
[58] Field of Search ................................. 536/23.6, 24.5; 435/69.1, 172.3, 194, 320.1, 419, 468; 800/205, 278, 286, 298, 303; 47/58, DIG. 1

[56] References Cited

PUBLICATIONS

Ames et al, "Amino–terminal myristoylation induces cooperative calcium binding to recoverin," *J. Biol. Chem.*, 270:4526–4533, 1995.
Botella et al, "Differential expression of two calmodulin genes in response to physical and chemical stimuli," *Plant Mol. Biol.*, 24:757–766, 1994.
Braam et al, "Rain–, wind–, and touch–induced expression of calmodulin and calmodulin–related genes in Arabidopsis," *Cell*, 60:357–364, 1990.
Brickey et al, "Mutational analysis of the autoinhibitory domain of calmodulin kinase II," *J. Biol. Chem.*, 269:29047–29054, 1994.
Bush, "Regulation of cytosolic calcium in plants," *Plant Physiol.*, 103:7–13, 1993.
Cohen, "Signal integration at the level of protein kinases, protein phospatases and their substrates," *TIBS*, 17:408–413, 1992.
Colbran et al, "Calcium/calmodulin–dependent protein kinase II," *Biochem. J.*, 258:313–325, 1989.
Colbran et al, "Calcium/calmodulin–dependent protein kinase II," *Curr. Top. Cell. Reg.*, 31:181–221, 1990.
Colbran, "Inactivation of $Ca^{2+}$/calmodulin–dependent protein kinase II by basal autophosphorylation," *J. Biol. Chem.*, 268:7163–7170, 1993.
Enslen et al, "Characterization of $Ca^{2+}$/calmodulin–dependent protein kinase IV," *J. Biol. Chem.*, 269:15520–15527, 1994.
Fong et al, "Studies of the regulatory mechanism of Ca2+/calmodulin–dependent protein kinase II," *J. Biol. Chem.*, 264:16759–16763, 1989.
Fujisawa, "Calmodulin–dependent protein kinase II," *BioEssays*, 12:27–29, 1990.
Gilroy et al, "Calcium homeostasis in plants," *J. Cell Sci.*, 106:453–462, 1993.
Gilroy et al, "A decade of plant signals," *BioEssays*, 16:677–682, 1994.
Goldberg et al, "Anther development: Basic principles and practical applications," *Plant Cell*, 5:1217–1229, 1993.
Hanks et al, "The protein kinase family: Conserved features and deduced phylogeny of the catalytic domains," *Science*, 241:42–52, 1988.
Hanson et al, "Neuronal $Ca^{2+}$/calmodulin–dependent protein kinases," *Annu. Rev. Biochem*, 61:559–601, 1992.
Harper et al, "A calcium–dependent protein kinases with a regulatory domain similar to calmodulin," *Science*, 252:951–252, 1991.
Hernould et al, "Male–sterility induction in transgenic tobacco plants with an unedited atp9 mitochondrial gene from wheat," *Proc. Natl. Acad. Sci.*, 90:2370–2374, 1993.
Hunter, "A thousand and one protein kinases," *Cell*, 50:823–829, 1987.
James et al, "Calmodulin–binding domains: just two faced or multi–faceted?", *TIBS*, 20:38–42, 1995.
Jena et al., "Molecular cloning and sequencing of a cDNA for plant calmodulin: Signal–induced changes in the expression of calmodulin," *Proc. Natl. Acad. Sci.*, 86:3644–3648, 1989.
Kameshita et al, "Autophosphorylation of calmodulin–dependent protein kinase IV from rat cerebral cortex," *J. Biochem.*, 113:583–590, 1993.
Kim et al, "Molecular cloning and characterization of anther–preferential cDNA encoding a putative actin–depolymerizing factor," *Plant Mol. Biol.*, 21:39–45, 1993.
Klee "Concerted regulation of protein phosphorylation and dephosphorylation by calmodulin," *Neurochem. Res.*, 16:1059–1065, 1991.
Kobayashi et al, "Molecular cloning of hippocalcin, a novel calcium–binding protein of the recoverin family exclusively expressed in hippocampus," *Biochem. and Biophys. Res. Comm.*, 189:511–517, 1992.
Kornstein et al, "Cloning and sequence determination of a cDNA encoding *Aspergillus nidulans* calmodulin–dependent multifunctional protein kinase," *Gene*, 113:75–82, 1992.
Kuno et al, "cDNA cloning of a neural visinin–like $Ca^{2+}$–binding protein," *Biochem. Biophys. Res. Comm.*, 184:1219–1225, 1992.
Lenz et al, "VILIP, a cognate protein of the retinal calcium binding proteins visinin and recoverin, is expressed in the developing chicken brain," *Mol. Brain Res.*, 15:133–140, 1992.

(List continued on next page.)

*Primary Examiner*—David T. Fox
*Attorney, Agent, or Firm*—Klarquist Sparkman Campbell Leigh & Whinston, LLP

[57] ABSTRACT

The present invention provides plant calcium/calmodulin-dependent protein kinase (CCaMK) nucleic acids, polypeptides, antibodies, and related methods. CCaMK genes are expressed in anthers in a developmental stage-specific manner. Suppression of CCaMK expression, e.g., by an antisense transgene, results in male-sterility.

16 Claims, 26 Drawing Sheets

OTHER PUBLICATIONS

Lickteig et al, "Regulation of $Ca^{2+}$/calmodulin–dependent protein kinase II by $Ca^{2+}$/calmodulin–independent authophosphorylation," *J. Biol. Chem.*, 263:19232–19239, 1988.

Ling et al, "Primary structures of Arabidopsis calmodulin isoforms deduced from the sequences of cDNA clones," *Plant Physiol.*, 96:1196–1202, 1991.

Mariani et al, "Induction of male sterility in plants by a chimaeric ribonuclease gene," *Nature*, 347:737–741, 1990.

Mayford et al, "CaMKII regulates the frequency–response function of hippocampal synapses for the production of both LTD and LTP," *Cell*, 81:891–904, 1995.

McCormick, "Male gametophyte development," *Plant Cell*, 5:1265–1275, 1993.

Mochizuki et al, "Purification and characterization of $Ca^{2+}$/calmodulin–dependent protein kinase V from rat cerebrum," *J. Biol. Chem.*, 268:9143–9147, 1993.

Moffat, "High–tech plants promise a bumper crop of new products," *Science*, 256:770–771, 1992.

Moncrief et al, "Evolution of EF–hand calcium–modulated proteins. I. Relationships based on amino acid sequences," *J. Mol. Evol.*, 30:522–562, 1990.

Nairn et al, "Calcium/calmodulin–dependent protein kinases," *Semin. Cancer Biol.*, 5:295–303, 1994.

Okazaki et al, "Full sequence of neurocalcin, a novel calcium–binding protein abundant in central nervous system," *Biochem. Biophys. Res. Comm.*, 185:147–153, 1992.

O'Neil et al, "How calmoduin binds its targets: Sequence independent recognition of amphophilic α–helices," *TIBS*, 15:59–64, 1990.

Palczewski et al, "Molecular cloning and characterization of retinal photoreceptor guanylyl cyclase–activating protein," *Neuron*, 13:395–404, 1994.

Patil et al, "Chimeric plant calcium/calmodulin–dependent protein kinase gene with a neural visinin–like calcium–binding domain," *Proc. Natl. Acad. Sci.*, 92:4897–4901, 1995.

Pausch et al, "Multiple $Ca^{2+}$/calmodulin–dependent protein kinase genes in a unicellular eukaryote," *EMBO J.*, 10:1511–1522, 1991.

Perera et al, "Structure and expression of the Arabidopsis CaM–3 calmodulin gene," *Plant Mol. Biol.*, 19:649–664, 1992.

Perera et al, Synthesis and accumulation of calmodulin in suspension cultures of carrot (*Daucus carota* L.), *Plant Physiol.*, 100:812–819, 1992.

Poovaiah et al, "Calcium messenger system in plants," *Crit. Rev. Plant Sci.*, 6:47–103, 1987.

Poovaiah et al, "Calcium and signal transduction in plants," *Crit. Rev. Plant Sci.*, 12:185–211, 1993.

Takezawa et al, "Calcium–dependent protein kinase genes in corn roots," *J. Plant Physiol*, 149:329–335, 1996.

Poovaiah et al, "Regulated expression of a calmodulin isoform alters growth and development in potato," *J. Plant Physiol.*, 149:553–558, 1996.

Pongs et al, "Frequenin—a novel calcium–binding protein that modulates synaptic efficacy in the Drosophila nervous systems" *Neuron*, 11:15–28, 1993.

Roberts et al, "Calcium–modulated proteins: Targets of intracellular calcium signals in higher plants," *Annu. Rev. Plant Physiol. Plant Mol. Biol.*, 43:375–414, 1992.

Schulman "The multifunctional $Ca^{2+}$/calmodulin–dependent protein kinase," *Adv. in Second Messenger and Phosphoprotein Res.*, 22:39–111, 1988.

Schulman "The multifuntional $Ca^{2+}$/calmodulin–dependent protein kinase," *Curr. Opin. Cell Biol.*, 5:247–253, 1993.

Sikela "Screening and expression library with a ligand probe: Isolation and sequence of a cDNA corresponding to a brain calmodulin–binding protein," *Proc. Natl. Acad. Sci.*, 84:3038–3042, 1987.

Spena et al, "Anther–specific expression of the rolB gene of *Agrobacterium rhizogenes* increases IAA content in anthers and alters anther development and whole flower growth," *Theor. Appl. Genet.*, 84:520–527, 1992.

Stone et al, "Plant protein kinase families and signal transduction," *Plant Physiol*, 108:451–457, 1995.

Takezawa et al, "Calmodulin gene family in potato: developmental and touch–induced expression of the mRNA encoding a novel isoform," *Plant Mol. Biol.*, 27:693–703, 1995.

Takezawa et al, "Dual regulation of a chimeric plant serine/threonine kinase by calcium and calcium/calmodulin," *J. Biol. Chem.*, 271:8126–8132, 1994.

Thiel et al, "$Ca^{2+}$/calmodulin–dependent protein kinase II: Identification of threonine–286 as the autophosphorylation site in the α subunit associated with the generation of $Ca^{2+}$–independent activity," *Proc. Natl. Acad. Sci.*, 85:6337–6341, 1988.

Tokui et al, "Autophosphorylation of smooth muscle myosin light chain kinase at its regulatory domain," *Biochemistry*, 34:5173–5179, 1995.

Tsuchiya et al, "Tapetum–specific expression of the gene for an endo–β–1, 3–glucanase causes male sterility in transgenic tobacco," *Plant Cell Physiol.*, 36:487–494, 1995.

van der Meer et al, "Antisense inhibition of flavonoid biosynthesis in petunia anthers results in male sterility," *Plant Cell*, 4:253–262, 1992.

Veluthambi et al, "Calcium–promoted protein phosphorylation in plants," *Science*, 223:167–169, 1984.

Wang et al, "A potato cDNA encoding a homologue of mammalian multidrug resistant P–glycoprotein," *Plant Mol. Biol.*, 31:683–687, 1996.

Wang et al, "A novel kinesin–like protein with a calmodulin–binding domain," *Plant Mol. Biol.*, 31:87–100, 1996.

Watillon et al, "A calcium/calmodulin–binding serine/threonine protein kinase homologous to the mammalian type II calcium/calmodulin–dependent protein kinase is expressed in plant cells," *Plant Physiol.* 101:1381–1384, 1993.

Worrall et al, "Premature dissolution of the microsporocyte callose wall causes male sterility in transgenic tobacco," *Plant Cell*, 4:759–771, 1992.

Harper, et al., "Calcium and Lipid Regulation of an Arabidopsis Protein Kinase Expressed in *Escherichia Coli*," *Biochemistry*, 32:3282–3290, 1993.

Peacock, Jim., "Ways to Pollen Sterility," *Nature*, 347:714–715, 1990.

Lee et al. Biochemistry 37: 6801–6809, 1998.

Lewin, R. 1987. Science 237:1570.

Reeck et al. 1987. Cell 50:667.

Poovaiah et al. 1991. Progress in Plant Growth Regulation. Karssen et al., eds.; Dordrecht, The Netherlands: Kluwer Academic Publishers, pp. 691–702.

FIG. 1A

```
                              GCTGGCTTTATTCCTCTGCTACCAATTTAGTATA    34
ATACCTCTCCCCATCCATCATCATCTTGACGTCCCTAGCTCCCCATTTTTTCTTTTTTA        94
AAATCCGTGAGTCAATTTCTTGTTTTCATACTCCCCACATTCACACCAACCCCTATCCAA      154
CCCCTTACTCCCCATTCCAAAATCTGAGTTCTTCTCAGATTCTTGATAAGAGTAAAGGTT      214
GTCCAGAATTGATATTTTCTTCAATACCATATTCCAGTTTCTGGATTACTTGATTCCAAT      274
ATTAAGCTTGATTGATGATATGAGCAAAGGGGTTGTCTGTAATTAAGCTTAAGCTTGTCT      334
TCAATACCCATATTTCAGTTTCTGGATTTCTGTCGGAATTTTCGTATCAGGATTCCGATA      394
TTGACCTTGATTCTTGATTCAAGCAAAAGGTAGTCCGGATTGCTGGATTCCAATATTGAC      454
CTTGATTCTTGATCAAGCAAAGGGTTGTTCGGTGTACTGGCAAAGGATTGTCAGGATTAC      514
TGCTCCGAATTTCACACACATTTGGGTAAATTACAGTAGAAGGTACTGAGTCCTTGAAAT      574
TGAATGTTGTTCTCTTGAAAGTGGGATTGTGAGTTGGAGGTGGCATTTAACCCAGGCTTG      634
ATGTCGAGGCATGAGAGCAGAAAGCTCTCGGATGATTATGAAGTGGTTGATGTTCTTGGA      694
 M  S  R  H  E  S  R  K  L  S  D  D  Y  E  V  V  D  V  L  G     (20)

AAAGGCGGATTCTCGGTTGTAAGGAGAGGAATCAGCAAATCAAGAGGGAAGAACAATGAT      754
 K  G  G  F  S  V  V  R  R  G  I  S  K  S  R  G  K  N  N  D     (40)

GTTGCTATCAAGACCTTGAGAAGATACGGGTACACGCTTCCGGGGGCGCAGCGGAGCCAA      814
 V  A  I  K  T  L  R  R  Y  G  Y  T  L  P  G  A  Q  R  S  Q     (60)

CCTGGGCAGAGGGGGTTGTCTCCTTTAGGAATGCCCACACTGAAGCAAGTTTCTGTTTCG      874
 P  G  Q  R  G  L  S  P  L  G  M  P  T  L  K  Q  V  S  V  S     (80)

GATGCGTTGCTCACGAATGAAATTCTGGTCATGAGGAGAATAGTGGAGGATGTTTCTCCT      934
 D  A  L  L  T  N  E  I  L  V  M  R  R  I  V  E  D  V  S  P    (100)

CACCCTAATGTGATCCACCTGCATGATGTGTATGAAGATGCAAATGGAGTTCATCTTGTG      994
 H  P  N  V  I  H  L  H  D  V  Y  E  D  A  N  G  V  H  L  V    (120)

CTGGAGCTTTGCTCTGGCGGGGAGTTGTTTGATCGGATAGTTGCGCAGGATCGGTATTCG     1054
 L  E  L  C  S  G  G  E  L  F  D  R  I  V  A  Q  D  R  Y  S    (140)

GAATCAGAGGCGGCTGAAGTGGTCCAGCAGATAGCGAGTGGGTTAGCTGCACTTCATAAA     1114
 E  S  E  A  A  E  V  V  Q  Q  I  A  S  G  L  A  A  L  H  K    (160)

TCCACTATCATTCATCGCGATTTGAAGCCAGAGAATTGTTTGTTTCTGAATCAAGAGAAA     1174
 S  T  I  I  H  R  D  L  K  P  E  N  C  L  F  L  N  Q  E  K    (180)

CGTTCTACTCTGAAAATAATGGACTTTGGTCTAAGTTCTGTGGAAGATTTTACTGATCCT     1234
 R  S  T  L  K  I  M  D  F  G  L  S  S  V  E  D  F  T  D  P    (200)

ATAGTTGCTCTGTTTGGTTCGATTGATTATGTTTCTCCTGAAGCTTTGTCTCAGCGTCAA     1294
 I  V  A  L  F  G  S  I  D  Y  V  S  P  E  A  L  S  Q  R  Q    (220)

GTTAGCTCAGCTAGCGACATGTGGTCTCTTGGGGTGATATTGTATATCCTTCTCTCCGGA     1354
 V  S  S  A  S  D  M  W  S  L  G  V  I  L  Y  I  L  L  S  G    (240)

TGCCCACCTTTTCATGCACCATCAAATCGGGAAAAGCAGCAGCGGATACTGGCAGGTGAT     1414
 C  P  P  F  H  A  P  S  N  R  E  K  Q  Q  R  I  L  A  G  D    (260)

TTCAGCTTTGAGGAGCACACGTGGAAGACCATAACTTCATCAGCAAAGGATTTGATTTCC     1474
 F  S  F  E  E  H  T  W  K  T  I  T  S  S  A  K  D  L  I  S    (280)

AGTCTTTTGTCTGTTGATCCTTACAAAAGACCAACTGCTAATGATCTTTTGAAGCATCCT     1534
 S  L  L  S  V  D  P  Y  K  R  P  T  A  N  D  L  L  K  H  P    (300)

TGGGTGATAGGGGACTCTGCCAAACAGGAACTAATTGAACCAGAGGTTGTTTCTAGACTG     1594
 W  V  I  G  D  S  A  K  Q  E  L  I  E  P  E  V  V  S  R  L    (320)
```

FIG. 1B

```
         *
CGAAGTTTCAATGCTCGGCGGAAATTACGTGCAGCTGCAATAGCCAGTGTTTTGAGTAGC   1654
 R   S   F   N   A   R   R   K   L   R   A   A   A   I   A   S   V   L   S   S      (340)

AAAGTTTTGTTGAGAACAAAGAAACTGAAGAATTTGCTTGGATCCCATGATATGAAATCG   1714
 K   V   L   L   R   T   K   K   L   K   N   L   L   G   S   H   D   M   K   S       (360)

GAGGAACTTGAAAATCTCCGAGCTCACTTTAAGAGAATATGTGCAAATGGAGACAATGCG   1774
 E   E   L   E   N   L   R   A   H   F   K   R   I   C   A   N   G   D   N   A       (380)

ACACTACCGGAGTTCGAGGAAGTTCTTAAAGCGATGAAAATGAATTCTCTAATCCCTCTT   1834
 T   L   P   E   F   E   E   V   L   K   A   M   K   M   N   S   L   I   P   L       (400)
                                         I *
GCGCCTCGGGTATTTGACCTATTTGACAACAACCGTGATGGAACTATAGACATGAGAGAG   1894
 A   P   R   V   F   D   L   F   D   N   N   R   D   G   T   I   D   M   R   E       (420)

ATATTATGTGGGTTGTCGAATCTTAGGAACTCACAAGGCGATGATGCTCTCCAGCTCTGT   1954
 I   L   C   G   L   S   N   L   R   N   S   Q   G   D   D   A   L   Q   L   C       (440)
                    II
TTTCAGATGTATGATGCCGACAGGTCTGGATGTATCAGCAAGGAGGAATTAGCATCAATG   2014
 F   Q   M   Y   D   A   D   R   S   G   C   I   S   K   E   E   L   A   S   M       (460)

CTTAGGGCCTTGCCCGAGGATTGTGTTCCTGCCGATATAACAGAGCCAGGAAAGTTGGAC   2074
 L   R   A   L   P   E   D   C   V   P   A   D   I   T   E   P   G   K   L   D       (480)
                            III
GAGATCTTTGATCAGATGGACGCCAACAGTGATGGAGTTGTCACGTTCGACGAGTTCAAA   2134
 E   I   F   D   Q   M   D   A   N   S   D   G   V   V   T   F   D   E   F   K       (500)

GCCGCTATGCAAAGAGACAGCTCCCTGCAAGACGTGGTTCTATCTTCGCTGCGAACGATA   2194
 A   A   M   Q   R   D   S   S   L   Q   D   V   V   L   S   S   L   R   T   I       (520)

TAGTCCTCTCTGGTCCTTCCCTTACGAATCAGTGGTGTGCAGGTCACAGATCGTAGGGTG   2254
    *
GAATAACAATCAATATTTTAGCTTCTATCATAAATCATCTGAGAGGTGTAAAACATTATG   2314
TACAGTATAGAGAACAAGCATGTGTTTATGATCTGTCATATGAAATCGATGTCTCAGTGA   2374
CTCATAACCTTTGTCACGAAATGTATCAGAGAGAACTTTCCCAATTTAGGCTATTGTAGT   2434
TCTATCGACTTTTGTATCTAACTAAATGAATCATCTAAGCCTGTCCTTGATGTGTAAGGG   2494
ATTATGTGCTTACAGTTTCT   2514
```

FIG. 2

```
              1                                                    51
LLyck1   VLLRTKKLK.....NLLGSHDMKSEELENLRAHFKRICANGDNATIPEFEE
Rahc1    MGKQNSKLRPEMLQDLRENTEFSELELQEWYKGFLKDCPTG.ILNVDEFKK
Rav13    MGKQNSKLRPEVLQDLREHTEFTDHELQEWYKGFLKDCPTG.HLTVDEFKK
Bov11    MGKQNSKLRPEVMQDLLESIDFTEHEIQEWYKGFLRDCPSG.HLSMEEFKK
Rav11    MGKQNSKLAPEVMEDLVKSTEFNEHELKQWYKGFLKDCPSG.RLNLEEFQQ
Chv11    MGKQNSKLAPEVMEDLVKSTEFNEHELKQWYKGFLKDCPSG.RLNLEEFQQ
Rav12    MGKNNSKLAPEELEDLVQNTEFSEQELKQWYKGFLKDCPSG.ILNLEEFQQ
Drfr1    MGKKSSKLKQDTIDRLTTDTYFTEKEIRQWHKGFLKDCPNG.LITEQGFIK I
         52             *                                         102
Lyck1    V.LKAMKMNSLIPLAPRVFDLFDNNRDGTIDMREILCGLSNLRNSQG..DD
Rahc1    IYANFFPYGDASKFAEHVFRTFDINSDGTIDFREFIIALSVT..SRGRLEQ
Rav13    IYANFFPYGDASKFAEHVFRTFDINSDGTIDFREFIIALSVT..SRGKLEQ
Bov11    IYGNFFPYGDASKFAEHVFRTFDANGDGTIDFREFIIALSVT..SRGKLEQ
Rav11    LYVKFFPYGDASKFAQHAFRTFDKNGDGTIDFREFICALSIT..SRGSFEQ
Chv11    LYVKFFPYGDASKFAQHAFRTFDKNGDGTIDFREFICALSIT..SRGSFEQ
Rav12    LYIKFFPYGDASKFAQHAFRTFDKNGDGTIDFREFICALSVT..SRGSFEQ
Drfr1    IYKQFFPQGDPSKFASLVFRVFDENNDGSIEFEEFIRALSVT..SKGNLDE II
         103                                                      153
Lyck1    ALQLCFQMYDADRSGCISKEELASMLRA...........LPEDCVPADIT
Rahc1    KLMWAFSMYDLDGNGYISREEMLEIVQAIYKMVSSV..MKMPED....EST
Rav13    KLKWAFSMYDLDGNGYISRSEMLEIVQAIYKMVSSV..MKMPED....EST
Bov11    KLKWAFSMYDLDGNGYISKAEMLEIVQAIYKMVSSV..MKMPED....EST
Rav11    KLNWAFNMYDLDGDGKITRVEMLEIIEAIYKMVGTVIMMKMNED....GLT
Chv11    KLNWAFNMYDLDGDGKITRVEMLEIIEAIYKMVGTVIMMKMNED....GLT
Rav12    KLNWAFEMYDLDGDGRITRLEMLEIIEAIYKMVGTVIMMRMNQD....GLT
Drfr1    KLQWAFRLYDVDNDGYITREEMYNIVDAIYQMVG...QQPQSED....ENT III
         154                                                      204
Lyck1    EPGK.LDEIFDQMDANSDGVVTFDEFKAAMQRDSS....LQDVVLSSIRTI
Rahc1    .PEKRTEKIFRQMDINNDGKLSLEEFIRGAKSDPSIVRLLQCDP.SSASQF
Rav13    .PEKRTDKIFRQMDINNDGKLSLEEFIKGAKSDPSIVRLLQCDP.SSASQF
Bov11    .PEKRTEKIFRQMDINRDGKLSLEEFIRGAKSDPSIVRLLQCDP.SSAGQF
Rav11    .PEQRVDKIFSKMDKNKDDQITLDEFKEAAKSDPSIVLLLQCDI.....QK
Chv11    .PEQRVDKIFSKMDKNKDDQITLDEFKEAAKSDPSIVLLLQCDI.....QK
Rav12    .PQQRVDKIFKKMDQDKDDQITLEEFKEAAKSDPSIVLLLQCDM.....QK
Drfr1    .PQKRVDKIFDQMDKNHDGKLTLEEFREGSKADPRIVQAL.......SLGGG
```

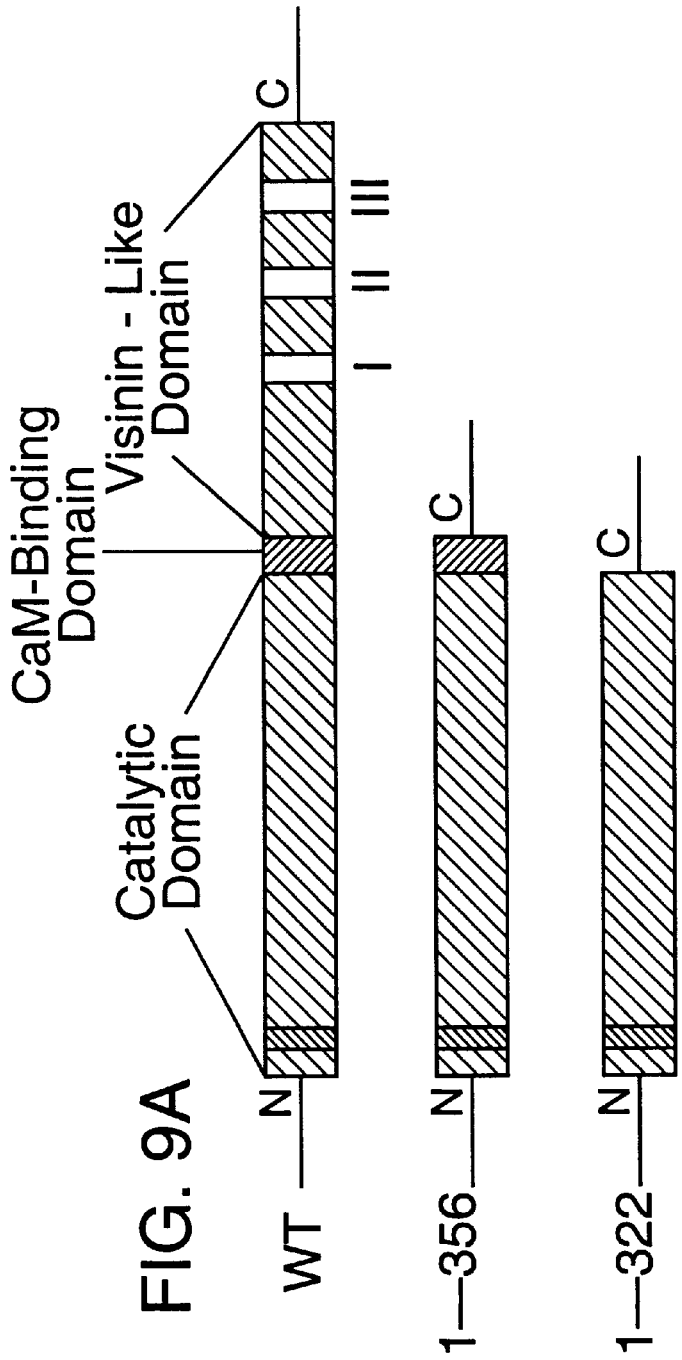

FIG. 11
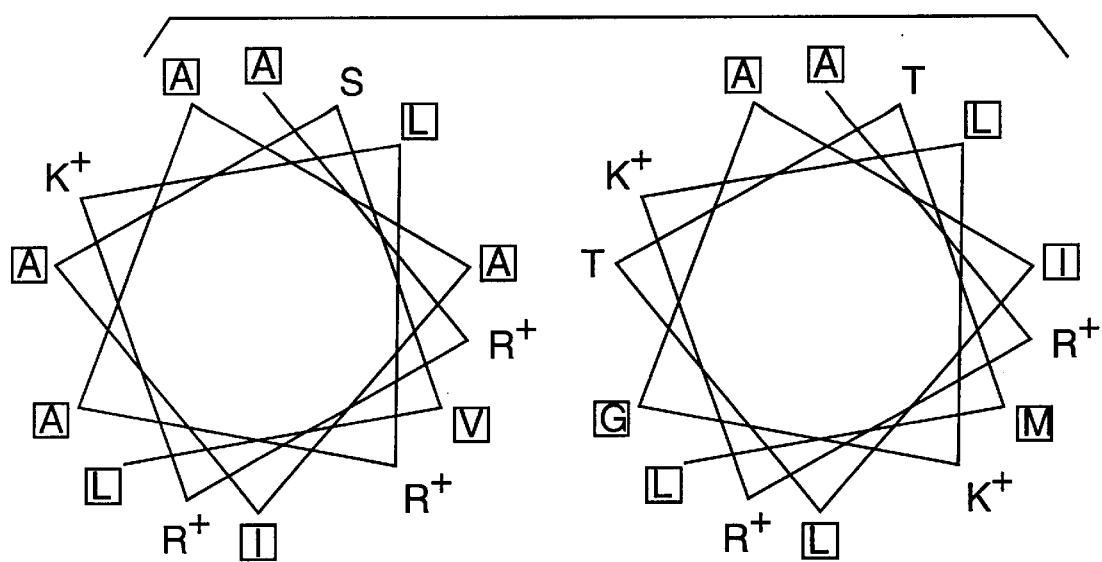
FIG. 12
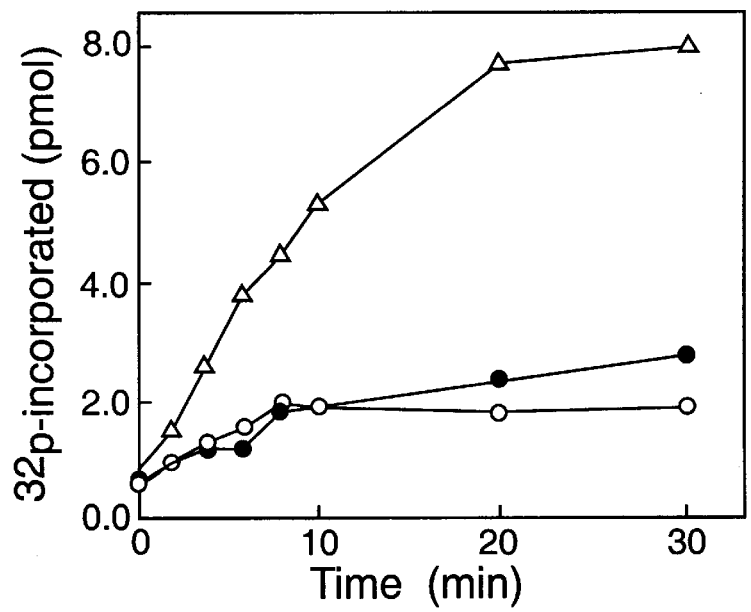
FIG. 14A
```
           x     y     z    -y     -x         -z
    I      D  N  N  R  D  G  T  I  D  M    R  E
    II     D  A  D  R  S  G  C  I  S  K    E  E
    III    D  A  N  S  D  G  V  V  T  F    D  E
                                     ↓
                                     A
```

```
             KLRAAAIASVLSS    1
       SFNARRKLRAAAIASVLSS    2
    VSRLRSFNARRKLRAAAIASVLSS  3
LIEPEVVSRLRSFNARRKLRAAAIASVLSS 4
```

CaM-binding domain

FIG. 22

```
TAATTAACCTTTCTCTCTCATGGGACAAAGGGAAGATGGAAAAACTCTAAGTGATGAATA
                 M  G  Q  R  E  D  G  K  T  L  S  D  E  Y
TGAAGTGACAGATATACTTGGAAGAGGAGGGTTTTCAGTAGTGAGGAGAGGAACAAGAAG
 E  V  T  D  I  L  G  R  G  G  F  S  V  V  R  R  G  T  R  R
AAGAACACTACATTCGGGTCAACATCATGAAGTTGTTGCCATTAAAACCCTCCGGCGGTT
 R  T  L  H  S  G  Q  H  H  E  V  V  A  I  K  T  L  R  R  F
CGGGCCACCACCGGCGCCGGAGAAGAAGTCTCTTAATAAATCTCGAGTACCACAGGCGGC
 G  P  P  P  A  P  E  K  K  S  L  N  K  S  R  V  P  Q  A  A
TTTGATATCCGAAACTCTACTGACGAACGAGCTGTTAGTCATGATTAAGATCGTCGAAGA
 L  I  S  E  T  L  L  T  N  E  L  L  V  M  I  K  I  V  E  D
TGTTTCTCCTCATCCTAACGTCATTCATCTCTACGACGTTTGTGAGGATCCTTCTGGAGT
 V  S  P  H  P  N  V  I  H  L  Y  D  V  C  E  D  P  S  G  V
TCATCTCATTTTGGAGCTTTGCTCTGGTGGTGAGCTCTTTGATCGGATTGCTGGGCAAGC
 H  L  I  L  E  L  C  S  G  G  E  L  F  D  R  I  A  G  Q  A
AAGGTATAATGAGGCTGGGGCTGCTGCTGTGGTGAGACAGATAGCTAAGGGGCTAGAGGC
 R  Y  N  E  A  G  A  A  A  V  V  R  Q  I  A  K  G  L  E  A
GCTACACGGGGCAAGTATAGTTCACAGGGACTTGAAACCAGAGAACTGTCTATTCTTGAA
 L  H  G  A  S  I  V  H  R  D  L  K  P  E  N  C  L  F  L  N
CAAGGATGAGAATTCACCGTTGAAGATTATGGATTTTGGGCTGAGTTCTATTGAGGATTT
 K  D  E  N  S  P  L  K  I  M  D  F  G  L  S  S  I  E  D  F
TGCAAATCCAGTGGTTGGTTTGTTTGGTTCCATAGATTATGTATCACCAGAAGCACTTTC
 A  N  P  V  V  G  L  F  G  S  I  D  Y  V  S  P  E  A  L  S
AAGGGAAAATATCACCACTAAAAGTGATATTTGGTCACTTGGTGTTATCCTTTACATTCT
 R  E  N  I  T  T  K  S  D  I  W  S  L  G  V  I  L  Y  I  L
CCTCTCTGGGTACCCACCTTTCATCGCGCCGTCCAATCGAAAAAAGCAACAAATGATATT
 L  S  G  Y  P  P  F  I  A  P  S  N  R  K  K  Q  Q  M  I  L
AAATGGGCAGTTCAGTTTTGATGAGAAAACCTGGAAAAACATATCTTCATCGGCAAAACA
 N  G  Q  F  S  F  D  E  K  T  W  K  N  I  S  S  A  K  Q
ACTAATTTCCAGTCTCTTGAAAGTTGATCCTAACATGAGGCCTACTGCTCAAGAGATACT
 L  I  S  S  L  L  K  V  D  P  N  M  R  P  T  A  Q  E  I  L
TGAACATCCATGGGTGACAGGAGATTTGGCAAAGCAAGAACAGATGGACGCCGAGATTGT
 E  H  P  W  V  T  G  D  L  A  K  Q  E  Q  M  D  A  E  I  V
TTCCCGTCTCCAAAGCTTCAACTCTCGGCGCAAGTTCAGGGCAGCAGCTATGGCCAGTGT
 S  R  L  Q  S  F  N  S  R  R  K  F  R  A  A  A  M  A  S  V
CTTGAGCAGCAGCTTTTCCTTGCGAACTAAGAAATTGAAGAAATTGGTTGGTTCATATGA
 L  S  S  S  F  S  L  R  T  K  K  L  K  K  L  V  G  S  Y  D
CTTGAAGCCTGAAGAATTACAAAACCTTAGCCACAATTTCAAGAAAATATGCAAAAATGG
 L  K  P  E  E  L  Q  N  L  S  H  N  F  K  K  I  C  K  N  G
AGAAAATTCAACTTTACTGGAATTCGAAGAGGTCCTCAAAGCTATGGAAATGTCATCTTT
 E  N  S  T  L  L  E  F  E  E  V  L  K  A  M  E  M  S  S  L
AGTGCCTTTAGCTCCCAGAATATTTGATCTATTTGACAATAACCGTGATGGAACAGTAGA
 V  P  L  A  P  R  I  F  D  L  F  D  N  N  R  D  G  T  V  D
CATGAGAGAAATAATTGGTGGCTTCTCAAGCCTCAAGTATTCCCAAGGGGATGACGCACT
 M  R  E  I  I  G  G  F  S  S  L  K  Y  S  Q  G  D  D  A  L
TCGTCTTTGTTTCCAGATGTATGATACAGATCGATCAGGCTGCATTAGCAAGGAAGAAGT
 R  L  C  F  Q  M  Y  D  T  D  R  S  G  C  I  S  K  E  E  V
TGCGTCCATGTTGAGAGCACTTCCTGAAGACTGCCTTCCAATTAATATAACAGAACCAGG
 A  S  M  L  R  A  L  P  E  D  C  L  P  I  N  I  T  E  P  G
AAAACTTGACGAGATATTTGATTTAATGGATGCAAACAGTGATGGTAAAGTTACTTTTGA
 K  L  D  E  I  F  D  L  M  D  A  N  S  D  G  K  V  T  F  D
TGAGTTCAAAGCTGCTATGCAAAGAGATAGTTCCCTTCAAGATGTAGTCCTCTCTTTCT
 E  F  K  A  A  M  Q  R  D  S  S  L  Q  D  V  V  L  S  S  L
TCGTCCCTCTTAATTAATTCCTTTATTGAATTTTTGCCTCTTTTAATTTGTAATAACACG
 R  P  S  *
CTAATTCTATTAATATCTCTAACTTTCTATGACAATGCATTTATTATTTTTATCACTACT
CGTAAAAAGATCCTTTAAATTAATTCGGAAGCCTTTATGGTAAAAAAAAAAAAAAAAAAA
AAAAAAAAAAAAAAAAAAAAAAAAAAAAAAAAAAAAA
```

FIG. 23A

```
Tobacco  MGQREDGKTL SDEYEVTDIL GRGGFSVVRR GTRRTLHSG.  40
Lily     MSRHESRKL  SDDYEVVDVL GKGGFSVVRR GISK...SR   35
                 II         I Tobacco  QHHEVVAIKT LRRFG..... PPPAPEKKS LNKSRVP..Q   72
Lily     GKNNDVAIKT LRRYGYTLPG AQRSQPGQRG LSPLGMPTLK  75
                            III Tobacco  AALISETLLT NELVMIKIV EDVSPHPNVI HLYDVCEDPS  112
Lily     QVSVSDALLT NEILVMRRIV EDVSPHPNVI HLHDVYEDAN  115
              V                      IV Tobacco  GVHLILELCS GGELFDRIAG QARYNEAGAA AVVRQIAKGL  152
Lily     GVHLVLELCS GGELFDRIVA QDRYSESEAA EVVQQIASGL  155
                              VI Tobacco  EALHGASIVH RDLKPENCLF LNKDENSPLK IMDFGLSSIE  192
Lily     AALHKSTIIH RDLKPENCLF LNQEKRSTLK IMDFGLSSVE  195
                           VIII                VII Tobacco  DFANPVGLF GSIDYVSPEA LSRENITTKS DIWSLGVILY  232
Lily     DFTDPIVALF GSIDYVSPEA LSQRQVSSAS DMWSLGVILY  235
                                    X         IX Tobacco  ILLSGYPPFH APSNRKKQQM ILNGQFSFDE KTWKNISSA  272
Lily     ILLSGCPPFH APSNREKQQR ILAGDFSFEE HTWKTITSSA  275
             XI Tobacco  KQLISSLLKV DPNMRPTAQE ILEHPWVTGD LAKQEMDAE   312
Lily     KDLISSLLSV DPYKRPTAND LLKHPWVIGD SAKQELIEPE  315
```

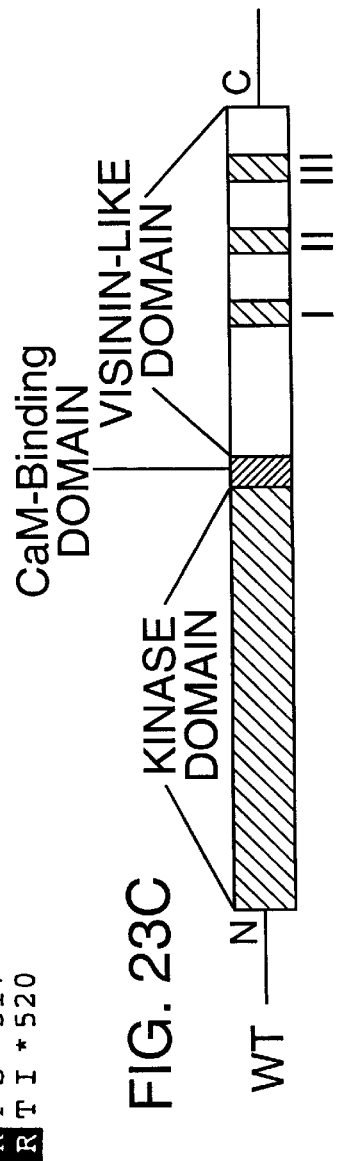

FIG. 26

```
   1  GTCGACCTTC TGCGTTGTTT GGTTTGTAGG AGCACCGGGA GGAACTGGAC
  51  CTCGCCTAGT TGCTTTATTG GAAGTACCCG ATATCGCCTG TTTCAGTTCT
 101  GTCATTACCG TATCCTGTCG TGTGAGATGG CCTAGAATGG ACTCTTATTG
 151  CGCTTGCAGG ACCCTTACCG CTTCGACGAC GTGCTCCTCT TCAGCATCCT
 201  TGGGAGTCAC TTCTCGAACA TGTCGGGGGT ATCGCCTTCC ATGGACCGGT
 251  GTGGCCTCAT TTCCCCCGCT GCGGGTATCG CTGATCAAAT CCTCATTCTG
 301  AGGTTAATTT CCTTGGGACT CAAGGTTTTA TGTGTTGTTA ACATCATTAT
 351  CTGCCATTTT CTATGATTTT TTGCTTAGAA CAAATAATCA AACACGTTAG
 401  AAAGAGACAA GGACCAACTT AATCACACAA CTATCTAAGC CACACGATGG
 451  GCGCCAAACT GTTTACCCGT AAAACGGTAC AATTAAATAT ATGTGGTTTA
 501  TAGACAAGTG AATTAATTTA ATCCTAAAAT AATAGAAGAA TTAGATAAAA
 551  ATGTAATATT TAGCCTTGAG ATTGAGATGA AATAGTAGAA ATAGTAATTC
 601  CGGGAGCAAG ACTTCCGGGC ACAACGACAA TGATATCAAA GGACAAGAAG
 651  ATAAAATTAT ATTAAACTTT GAATAGAGTG TAATGTATGT TGCTAGAAAA
 701  ATTCATGTCC TTCACAATGA TAATAGAGCT CACTATTTAT AGCTCCACCT
 751  AAGGAAAGAT CCTAGGATCA AGCCCCTCTT TAATGTCAAT TATGAGGGCC
 801  ATTGAAGAAT TTGTAACGTG GCAGTGAATG CCATATTTCT TGTAACGGAC
 851  ATATACTTAA TGTTGTAGAA TATTCTTCAT TAGATGCTAC TGGATGACAA
 901  ACATTTATTT TATCTTTATG AGTATCATTC TCTTCGGTAA CGGACGGGAT
 951  CGTTGCCTTT GGTTTCAACT ATCTTATGTC TTCGGCCACA CATATCATTT
1001  CCTCGTGCGA TCATTTAATA TAACATATTT TAGCCTATAC AATATTATTT
1051  TATCTAATTT TTCACGGATA ACATCTTGTA TTTTCTTTAA TTCAAGTTAA
1101  CTTTTAATCA GCTAGATGAT AGAGATTATC ATTTTATTCA TGGAAAGCTT
1151  GTTATTCATA AGTTATAAAA TAGCTTATAT AGCAAATCTT TACTTGTGAT
1201  TTAGTATATA TATGAACTAA AGACTACAAA GAAATCTTGT GAGCCCCTCG
1251  CTAAAGAGGA TGATGATGGA GGAAACGAGT ACACTTGATC GATTATGAAA
1301  GAAACCATCC TTAAAAAAC  CAAATTAAGA CCAAACAGTA AAGGTAAATT
1351  ATGCGTAGAA AGCAAGAAAT TTGTACTTGC CTATCTACAT GATTGGAGGC
1401  ATCTTATAAT AATCTTATTG AGAGAGATGC ATCTCAAGAA CAAAGAGAAT
1451  TAACATAATT AATCTGAAAG AAGATTAGTT TGACTAAGTC AATTGTATAT
1501  TATTATTAGC CTTCTTCCCC TTTGTTGCCA TTTGCTTATA TTTCATGGCC
1551  CACACCAACC CGCCCGGCCA ACAAAATTA  TAAATTAAAA ACCCTTTTAA
1601  AACTCATGAT CATCAGTTTG ATGATGTAAC TACGTGTATA CCCACCTCAA
1651  TAATACTGTA CCTCATTTCC TTATTAATTC CATCCTAATA TTCGTCAAAC
1701  ACAATTAACC TTTCTCTCTC ATG
```

COMPOSITIONS AND METHODS FOR PRODUCTION OF MALE-STERILE PLANTS

CROSS REFERENCE TO RELATED CASES

This application claims the benefit of U.S. provisional application No. 60/014,743, filed Mar. 28, 1996, incorporated herein by reference.

ACKNOWLEDGMENT OF GOVERNMENT SUPPORT

This invention was made with government support under National Science Foundation grant number DCB 91-4586. The government has certain rights in this invention.

TECHNICAL FIELD

This invention relates to plant calcium/calmodulin-dependent protein kinases, particularly anther-specific calcium/calmodulin-dependent protein kinases.

BACKGROUND OF THE INVENTION

Calcium and calmodulin regulate diverse cellular processes in plants (Poovaiah and Reddy, *CRC Crit. Rev. Plant Sci.* 6:47–103, 1987, and *CRC Crit. Rev. Plant Sci.* 12:185–211, 1993; Roberts and Harmon, *Annu. Rev. Plant Physiol. Plant Mol. Biold.* 43:375–414, 1992; Gilroy and Trewavas, *BioEssays* 16:677–682, 1994). Transient changes in intracellular $Ca^{2+}$ concentration can affect a number of physiological processes through the action of calmodulin (CaM), a ubiquitous $Ca^{2+}$-binding protein. $Ca^{2+}$/calmodulin-regulated protein phosphorylation plays a pivotal role in amplifying and diversifying the action of $Ca^{2+}$-mediated signals (Veluthambi and Poovaiah, *Science* 223:167–169, 1984; Schulman, *Curr. Opin. in Cell. Biol.* 5:247–253, 1993). Extracellular and intracellular signals regulate the activity of protein kinases, either directly or through second messengers. These protein kinases in turn regulate the activity of their substrates by phosphorylation (Cohen, *Trends Biochem. Sci.* 17:408–413, 1992; Stone and Walker, *Plant Physiol.* 108:451–457, 1995).

In animals, $Ca^{2+}$/calmodulin-dependent protein kinases play a pivotal role in cellular regulation (Colbran and Soderling, *Current Topics in Cell. Reg.* 31:181–221, 1990; Hanson and Schulman, *Annu. Rev. Biochem.* 61:559–601, 1992; Mayford et al., *Cell* 81:891–904, 1995). Several types of CaM-dependent protein kinases (CaM kinases, phosphorylase kinase, and myosin light chain kinase) have been well characterized in mammalian systems (Fujisawa, *BioEssays* 12:27–29, 1990; Colbran and Soderling, *Current Topics in Cell. Reg.* 31:181–221, 1990; Klee, *Neurochem. Res.* 16:1059–1065, 1991; Mochizuki et al., *J. Biol. Chem.* 268:9143–9147, 1993).

Although little is known about $Ca^{2+}$/calmodulin-dependent protein kinases in plants (Poovaiah et al., in *Progress in Plant Growth Regulation*, Karssen et al., eds., Dordrecht, The Netherlands: Kluwer Academic Publishers, 1992, pp. 691–702; Watillon et al., *Plant Physiol.* 101:1381–1384, 1993), $Ca^{2+}$-dependent, calmodulin-independent protein kinases (CDPKs) have been identified (Harper et al., *Science* 252:951–954, 1991; Roberts and Harmon, *Annu. Rev. Plant Physiol. Plant Mol. Biol.* 43:375–414, 1992).

Male gametophyte formation in the anther is a complex developmental process involving many cellular events. During microsporogenesis, microsporocytes undergo meiosis to form tetrads of microspores that are surrounded by a callose wall composed of $\beta$-1,3-glucan. The callose wall is subsequently degraded by callase, which is secreted by cells of the tapetum (Steiglitz, *Dev. Biol.* 57:87–97, 1977), a specialized anther tissue that produces a number of proteins and other substrates that aid in pollen development or become a component of the pollen outer wall (Paciani et al., *Plant Syst. Evol.* 149:155–185, 1985; Bedinger, *Plant Cell* 4:879–887, 1992; Mariani et al., *Nature* 347:737–741, 1990). The timing of callase secretion is critical for microspore development. Male sterility has been shown to result from premature or delayed appearance of callase (Worral et al., *Plant Cell* 4:759–771, 1992; Tsuchiya et al., *Plant Cell Physiol.* 36:487–494, 1995).

Induction of male sterility in plants can provide significant cost savings in hybrid plant production, enable production of hybrid plants where such production was previously difficult or impossible, and allow the production of plants with reduced pollen formation to reduced the tendency of such plants to elicit allergic reactions or to extend the life of flowers that senesce upon pollination (e.g., orchids).

Several strategies have been developed for the production of male-sterile plants (Goldberg et al., *Plant Cell* 5:1217–1229, 1993), including: selective destruction of the tapetum by fusing the ribonuclease gene to a tapetum-specific promoter, TA29 (Mariani et al., *Nature* 347:737–741, 1990); premature dissolution of the callose wall in pollen tetrads by fusing glucanase gene to tapetum-specific A9 or Osg6B promoters (Worrall et al., *Plant Cell* 4:759–771, 1992; Tsuchiya et al., *Plant Cell Physiol.* 36:487–494, 1995); antisense inhibition of flavonoid biosynthesis within tapetal cells (Van der Meer et al., *Plant Cell* 4:253–262, 1992); tapetal-specific expression of the *Agrobacterium rhizogenes* rolB gene (Spena et al., *Theor. Appl. Genet.* 84:520–527, 1992); and overexpression of the mitochondrial gene atp9 (Hernould et al., *Proc. Natl. Acad. Sci. USA* 90:2370–2374, 1993).

SUMMARY OF THE INVENTION

Genes encoding plant calcium/calmodulin-dependent protein kinases (CCaMKs) have been cloned and sequenced. Expression of CCaMK genes is highly organ- and developmental stage-specific. When CCaMK antisense constructs were expressed in plants, the plants were rendered male-sterile. The availability of CCaMK cDNA and genomic DNA sequences makes possible the production of a wide variety of male-sterile plants, including monocotyledonous, dicotyledonous, and other plant varieties. CCaMK promoters are also useful for targeted expression of heterologous genes, as is described in greater detail below.

Accordingly, the present invention provides isolated nucleic acids based on the cloned CCaMK sequences. Nucleic acids that include at least 15 contiguous nucleotides of a native lily or tobacco CCaMK gene and hybridize specifically to a CCaMK sequence under stringent conditions are useful, for example, as CCaMK-specific probes and primers. CCaMK promoter sequences are useful for the expression of heterologous genes in anthers of transgenic plants in a developmental stage-specific manner.

Isolated CCaMK nucleic acids can be expressed in host cells to produce recombinant CCaMK polypeptide or fragments thereof, which in turn can be used, for example, to raise CCaMK-specific antibodies that are useful for CCaMK immunoassays, for purification of CCaMK polypeptides, and for screening expression libraries to obtain CCaMK homologs from other plant species. The native CCaMK sequence can be altered, e.g., by silent and conservative substitutions, to produce modified forms of CCaMK that preferably retain calcium/calmodulin-dependent protein kinase activity. Alternately, CCaMK polypeptides can be obtained from plant tissue by standard protein purification techniques, including the use of CCaMK-specific antibodies.

The foregoing and other objects and advantages of the invention will become more apparent from the following detailed description and accompanying drawings.

BRIEF DESCRIPTION OF THE DRAWINGS

FIG. 1 shows the nucleotide and deduced amino acid sequences of lily CCaMK. Diagnostic sequences (GKGGFS (amino acid residues 20–25 of SEQ ID NO:1) DLKPEN (amino acid residues 167–172 of SEQ ID NO:1) SIDYVSPE (amino acid residues 207–214 of SEQ ID NO:1)) for serine/threonine kinases are underlined. Sequences corresponding to two PCR primers (DLKPEN and FNARRKL) are indicated by arrows. The calmodulin-binding domain is double-underlined, $Ca^{2+}$-binding EF-hand motifs are boxed, the putative autophosphorylation sites (RXXS/T) are indicated by asterisks, and the hatched region indicates the putative biotin-binding site (LKAMKMNSLI, amino acid residues 389–398 of SEQ ID NO:1).

FIG. 2 shows a comparison of the deduced amino-acid sequence of the C-terminal region (amino acid residues 342–520 of SEQ ID NO:1) of lily CCaMK to neural visinin-like $Ca^{2+}$-binding proteins. Conserved amino acids are boxed; $Ca^{2+}$-binding domains (I–III) are indicated by solid lines; putative autophosphorylation site is indicated by an asterisk; and the putative biotin-binding site (B) is indicated by a hatched box. Abbreviations: Lyck1, lily CCaMK (SEQ ID NO:1) Rahc1, rat hippocalcin (Gen2:Ratp23K(SEQ ID NO:2)); Ravl3, rat neural visinin-like protein (Gen2:Ratnvp3(SEQ ID NO:3)); Bovl1, bovine neurocalcin (Gen1:Bovpcaln(SEQ ID NO:4)); Ravl1, rat neural visinin-like protein (Gen2:Ratnvp1(SEQ ID NO:5)); Chvl1, chicken visinin-like protein (Gen2:Ggvilip(SEQ ID NO:6)); Ravl2, rat neural visinin-like protein (Gen2:Ratnvp2(SEQ ID NO:7)); Drfr1, Drosophila frequenin (Gen2:Drofreq(SEQ ID NO:8)).

FIG. 9A shows the results of calmodulin binding assays using wild-type and truncated forms of lily CCaMK in order to determine the calmodulin binding site. Left: Schematic diagram of wild-type and truncation mutants of CCaMK used for $^{35}S$-calmodulin binding assays. Right: Autoradiograms showing calmodulin binding corresponding to the wild-type and mutant CCaMKs.

FIG. 9B shows a comparison of amino acid sequences surrounding the putative calmodulin-binding sites of lily CCaMK (amino acid residues 311–340 of ASEQ ID NO:1) and α subunit of mammalian calmodulin kinase II (CaMKII (SEQ ID NO:9)).

FIG. 11 shows a helical wheel projection of calmodulin-binding sequences in lily CCaMK (left) and animal CaMKIIα (right). Hydrophobic amino acid residues are boxed. Basic amino acid residues are marked with (+).

FIG. 12 shows a time course of autophosphorylation of lily CCaMK in the presence of 2.5 mM EGTA (●) or 0.5 mM $CaCl_2$ (Δ) or 0.5 mM $CaCl_2$ and 1 µM calmodulin (○). The autophosphorylation is presented as pmol $^{32}P$ incorporated per 21.4 pmol of CCaMK.

FIG. 14A shows amino acid sequences of the three EF-hand motifs in the visinin-like domain of lily CCaMK, DNNRDGTIDMRE, DADRSGCISKEE, and DANSDGVVTFDE (amino acid residues 409–420, 445–456, and 487–498, respectively, of SEQ ID NO:1). Six $Ca^{2+}$-ligating residues denoted as x, y, z, −y, −x, −z, respectively, are marked. Site-directed mutants were prepared by substituting the amino acid residues at the −x position with alanine (A).

FIG. 22 shows the nucleotide sequence and deduced amino-acid sequence of the tobacco CCaMK cDNA(SEQ ID NO:10).

FIG. 23A shows a comparison of deduced amino acid sequences of tobacco and lily CCaMKs(SEQ ID NO:1and SEQ ID NO:10, respectively). Eleven major conserved subdomains of serine/threonine protein kinases are marked. Hatched region indicates calmodulin-binding domain, the three $Ca^{2+}$-binding EF-hands are boxed.

FIG. 23B is a diagram showing the kinase domain, calmodulin-binding domain, and visinin-like $Ca^{2+}$-binding domain of the lily and tobacco CCaMK polypeptides. Three $Ca^{2+}$-binding sites within the visinin-like binding domain are indicated by Roman numerals I, II, and III.

FIG. 26 shows the nucleotide sequence of the promoter region of the tobacco CCaMK genomic clone(SEQ ID NO:11). The putative TATA box is underlined and the start codon is boxed.

FIG. 31A shows the results of slot-blot analysis demonstrating suppression of CCaMK mRNA in antisense plants (A3, A4, A14, and A17), wild-type plants (WT), and transgenic plants carrying vector alone (C). FIG. 31B shows calmodulin control (the same filter rehybridized with calmodulin).

Figure 3:
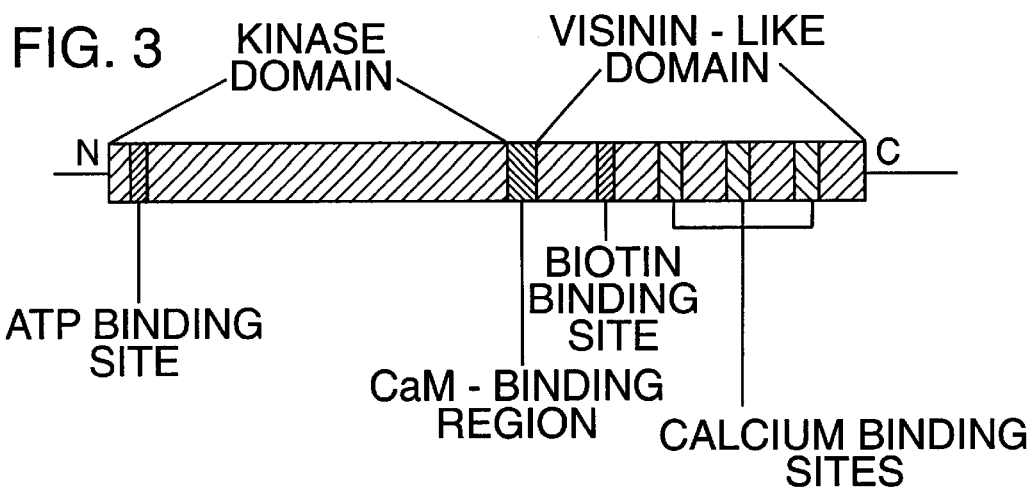
FIG. 3 is a schematic representation of structural features of the lily CCaMK polypeptide.

reporter gene. II. Transcriptional fusion of a truncated version of the tobacco CCaMK promoter to GUS. III. Translational fusion of the tobacco CCaMK promoter to the tobacco CCaMK coding region and GUS. IV. Transcriptional fusion of the CCaMK promoter to the tobacco CCaMK in an antisense orientation. V. Transcriptional fusion of the TA29 promoter to antisense tobacco CCaMK. VI. Transcriptional fusion of the cauliflower mosaic virus (CaMV) 35S promoter to antisense tobacco CCaMK. All constructs include the *Agrobacterium tumefaciens* nopaline synthase terminator sequence (Nos-ter).

DETAILED DESCRIPTION OF THE PREFERRED EMBODIMENTS

Definitions and Methods

The following definitions and methods are provided to better define the present invention and to guide those of ordinary skill in the art in the practice of the present invention. Definitions of common terms in molecular biology may also be found in Rieger et al., *Glossary of Genetics: Classical and Molecular,* 5th edition, Springer-Verlag: New York, 1991; and Lewin, Genes V, Oxford University Press: New York, 1994. The nomenclature for DNA bases as set forth at 37 CFR § 1.822 is used. The standard one- and three letter nomenclature for amino acid residues is used.

Nucleic Acids

"CCaMK Gene". The term "CCaMK gene" refers to a native CCaMK nucleic acid sequence or a fragment thereof, e.g., the native lily or tobacco CCaMK cDNA (SEQ ID NO:1 or SEQ ID NO:10, respectively) or genomic sequences and alleles and homologs thereof. The term also encompasses variant forms of a native CCaMK nucleic acid sequence or fragment thereof as discussed below, preferably a nucleic acid that encodes a polypeptide having CCaMK biological activity. Native CCaMK sequences include cDNA sequences and the corresponding genomic sequences (including flanking or internal sequences operably linked thereto, including regulatory elements and/or intron sequences).

"Native". The term "native" refers to a naturally-occurring ("wild-type") nucleic acid or polypeptide.

"Homolog". A "homolog" of a lily or tobacco CCaMK gene is a gene sequence encoding a CCaMK polypeptide isolated from an organism other than lily or tobacco.

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, Probes, and Primers. A fragment of a CCaMK nucleic acid is a portion of a CCaMK nucleic acid that is less than full-length and comprises at least a minimum length capable of hybridizing specifically with a native CCaMK nucleic acid under stringent hybridization conditions. The length of such a fragment is preferably at least 15 nucleotides, more preferably at least 20 nucleotides, and most preferably at least 30 nucleotides of a native CCaMK nucleic acid sequence.

Nucleic acid probes and primers can be prepared based on a native CCaMK gene sequence. A "probe" is an isolated DNA or RNA attached to a detectable label or reporter molecule, e.g., a radioactive isotope, ligand, chemiluminescent agent, or enzyme. "Primers" are isolated nucleic acids, generally DNA oligonucleotides 15 nucleotides or more in length, preferably 20 nucleotides or more, and more preferably 30 nucleotides or more, that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Methods for preparing and using probes and primers are described, for example, in *Molecular Cloning: A Laboratory Manual,* 2nd ed., vol. 1–3, ed. Sambrook et al., Cold Spring Harbor Laboratory Press, Cold Spring Harbor, New York, 1989 (hereinafter, "Sambrook et al., 1989"); Current Protocols in Molecular Biology, ed. Ausubel et al., Greene Publishing and Wiley-Interscience, New York, 1987 (with periodic updates) (hereinafter, "Ausubel et al., 1987"); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Substantial Similarity. A first nucleic acid is "substantially similar" to a second nucleic acid if, when optimally aligned (with appropriate nucleotide insertions or deletions) with the other nucleic acid (or its complementary strand), there is at least about 75% nucleotide sequence identity, preferably at least about 85% identity, and more preferably at least about 90% identity. Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

Operably Linked. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic-acid manipulation are well-known (see, e.g., Sambrook et al., 1989, and Ausubel et al., 1987). Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic acids; Vectors, Transformation, Host Cells Natural or synthetic nucleic acids according to the present invention can be incorporated into recombinant nucleic-acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, inter alia, in Sambrook et al., 1989, or Ausubel et al., 1987. A variety of well-known promoters or other sequences useful in constructing expression vectors are available for use in bacterial, yeast, mammalian, insect, amphibian, avian, or other host cells.

A cell, tissue, organ, or organism into which has been introduced a foreign nucleic acid, such as a recombinant vector, is considered "transformed", "transfected", or "transgenic." A "transgenic" or "transformed" cell or organism also includes (1) progeny of the cell or organism and (2) progeny produced from a breeding program employing such a "transgenic" plant as a parent in a cross and exhibiting an altered phenotype resulting from the presence of the recombinant CCaMK DNA construct.

Nucleic-Acid Hybridization; "Stringent Conditions", "Specific". The nucleic-acid probes and primers of the present invention hybridize under stringent conditions to a target DNA sequence, e.g., to a CCaMK gene.

The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product.

The term "specific for (a target sequence)" indicates that a probe or primer hybridizes under stringent conditions only to the target sequence in a sample comprising the target sequence.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990.

Methods of Obtaining Alleles and Homoloqs of Lily and Tobacco CCaMK. Based upon the availability of the lily CCaMK cDNA (SEQ ID NO:1) and tobacco CCaMK cDNA (SEQ ID NO:10) and genomic sequences (e.g., SEQ ID NO:11) disclosed herein, alleles and homologs can be readily obtained from a wide variety of plants by cloning methods known in the art, e.g., by screening a cDNA or genomic library with a probe that specifically hybridizes to a native CCaMK sequence under stringent conditions or by PCR or another amplification method using a primer or primers that specifically hybridize to a native CCaMK sequence under stringent conditions.

Cloning of a CCaMK Genomic Sequence. The availability of a CCaMK cDNA sequence enables the skilled artisan to obtain a genomic clone corresponding to the cDNA (including the promoter and other regulatory regions and intron sequences) and the determination of its nucleotide sequence by conventional methods. Both monocots and dicots possess CCaMK genes.

Primers and probes based on the native lily and tobacco CCaMK sequences disclosed herein can be used to confirm (and, if necessary, to correct) the CCaMK sequences by conventional methods.

Nucleotide-Sequence Variants of Native CCaMK Nucleic Acids and Amino Acid Sequence Variants of Native CCaMK Proteins. Using the nucleotide and the amino-acid sequence of the CCaMK polypeptides disclosed herein, those skilled in the art can create DNA molecules and polypeptides that have minor variations in their nucleotide or amino acid sequence.

"Variant" DNA molecules are DNA molecules containing minor changes in a native CCaMK sequence, i.e., changes in which one or more nucleotides of a native CCaMK sequence is deleted, added, and/or substituted, preferably while substantially maintaining a CCaMK biological activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in CCaMK biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native CCaMK sequence or a homolog thereof in which there has been a substitution of one or more base pairs but no change in the amino-acid sequence of the polypeptide encoded by the sequence. "Conservative" variants are variants of the native CCaMK sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed below. In addition, one or more codons encoding cysteine residues can be substituted for, resulting in a loss of a cysteine residue and affecting disulfide linkages in the CCaMK polypeptide.

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |

-continued

| Original Residue | Conservative Substitutions |
| --- | --- |
| Leu | ile, val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A CCaMK gene sequence can be modified as follows:

(1) To improve expression efficiency and redirect the targeting of the expressed poly-petide: For expression in non-plant hosts (or to direct the expressed polypeptide to a different intracellular compartment in a plant host), an appropriate transit or secretion peptide sequence can be added to the protein-coding region of the native gene sequence. In addition, one or more codons can be changed, for example, to conform the gene to the codon usage bias of the host cell or organism for improved expression. Enzymatic stability can be altered by removing or adding one or more cysteine residues, thus removing or adding one or more disulfide bonds.

(2) To alter substrate and ligand binding and CCaMK enzymatic activity: One or more amino acid residues in a substrate or ligand binding domain (e.g., the calmodulin-binding domain) can be mutagenized to affect the strength or specificity of the interaction between CCaMK and its polypeptide substrates or to affect control of CCaMK activity by $Ca^{2+}$ and/or calmodulin. The autoinhibitory domain can also be mutagenized or an autophosphorylation site removed or added to affect CCaMK activity. Further targets, including the visinin-like $Ca^{2+}$-binding domain or one or more EF-hand motifs thereof, can also be mutagenized.

Nucleic Acids Attached to a Solid Support. The nucleic acids of the present invention can be free in solution or covalently or noncovalently attached by conventional means to a solid support, such as a hybridization membrane (e.g., nitrocellulose or nylon), a bead, etc.

Polweptides

"CCaMK Protein". The term "CCaMK protein" (or polypeptide) refers to a protein encoded by a CCaMK nucleic acid, including alleles, homologs, and variants of a native CCaMK nucleic acid, for example. A CCaMK polypeptide can be produced by the expression of a recombinant CCaMK nucleic acid or be chemically synthesized. Techniques for chemical synthesis of polypeptides are described, for example, in Merrifield, *J. Amer. Chem. Soc.* 85:2149–2156, 1963.

Polypeptide Sequence Homology. Ordinarily, CCaMK polypeptides encompassed by the present invention are at least about 70% homologous to a native CCaMK polypeptide, preferably at least about 80% homologous, and more preferably at least about 95% homologous. Such homology is considered to be "substantial homology," although more important than shared amino-acid sequence homology can be the common possession of characteristic structural features and the retention of biological activity that is characteristic of CCaMK, preferably CCaMK catalytic activity.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated." "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. Various methods of protein purification are described, e.g., in *Guide to Protein Purification*, ed. Deutscher, *Meth. Enzymol.* 185, Academic Press, San Diego, 1990; and Scopes, Protein Purification: Principles and Practice, Springer Verlag, New York, 1982.

Variant and Modified Forms of CCaMK Polypeptides. Encompassed by the CCaMK polypeptides of the present invention are variant polypeptides in which there have been substitutions, deletions, insertions or other modifications of a native CCaMK polypeptide. The variants substantially retain structural characteristics and biological activities of a corresponding native CCaMK polypeptide and are preferably silent or conservative substitutions of one or a small number of contiguous amino acid residues.

A native CCaMK polypeptide sequence can be modified by conventional methods, e.g., by acetylation, carboxylation, phosphorylation, glycosylation, ubiquitination, and labeling, whether accomplished by in vivo or in vitro enzymatic treatment of a CCaMK polypeptide or by the synthesis of a CCaMK polypeptide using modified amino acids.

Labeling. There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel et al., 1987.

Polypeptide Fragments. The present invention also encompasses fragments of a CCaMK polypeptide that lacks at least one residue of a native full-length CCaMK polypeptide. Preferably, such a fragment retains $Ca^{2+}$/calmodulin-dependent kinase activity or possession of a characteristic functional domain (e.g., a calmodulin-binding domain, $Ca^{2+}$-binding EF-hand motif(s), autophosphorylation site(s), etc.), or an immunological determinant characteristic of a native CCaMK polypeptide (and thus able to elicit production of a CCaMK-specific antibody in a mouse or rabbit, for example or to compete with CCaMK for binding to CCaMK-specific antibodies) that is therefore useful in immunoassays for the presence of a CCaMK polypeptide in a biological sample. Such immunologically active fragments typically have a minimum size of 7 to 17 or more amino acids.

The terms "biological activity", "biologically active", "activity" and "active" refer primarily to the characteristic enzymatic activity or activities of a native CCaMK polypeptide, including, but not limited to, $Ca^{2+}$/calmodulin-dependent kinase activity.

Fusion Polypeptides. The present invention also provides fusion polypeptides including, for example, heterologous fusion polypeptides, i.e., a CCaMK polypeptide sequence or fragment thereof and a heterologous polypeptide sequence, e.g., a sequence from a different polypeptide. Such heterologous fusion polypeptides thus exhibit biological properties (such as substrate or ligand binding, enzymatic activity, antigenic determinants, etc.) derived from each of the fused sequences. Fusion partners include, for example, β-glucuronidase, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides are preferably made by the expression of recombinant nucleic acids produced by standard techniques.

Polypeptide Sequence Determination. The sequence of a polypeptide of the present invention can be determined by various methods known in the art. In order to determine the sequence of a polypeptide, the polypeptide is typically fragmented, the fragments separated, and the sequence of each fragment determined. To obtain fragments of a CCaMK polypeptide, the polypeptide can be digested with an enzyme such as trypsin, clostripain, or Staphylococcus protease, or with chemical agents such as cyanogen bromide, o-iodosobenzoate, hydroxylamine or 2-nitro-5-thiocyanobenzoate. Peptide fragments can be separated, e.g., by reversed-phase high-performance liquid chromatography (HPLC) and analyzed by gas-phase sequencing.

Polypeptide Coupling to a Solid Phase Support. The polypeptides of the present invention can be free in solution or coupled to a solid-phase support, e.g., nitrocellulose, nylon, column packing materials (e.g., Sepharose beads), magnetic beads, or glass wool, by conventional methods.

Antibodies

The present invention also encompasses polyclonal and/or monoclonal antibodies capable of specifically binding to a CCaMK polypeptide and/or fragments thereof. Such antibodies are raised against a CCaMK polypeptide or fragment thereof and are capable of distinguishing a CCaMK polypeptide from other polypeptides.

An immunological response is usually assayed with an immunoassay. Normally such immunoassays involve some purification of a source of antigen, for example, produced by the same cells and in the same fashion as the antigen was produced.

For the preparation and use of antibodies according to the present invention, including various immunoassay techniques and applications, see, e.g., Goding, *Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, New York, 1988. CCaMK-specific antibodies are useful, for example in: purifying a CCaMK polypeptide from a biological sample, such as a host cell expressing recombinant a CCaMK polypeptide; in cloning a CCaMK allele or homolog from an expression library; as antibody probes for protein blots and immunoassays; etc.

CCaMK polypeptides and antibodies can be labeled by joining, either covalently or noncovalently, to a substance which provides for a detectable signal by conventional methods. A wide variety of labels and conjugation techniques are known. Suitable labels include radionuclides, enzymes, substrates, cofactors, inhibitors, fluorescent agents, chemiluminescent agents, magnetic particles, etc.

Plant Transformation and Regeneration

Various nucleic acid constructs that include a CCaMK nucleic acid are useful for producing male-sterile plants. As detailed in the Examples below, transgenic plants containing as a transgene a nucleic acid construct in which a CCaMK nucleic acid is expressed in an antisense orientation are male sterile.

CCaMK nucleic acids can be expressed in plants or plant cells in a sense or antisense orientation under the control of an operably linked promoter that is capable of expression in a cell of a particular plant. Various promoters suitable for expression of heterologous genes in plant cells are well known, including constitutive promoters (e.g. the CaMV 35S promoter), organ- or tissue-specific promoters (e.g., the tapetum-specific TA29, A9 or Osg6B promoters), and promoters that are inducible by chemicals such as methyl jasminate, salicylic acid, or Safener, for example.

In addition to antisense expression of CCaMK in transgenic plants, as discussed below (see also, U.S. Pat. No. 5,283,184), the availability of CCaMK genes permits the use of other conventional methods for interfering with CCaMK gene expression, including triplex formation, production of an untranslatable plus-sense CCaMK RNA, etc.

A CCaMK promoter can be used to drive the expression of a CCaMK antisense transgene and also to express other nucleic acids in transgenic plants in an organ- and developmental stage-specific manner. For example, a CCaMK promoter can be used to drive the expression in transcriptional or translational fusions of antisense versions of nucleic acids encoding polypeptides necessary for male fertility, e.g., antisense inhibition of flavonoid biosynthesis (Van der Meer et al., *Plant Cell* 4:253–262, 1992), or to express, in a sense orientation, genes that interfere with male fertility, e.g., ribonuclease (Mariani et al., *Nature* 347:737–741, 1990); glucanase (Worrall et al., *Plant Cell* 4:759–771, 1992; Tsuchiya et al., *Plant Cell Physiol.* 36:487–494, 1995); Agrobacterium rhizogenes rolB (Spena et al., *Theor. Appl. Genet.* 84:520–527, 1992); and mitochondrial gene atp9 (Hernould et al., *Proc. Natl. Acad. Sci. USA* 90:2370–2374, 1993).

Any well-known method can be employed for plant cell transformation, culture, and regeneration in the practice of the present invention with regard to a particular plant species. Methods for introduction of foreign DNA into plant cells include, but are not limited to: transfer involving the use of *Agrobacterium tumefaciens* and appropriate Ti vectors, including binary vectors; chemically induced transfer (e.g., with polyethylene glycol); biolistics; and microinjection. See, e.g., An et al., *Plant Molecular Biology Manual* A3: 1–19, 1988.

The term "plant" encompasses any higher plant and progeny thereof, including monocots (e.g., lily, corn, rice, wheat, etc.), dicots (e.g., tobacco, potato, apple, tomato, etc.), gymnosperms, etc., and includes parts of plants, including reproductive units of a plant, fruit, flowers, wood, etc.

A "reproductive unit" of a plant is any potent part or tissue of the plant from which one can obtain a progeny of the plant, including, for example, seeds, cuttings, tubers, buds, bulbs, somatic embryos, cultured cell (e.g., callus or suspension cultures), etc.

The invention will be better understood by reference to the following Examples, which are intended to merely illustrate the best mode now known for practicing the invention. The scope of the invention is not to be considered limited thereto, however.

EXAMPLES

Example 1

Identification of Plant Calcium/Calmodulin-Dependent Protein Kinase Gene

Materials and Methods

Plant Material. Lily (*Lilium longiflorum* Thunb cv. Nellie White) plants were grown under greenhouse conditions and various parts were excised and frozen in liquid nitrogen.

PCR and cDNA Library Screening. Three different lily cDNA libraries made from developing anthers, mature and germinating pollen were used for PCR. Degenerate oligonucleotides corresponding to two highly conserved regions of mammalian $Ca^{2+}$/calmodulin-dependent protein kinases, DLKPEN (SEQ ID NO:12) and FNARRKL (SEQ ID NO:13), were used as primers for PCR (Hunter, *Cell* 50:823–829, 1987). The amplification reaction contained 1×PCR buffer (Cetus Corp.), 200 µM dNTPs, 50 pmoles of each primer, 1.5 mM $MgCl_2$, 2 µL cDNA library ($10^9$ pfu/mL), and 2.5 units of Taq DNA polymerase in a 100 µl total reaction volume. The cycling profile was 30 cycles, each cycle including 94° C. for 1 min, 48° C. for 1 min, and 72° C. for 1 min. The specific PCR product of the expected size (471 bp) was subcloned into pBluescriptII KS+ (Stratagene) and sequenced. This fragment was used to screen the cDNA library (Sambrook et al., 1989) from developing anthers (Kim et al., *Plant Mol. Biol.* 21:39–45, 1993) to obtain the lily CCaMK cDNA clone.

Sequence Analysis. The sequencing of the lily CCaMK cDNA was carried out using the Sanger dideoxy-nucleotide chain-termination method (Sanger et al., *Proc. Natl. Acad. Sci. USA* 74:5463–5467, 1977). A search of the GenBank/ EMBL databases (March, 1994) was done using GCG version 7.0 software (Devereaux et al., *Nucl. Acids Res.* 12:387–395, 1984).

Expression of the CCaMK Gene. An RNase protection assay (Sambrook et al., 1989) was performed using total RNA (20 µg) from various parts of lily. Total RNA was isolated from leaf, stem, and various organs from immature flower (Verwoerd et al., *Nucl. Acids Res.* 17:2362, 1989). A 612 bp fragment of the CCaMK coding region (nucleotides 1010–1621) was subcloned into pBluescriptII KS+ plasmid (Stratagene) and used as a template for making the $^{32}$P-labeled RNA probe.

Southern Analysis. 5 µg of lily genomic DNA was digested with different restriction enzymes and transferred to a nylon membrane, followed by Southern analysis using standard protocols (Sambrook et al., 1989).

Expression of CCaMK in *E. coli*. The CCaMK protein was expressed in *E. coli* using pET3b vector (Studier et al., *Meth. Enzymol.* 185:60–89, 1990; Novagen, Inc.). *E. coli* strain BL21 (DE3)-pLysS was transformed with the pET3b expression vector containing CCaMK cDNA. Bacteria were grown at 35° C. in M9 minimal medium supplemented with 2 g/L casamino acid, 100 mg/L ampicillin, 25 mg/L chloramphenicol. The protein was induced by adding 0.5 mM isopropylthiogalactoside (IPTG) when the $OD_{600}$ reached 0.5–0.7. Three hours after induction, cells were collected by centrifugation, the protein was then extracted and purified by using calmodulin-affinity Sepharose 4B column according to Hagiwara et al. (*J. Biol. Chem.* 266, 16401–16408, 1991). The quality of the purified protein was checked by SDS-polyacrylamide gel electrophoresis.

Preparation of $^{35}$S-Labeled Calmodulin and Calmodulin-Binding Assay. $^{35}$S-labeled calmodulin was prepared as described by Fromm and Chua (*Plant Mol. Biol. Rep.* 10:199–206, 1992) using a calmodulin cDNA (Jena et al., *Proc. Natl. Acad. Sci. USA* 86:3644–3648, 1989) cloned into pET3b expression vector. The CCaMK protein (250 ng) was electrophoretically transferred to a nitrocellulose filter and incubated in a solution containing 50 mM Tris-HCl (pH 7.5), 150 mM NaCl, 1% (w/v) nonfat dry milk, and 50 nM $^{35}$S-calmodulin (0.5×$10^6$ cpm/µg) plus either 1 mM $CaCl_2$ or 5 mM EGTA (Sikela and Hahn, *Proc. Natl. Acad. Sci. USA* 84:3038–3042, 1987). A 50-fold excess of unlabeled calmodulin was used as a competitor to show specific binding of calmodulin to CCaMK. Calmodulin binding to CCaMK was quantified by measuring radioactivity in each slot using a liquid scintillation counter.

$^{45}$Ca-Binding Assay. Calcium binding to CCaMK was studied as described by Maruyama et al. (*J. Biochem.* 95:511–519, 1984). Purified CCaMK protein was transferred to Zeta-probe membrane (Bio-Rad) using slot blot apparatus (Millipore) and incubated with buffer containing 10 mM Tris-HCl (pH 7.5), 100 mM KCl, 5 mM $MgCl_2$, and 10 µCi/mL $^{45}$Ca for 20 min. The membrane was washed for 5 min in the same buffer without $^{45}$Ca and exposed to X-ray film.

Results and Discussion

A partial clone of lily CCaMK (471 bp) was obtained from developing anthers of lily by PCR using degenerate oligonucleotide primers corresponding to two highly conserved regions of mammalian $Ca^{2+}$/calmodulin-dependent protein kinases. This fragment was not amplified when the cDNA libraries made from mature and germinating pollens were used. The nucleotide sequence of the PCR-amplified fragment contained conserved sequences corresponding to catalytic subdomains VI–XI and part of the calmodulin-binding domain of mammalian CaM KII (Hanks et al., *Science* 241:42–52, 1988).

A 2514 bp lily cDNA clone was obtained by screening the cDNA library using the PCR amplified fragment as a probe and its nucleotide sequence was determined (FIG. 1, SEQ ID NO:1). The cDNA codes for a polypeptide of 520 amino acids flanked by a 634 bp 5'-untranslated region and a 317 bp 3'-untranslated region. The lily CCaMK polypeptide contains all eleven major conserved subdomains of the catalytic domain of serine/threonine kinases (Hanks et al., *Science* 241:42–52, 1988). Sequence comparisons revealed that CCaMK has high homology to $Ca^{2+}$/calmodulin-dependent protein kinases, especially in the kinase and the calmodulin-binding domains (amino acid residues 1-338 of SEQ ID NO:1). This region of CCaMK has highest homology to kinases from apple (Gen3:Mdstpkn), rat (Gen2:Ratpk2g), human (Gen1:Humccdpkb), and fruitfly (Gen2:Drocdpkb, Gen2:Drocdpkd).

The calmodulin-binding region of CCaMK (ARRKLRAAAIASVL, residues 325–338 of SEQ ID NO:1) has 79% similarity to the calmodulin-binding domain (ARRKLKGAILTTML, residues 295–308 of SEQ ID NO:9) of α-subunit of mammalian CaM KII, a well characterized $Ca^{2+}$/calmodulin-dependent protein kinase (Colbran et al., *Biochem. J.* 258:313–325, 1989) and 43% and 50% similarity to the calmodulin-binding domains of CaM KII homologs of yeast and Aspergillus, respectively (Pausch et al., *EMBO J.* 10:1511–1522, 1991; Kornstein et al., *Gene* 113, 75–82, 1992). The helical wheel projection of the calmodulin-binding domain (amino acid residues 325–338 of SEQ ID NO:1) of CCaMK formed a basic amphipathic alpha helix (O'Neill et al., *Trends in Biochem. Sci.* 15:59–64, 1990), a characteristic feature of calmodulin-binding sites.

The sequence downstream of the calmodulin-binding region of CCaMK (amino acid residues 339–520 of SEQ ID NO:1) does not have significant homology to known $Ca^{2+}$/calmodulin-dependent protein kinases. Further analysis of this region revealed the presence of three $Ca^{2+}$-binding EF-hand motifs that had the highest homology (52–54% similarity; 32–35% identity) to a family of genes belonging to visinin-like $Ca^{2+}$-binding proteins (FIG. 2), which are found mainly in neural tissue (Kuno et al., *Biochem. Biophys. Res. Commun.* 184:1219–1225, 1992; Kobayashi et al., *Biochem. Biophys. Res. Commun.* 189:511–517, 1992; Lenz et al., *Mol. Brain Res.* 15:133–140, 1992; Okazaki et al., *Biochem. Biophys. Res. Commun.* 185:147–153, 1992; Pongs et al., *Neuron* 11:15–28, 1993). Even though four EF-hand motifs are present in the calmodulin-like domain of CDPKs, this domain shared only 25% identity with the visinin-like domain of CCaMK. Out of the six residues of the EF-hand [positions 1(X), 3(Y), 5(Z), 7(-Y), 9(-X), and 12(-Z)] involved in $Ca^{2+}$-binding, position 7(-Y) is not conserved in CCaMK. A similar deviation is also observed in visinin-like proteins, wherein the residue at position 9(-X) of the EF-hand motifs of visinin-like proteins (FIG. 2) is not conserved. These differences between the EF-hands of the visinin-like domain of CCaMK and other $Ca^{2+}$-binding proteins may affect $Ca^{2+}$-binding and protein-protein interactions.

Frequenin, neurocalcin, hippocalcin, and visinin-like neural $Ca^{2+}$-binding proteins are members of a novel family of $Ca^{2+}$ sensitive regulators, each with three $Ca^{2+}$-binding EF-hand motifs. The presence of such proteins has not been reported in plants. These proteins are activated at nanomolar concentrations of $Ca^{2+}$. At such low levels, calmodulin-dependent pathways are not activated. Frequenin acts as a $Ca^{2+}$-sensitive activator of photoreceptor particulate guanylyl cyclase (Pongs et al., *Neuron* 11:15–28, 1993) and may be involved in activating protein kinases and phosphatases in response to changes in intracellular $Ca^{2+}$, similar to the action of calmodulin (Pongs et al., *Neuron* 11:15–28, 1993).

An unusual feature of CCaMK is the presence of a putative biotin-binding site (LKAMKMNSLI, amino acid residues 389–398 of SEQ ID NO:1) within the visinin-like domain (FIG. 2). Such a biotin-binding site has not been observed in neural visinin-like proteins. Biotin plays a catalytic role in several essential metabolic carboxylation and decarboxylation reactions (Chandler et al., *J. Biol. Chem.* 263:1013–1016, 1988). CCaMK also contains two consensus motifs, RXXT/S (FIGS. 1 and 2), analogous to the autophosphorylation site of mammalian CaM KII and its homologs (Colbran et al., *Curr. Top. Cell. Regul.* 31:181–221, 1990).

The structural features of the CCaMK gene indicate that it is a novel chimeric $Ca^{2+}$- and $Ca^{2+}$/calmodulin-dependent protein kinase with two discrete regulatory domains, a calmodulin-binding domain and a visinin-like $Ca^{2+}$-binding domain (FIG. 3). The presence of these distinct domains suggests dual modes of regulation. Furthermore, the presence of a putative biotin-binding site suggests yet another mode of regulation, adding to the functional diversity of CCaMK. The chimeric feature of the CCaMK gene suggests that it has evolved from a fusion of two genes that are functionally different and phylogenetically diverse in origin.

Figure 4:
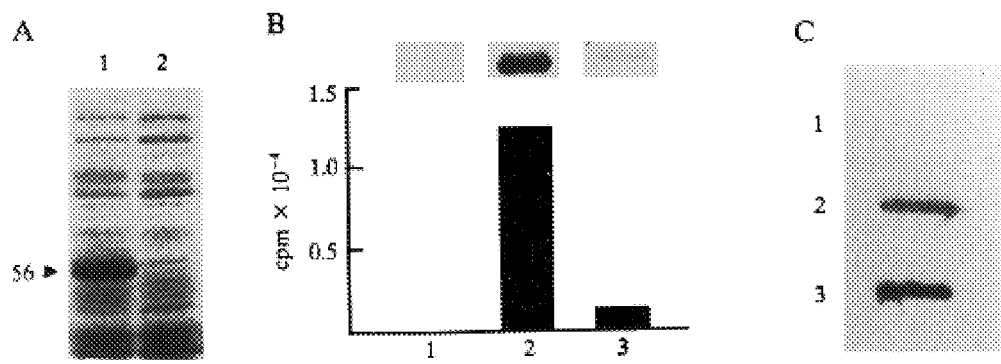
FIG. 4A shows SDS-polyacrylamide gel electrophoresis (SDS-PAGE) of lily CCaMK polypeptide expressed in E. coli after induction by IPTG. Lanes: 1, IPTG-induced cell extract; 2, uninduced cell extract. Protein size is marked on the left.
FIG. 4B shows binding of lily CCaMK protein (250 ng) to $^{35}S$-labeled calmodulin (50 nM) in the presence of either 5 mM EGTA or 1 mM $CaCl_2$. The histogram shows radioactivity (cpm) on the nitrocellulose filter. Columns: 1, 5 mM EGTA; 2, 1 mM $CaCl_2$; 3, 1 mM $CaCl_2$ plus 2.5 µM unlabeled calmodulin. An autoradiogram is shown on top of each corresponding column.
FIG. 4C shows $Ca^{2+}$-binding to lily CCaMK. 1, bovine serum albumin (2 µg); 2, calmodulin (2 µg); 3, CCaMK (2 µg).

The functional role of the predicted structural motifs of CCaMK was studied using $Ca^{2+}$ and calmodulinbinding assays. Recombinant lily CCaMK protein was produced in transformed *E. coli* (FIG. 4A) and purified by calmodulin-affinity chromatography to near homogeneity, as judged by SDS-PAGE. FIG. 4B shows binding of lily CCaMK protein (250 ng) after transfer to a nitrocellulose filter and incubation with $^{35}$S-labeled calmodulin in a buffer containing either 5 mM EGTA or 1 mM $CaCl_2$. Calmodulin binds to CCaMK only in the presence of $Ca^{2+}$.

To determine the functional role of the EF-hand motifs within the visinin-like domain, $^{45}$Ca-binding assays were carried out. FIG. 4C shows that $^{45}$Ca binds directly to lily CCaMK protein transferred to a Zeta-probe membrane. When incubated with excess amounts (50-fold) of unlabeled calmodulin, the binding of $^{35}$S-labeled calmodulin to CCaMK was effectively reduced, suggesting that calmodulin binding to CCaMK was specific. Moreover, CCaMK showed a $Ca^{2+}$-dependent shift in mobility, as revealed by SDS-PAGE. These results suggest that CCaMK has some of the structural properties of both $Ca^{2+}$-dependent and $Ca^{2+}$/calmodulin-dependent protein kinases (FIG. 3). The intensity of a calmodulin control is less than CCaMK, possibly as a result of inefficient binding of calmodulin to the membrane (Van Eldik and Wolchok, *Biochem. Biophys. Res. Commun.* 124:752–759, 1984)).

Figure 5:
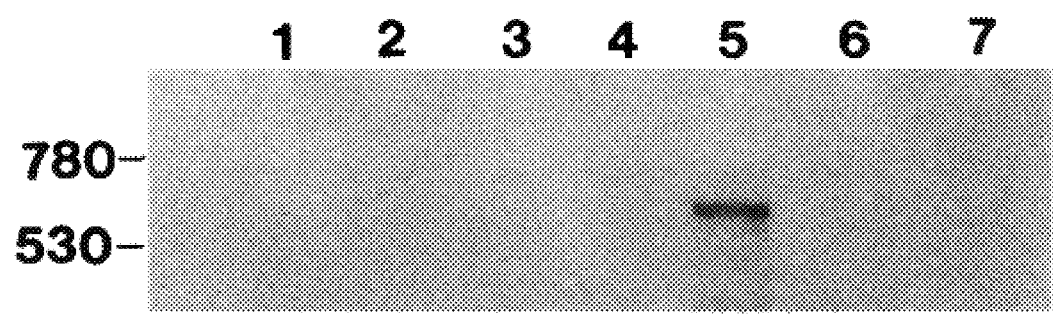
FIG. 5 shows results of an RNase protection assay using total RNA (20 µg) from various parts of lily. Lanes: 1, leaf; 2, stem; 3, anthers from phase II; 4, sepals and petals from phase III; 5 anthers from phase III; 6, sepals and petals from phase III; 7, yeast tRNA control.

The CCaMK gene was preferentially expressed during phase III (Wang et al., *Am. J. Bot.* 79:118–127, 1992) of anther development, as revealed by a ribonuclease protection assay (FIG. 5). Phases II and III correspond to stages of anther development as described by Wang et al. (*Am. J. Bot.* 79:118–127, 1992). The expression of lily CCaMK during phase III suggests the involvement of CCaMK in microsporogenesis. Some EF-hand proteins like calmodulin (Moncrief et al., *J. Mol. Evol.* 30:522–562, 1990) are ubiquitous and are active in diverse tissues. However, visinin-like proteins are restricted to specialized tissues such as neurons. CCaMK, which has a visinin-like domain, is also expressed in an organ-specific manner.

Figure 6:
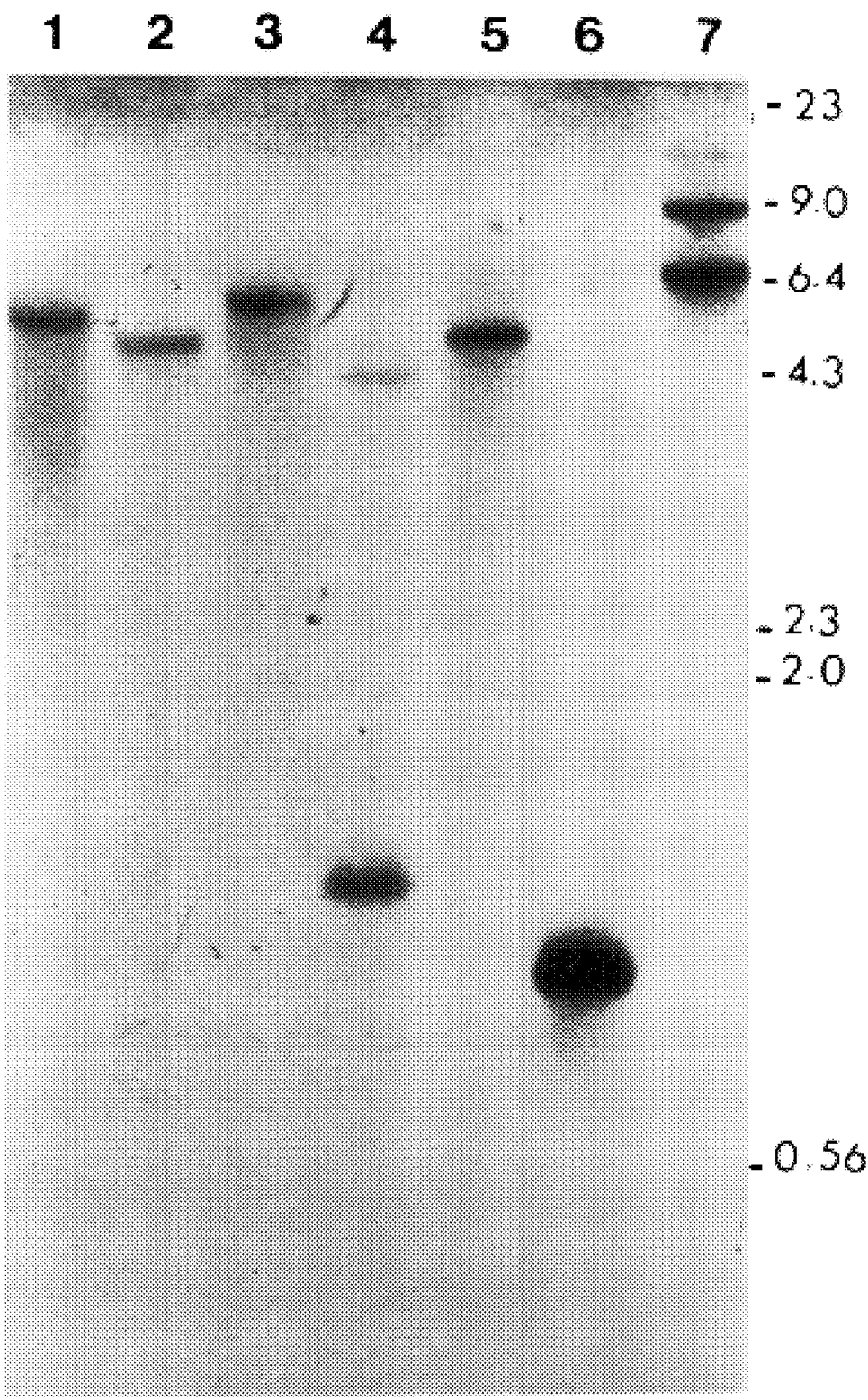
FIG. 6 shows a Southern blot of lily genomic DNA digested with restriction enzymes and probed with a lily CCaMK cDNA probe. Lanes: 1, DraI; 2, EcoRI; 3, EcoRV; 4, HindIII, 5, PstI; 6, XbaI; 7, XhoI.

Genomic Southern analysis revealed that CCaMK is coded by a single gene (FIG. 6). Hybridization at low stringency using the lily CCaMK cDNA probe indicated the presence of a CCaMK homolog in other plants, such as Arabidopsis, apple and tobacco. The tobacco homolog to lily CCaMK has been cloned (SEQ ID NO:10) and its deduced polypeptide displays structural components similar to lily CCaMK, including calmodulin-binding and visinin-like domains. The CCaMK-like gene is present in both monocotyledonous and dicotyledonous plants.

The $Ca^{2+}$-signaling pathway mediated through $Ca^{2+}$/calmodulin-dependent protein phosphorylation is well established in animals. This report confirms the presence of a novel $Ca^{2+}$/calmodulin-dependent protein kinase in plants. However, the presence of a visinin-like $Ca^{2+}$-binding domain in CCaMK adds an additional Ca$^{2+}$ sensing mechanism and distinguishes CCaMK from all other known Ca$^{2+}$/calmodulin-dependent protein kinases. The discovery of the CCaMK gene adds a new dimension to the understanding of Ca$^{2+}$-mediated signal transduction in plants.

Example 2

Biochemical Properties of Lily CCaMK

Materials and Methods

Materials. Proteinase inhibitors, histone IIAS, IIIS, myelin basic protein (MBP), syntide-2, GS peptide (PLSRTLSVAAKK, SEQ ID NO:14), MBP peptide (QKRPSQRSKYL, SEQ ID NO:15) and spinach calmodulin were purchased from Sigma. [γ-$^{32}$P]ATP was obtained from DuPont NEN. Calmodulin-Sepharose 4B and Klenow enzyme were obtained from Pharmacia. Restriction enzymes and biotinylated calmodulin were from Bethesda Research Laboratory.

Expression and Purification of CCaMK. *E. coli* cells carrying plasmid pET3b (Novagen, Inc.) containing CCaMK cDNA were induced by IPTG as described earlier (Patil et al., *Proc. Natl. Acad. Sci. USA* 92:4797–4801, 1995). IPTG-induced *E. coli* cells were harvested and suspended in a homogenization buffer (40 mM Tris-HCl, pH 7.6, 1 mM DTT, 2 mM EDTA, 0.1% Triton-X 100, 1 mM PMSF and 10 μg/mL each of leupeptin, pepstatin and antipain). Cells were broken by freeze-thawing followed by sonication. Subsequent procedures were carried out at 4° C. The cell extract was clarified by centrifugation at 12,000 g for 30 min. Solid ammonium sulfate (50% saturation) was added to the supernatant and incubated on ice for 1–4 hr. The enzyme was recovered by centrifugation for 30 min at 12,000 g. The pellet was solubilized in column buffer (40 mM Tris-HCl, pH 7.6, 1 mM CaCl$_2$, 1 mM dithiothreitol (DTT), 10% ethylene glycol, 0.05% Tween-20, 50 mM NaCl, 1 mM PMSF and 10 μg/mL each of leupeptin, pepstatin and antipain) and applied onto a calmodulin-Sepharose column, which was previously equilibrated with the column buffer. The column was washed first with column buffer, then with column buffer containing 1M NaCl. CCaMK was eluted from the column with buffer containing 40 mM Tris (pH 7.6), 1.5 mM EGTA, 10% ethylene glycol, 0.05% Tween-20, 200 mM NaCl and 1 mM PMSF. Fractions containing CCaMK were pooled and thoroughly dialyzed against buffer containing 40 mM Tris (pH 7.6), 1 mM DTT, 1 mM EDTA and 10% ethylene glycol.

Gel Electrophoresis. SDS-PAGE was performed according to Laemmli (*Nature* 237:680–685, 1970). Non-denaturing gel electrophoresis was performed using a 14% separating gel in 375 mM Tris-Cl (pH 8.8), 5% stacking gel in 125 mM Tris-Cl (pH 6.8) and 25 mM Tris-192 mM glycine electrophoresis buffer (pH 8.3), at 80 V for 8 h. Protein bands were visualized by staining with Coomassie Brilliant Blue.

Calmodulin-Binding Assays. The potato calmodulin PCM6 cDNA (Takezawa et al., *Plant Mol. Biol.* 27:693–703, 1995) was cloned into the pET3b expression vector, and $^{35}$S-labeled calmodulin was prepared as described by Fromm and Chua (*Plant Mol. Biol. Rep.* 10:199–206, 1992). Wild-type and mutant CCaMK proteins were electrophoretically transferred to nitrocellulose filters and incubated in binding buffer (10 mM Tris-Cl, pH 7.5, 150 mM NaCl, and 1% (w/v) non-fat dry milk) containing $^{35}$S-calmodulin (0.5× 10$^6$ cpm/μg) plus either 1 mM CaCl$_2$ or 5 mM EGTA as previously described by Patil et al. (*Proc. Natl. Acad. Sci. USA* 92:4797–4801, 1995). Binding assays using biotinylated calmodulin were performed as previously described by Reddy et al. (*Plant Sci.* 94:109–117, 1993).

Assay for Peptide Binding to Calmodulin. Synthetic peptides were prepared using an Applied Biosystems peptide synthesizer 431A. Different lengths of synthetic peptides were incubated with 100 pmol (1.7 μg) of calmodulin in 10 μL of 20 mM Hepes (pH 7.5) for 5 min and analyzed by non-denaturing PAGE.

Deletion Mutants of CCaMK. The mutant construct denoted 1-356 was created by removing a 0.9 kb BamHI fragment containing the visinin-like domain from the original CCaMK expression plasmid pNY10. The mutant construct denoted 1-322 was created by partial digestion of pNY10 with XbaI and filling the site with the Klenow fragment of DNA polymerase I. The resulting construct was then inserted into the pET14b expression vector. The mutant proteins were expressed in *E. coli* and purified using either a calmodulin-Sepharose column (Pharmacia) or a Ni$^{2+}$-resin column (Novagen) following manufacturer's instructions.

Site-Directed Mutagenesis and Expression of the Visinin-Like Domain. A 0.9 kb BamHI fragment containing the visinin-like domain of CCaMK was subcloned into M13mp18 RF and site-directed mutagenesis was performed (Kunkel et al., *Meth. Enzymol.* 154:367–382, 1987). oligonucleotide primers used for the site-directed mutagenesis were 5'-CTCTCATGGCTATAGTTCC-3' (SEQ ID NO:16) for EF-hand I mutation, 5'-CCTCCTTGGCGATACATCC-3' (SEQ ID NO:17) for EF-hand II mutation, and 5'-GTCGAACGCGACAACTCC-3' (SEQ ID NO:18) for EF-hand III mutation. An Nde I site was created at the position of amino acid residue 358 (Met) using 5' GGATCCCATCATATGAAATCG-3'(SEQ ID NO:19). Native and the mutant constructs were then inserted into the pET14b expression vector. All mutant sequences were confirmed by DNA sequencing using the fmol PCR sequencing kit (Promega).

Protein Kinase Assay. Phosphorylation assays (25 μL) were carried out at 30° C. in 50 mM Hepes (pH 7.6), 1 mM DTT, 10 mM magnesium acetate, 200 μM [γ-$^{32}$P]ATP, (1,500 to 2000 cpm/pmol) in the presence of either 2.5 mM EGTA or indicated amounts of Ca$^{2+}$ and calmodulin. Protein (0.2 mg/mL), and synthetic peptides (100 μM) were added in the reaction mixture to study substrate phosphorylation. When protein substrates were used, the reaction was terminated by adding SDS-PAGE sample buffer (Laemmli, *Nature* 237:680–685, 1970) and analyzed after electrophoresis on 12% SDS polyacrylamide gels. Proteins were visualized by staining with Coomassie Brilliant Blue. The gels were dried and subjected to autoradiography. Incorporation of $^{32}$P into the substrate was determined by counting the excised protein bands in a liquid scintillation counter. When peptide substrates were used the reaction was terminated by spotting the reaction mixture on P81 phosphocellulose filters (Whatman). The filters were washed in 75 mM phosphoric acid and $^{32}$P incorporation was determined (Roskoski, Jr., *Meth. Enzymol.* 99:3–6, 1983).

Autophosphorylation Assay. The autophosphorylation assay was carried out at 30° C. in the presence of 50 mM Hepes, pH 7.5 containing 10 mM magnesium acetate, 1 mM DTT, 1 mM [γ-$^{32}$P]ATP (300 to 400 cpm/pmol) and either EGTA (2.5 mM), CaCl$_2$ (0.5 mM), or CaCl$_2$ (0.5 mM) plus calmodulin (1 μM). For time course assays (100 μL), 1.2 μg (21.4 pmol) of CCaMK and 1 mM [γ-$^{32}$P]ATP (2,000–3,000cpm/pmol) were used. Aliquots (10 μL) were transferred at indicated time points into SDS-PAGE sample buffer to stop the reaction. Aliquots for the zero time point were taken immediately after the addition of CCaMK. The samples were then analyzed by electrophoresis on a 12% SDS polyacrylamide gel. The amount of phosphate transferred to the enzyme was determined by counting the radioactivity of the excised CCaMK bands in a liquid scintillation counter.

Phosphoamino Acid Analysis. The purified CCaMK (200 ng) was autophosphorylated in the presence of EGTA (2.5 mM), or $CaCl_2$ (0.5 mM) or $CaCl_2$ (0.5 mM) plus 1 μM calmodulin, and subjected to SDS-PAGE. The gel was briefly stained with Coomassie Brilliant Blue, and CCaMK bands were excised and the protein was eluted from the gel. The eluted protein was hydrolyzed with 6N HCl for 2 h at 110° C. and subjected to paper chromatography using propionic acid : 1M $NH_4OH$ : isopropyl alcohol (45:17.5:17.5) as a solvent (Cooper, *Meth. Enzymol.* 99:387–402, 1983). Phosphoserine and phosphothreonine standards (50 mg/mL in 10% w/v isopropyl alcohol) were visualized by ninhydrin reagent.

Results

Figure 7A:
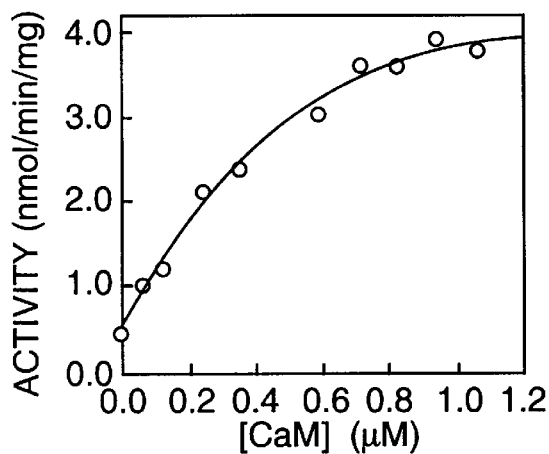
FIG. 7A shows $Ca^{2+}$/calmodulin-dependent phosphorylation of histone IIAS by lily CCaMK in the presence of 0.5 mM $CaCl_2$ and increasing amounts of calmodulin (µM). CCaMK activity is presented as nmol phosphate/min/mg CCaMK.
Figure 7B:
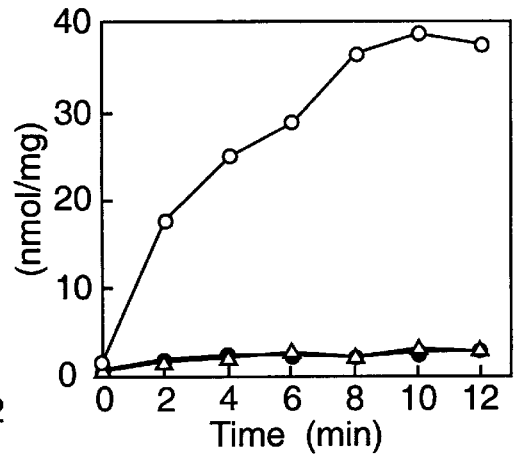
FIG. 7B shows the time course of phosphorylation of histone IIAS by lily CCaMK in the presence of 2.5 mM EGTA (●) or 0.5 mM $CaCl_2$ (Δ) or 0.5 mM $CaCl_2$ and 1 µM calmodulin (○). CCaMK activity is represented as nmol of phosphate per mg CCaMK.

To study the $Ca^{2+}$/calmodulin-dependent kinase activity of lily CCaMK, the *E. coli*-expressed protein was purified. The protein was essentially pure as revealed by SDS-PAGE and was stable at 4° C. for a few days. The purified protein was used to phosphorylate different substrates such as casein, histones, myelin basic protein, and synthetic peptides. Histone IIAS was found to be the most reactive protein substrate for CCaMK, and was used for studying calmodulin concentration-dependent protein kinase activity. The addition of increasing amounts of calmodulin in the presence of 0.5 mM $Ca^{2+}$ stimulated CCaMK activity (FIG. 7A). Kinase activity was saturated at calmodulin concentrations around 1.0 μM. The concentration of calmodulin required for half-maximal activity (Ka) of CCaMK was approximately 0.2 μM. The time course studies revealed that histone IIAS phosphorylation was saturated after 10 min in the presence of $Ca^{2+}$/calmodulin (FIG. 7B). In the presence of 2.5 mM EGTA or 0.5 mM $Ca^{2+}$ alone, the enzyme has a basal activity that is ten- to fifteen-fold lower than the maximal activity achieved with $Ca^{2+}$/calmodulin. Among other protein substrates tested, CCaMK phosphorylated histone IIIS and myelin basic protein, but it did not phosphorylate phosvitin, PEP carboxylase, synapsin I, and casein. CCaMK also phosphorylated synthetic peptides such as GS peptide, MBP peptide, and syntide-2. Among these peptides, GS peptide was most efficiently phosphorylated by CCaMK in the presence of $Ca^{2+}$/calmodulin.

Figure 8:
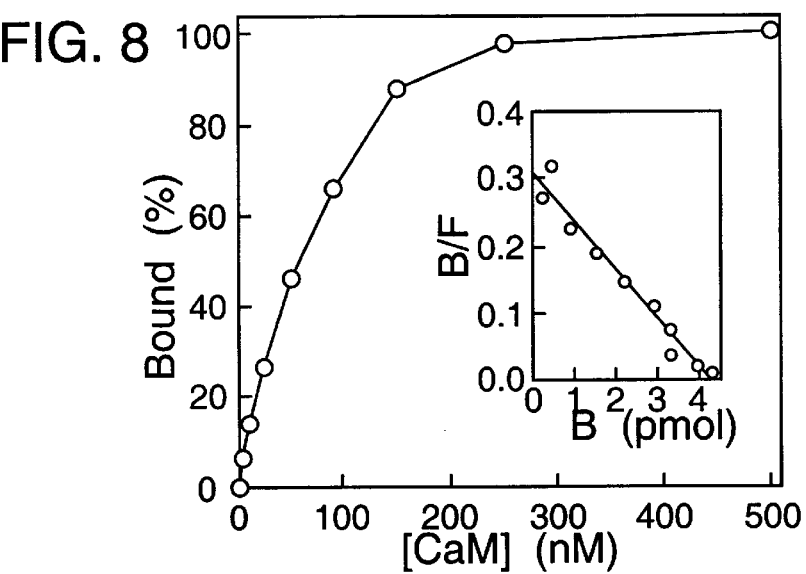
FIG. 8 shows a saturation curve of $^{35}S$-calmodulin binding to lily CCaMK. The amount of bound calmodulin at each point is represented as percent of maximal binding. Inset: Scatchard plot analysis (bound/free and bound calmodulin are expressed as B/F and B, respectively).

FIG. 8 shows a saturation curve of $^{35}$S-calmodulin binding to purified CCaMK to determine the calmodulin-binding affinity of CCaMK. Upon induction of CCaMK expression in *E. coli*, 4 pmol of protein was separated by SDS-PAGE, electrophoretically transferred to a nitrocellulose filter, and incubated with different amounts of $^{35}$S-labeled calmodulin. After washing in buffer without $^{35}$S-calmodulin, the radioactivity of the filter was measured using a liquid scintillation counter. Binding of calmodulin to CCaMK saturated at concentrations above 300 nM. From the saturation curve, the dissociation constant (Kd) of calmodulin for CCaMK was estimated to be approximately 55 nM. The binding of calmodulin to CCaMK was completely blocked in the presence of 5 mM EGTA. A Scatchard plot of the binding data shows that the binding ratio of calmodulin to CCaMK is 1:1 (FIG. 8, inset), indicating that CCaMK has a single calmodulin-binding site.

To identify the calmodulin-binding region of CCaMK, truncated mutant constructs were prepared (FIG. 9A). The CCaMK mutant 1-356 lacks the C-terminal domain which has high homology to visinin-like proteins. Another mutant, CCaMK 1-322, is further truncated but retains all eleven domains conserved in serine/threonine protein kinases (Hanks et al., *Science* 241:42–52, 1988). Native CCaMK (amino acid residues 1-520, SEQ ID NO:1), and truncated mutants 1-356 and 1-322 were expressed in *E. coli*, subjected to SDS-PAGE, and transferred to nitrocellulose filter. Excised bands containing the expressed proteins were assayed for binding to $^{35}$S-calmodulin in the presence of $Ca^{2+}$. The radioactivity of bound $^{35}$S-calmodulin was 11,600 cpm for native CCaMK, 12,500 cpm for the mutant 1-356, and 99 cpm for the mutant 1-322, respectively. Thus, binding of calmodulin to native and mutant 1-356 CCaMKs were similar; calmodulin did not bind to the mutant CCaMK 1-322 (FIG. 9A, in boxed region), indicating that amino acid residues 322–356 (FIG. 9A) are essential for calmodulin-binding to CCaMK. Another mutant, CCaMK 1-341, also binds to calmodulin in the presence of $Ca^{2+}$. Similar results were obtained when biotinylated calmodulin was used instead of $^{35}$S-calmodulin. Calmodulin binding to native and mutant CCaMKs was prevented by the addition of 5 mM EGTA, indicating that $Ca^{2+}$ is required for calmodulin binding. Comparison of amino acid residues of this region of CCaMK corresponding to regions of animal CaMKIIα revealed high homology (FIG. 9B).

Figure 10:
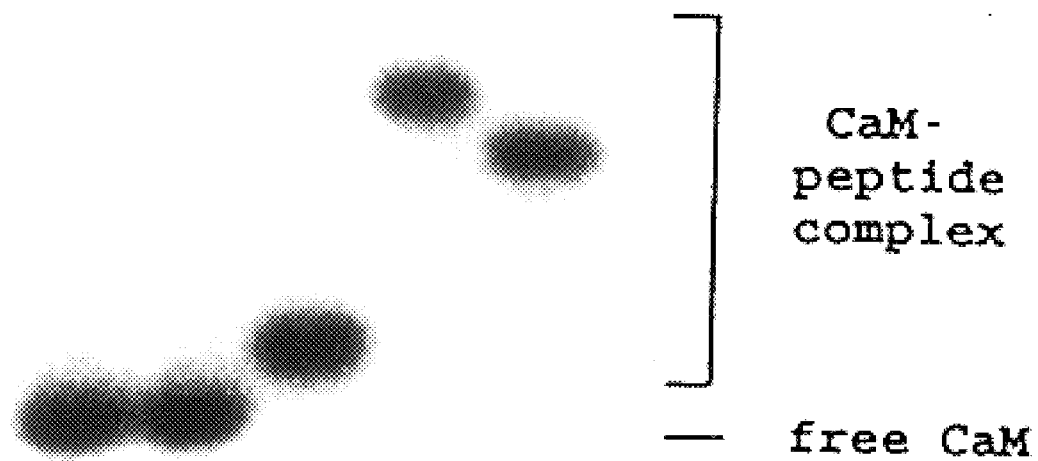
FIG. 10A–10C show calmodulin binding to synthetic peptides from the calmodulin-binding region (residues 311–340) in a gel mobility shift assay. Non-denaturing gel electrophoresis performed in the presence of 0.5 mM $CaCl_2$ using calmodulin alone (lane 1) or a mixture of calmodulin and each of the following peptides: CCaMK 328–340 (lane 2); CCaMK 322–340 (lane 3); 317–340 (lane 4); and 311–340 (lane 5). The bands of calmodulin (free CaM) or CaM-peptide complex were visualized by Coomassie Brilliant Blue.

Synthetic peptides from the calmodulin-binding region (amino acid residues 311–340, SEQ ID NO:1) were used to identify amino acid residues necessary for calmodulin-binding by a gel mobility-shift assay using nondenaturing PAGE in the presence of 0.5 mM $CaCl_2$. The bands of calmodulin and calmodulin-peptide complex were visualized by staining with Coomassie Brilliant Blue. Calmodulin mixed with peptides 311–340, 317–340, and 322–340 migrated above the position of calmodulin alone. Peptide 328–340 did not affect the mobility of calmodulin (FIG. 10), suggesting that the calmodulin-binding site exists between amino acid residues 322–340. Addition of these peptides to calmodulin in the presence of 2.5 mM EGTA did not affect the mobility of calmodulin, suggesting that peptide binding to calmodulin is $Ca^{2+}$-dependent. Increasing amounts of peptide 322–340 facilitates the gel mobility shift towards the upper, higher molecular weight position. Similar results were obtained when peptides 317–340 and 311–340 were used, suggesting that amino acid residues 322–340 have a pivotal role in CCaMK calmodulin binding.

The helical wheel projection revealed that amino acid residues 325–338 of CCaMK (SEQ ID NO:1) form a basic amphiphilic α helix (O'Neil and DeGrado, *Trends Biochem. Sci.* 15:59–64, 1990) similar to CaMKIIα (FIG. 11).

Figure 13A:
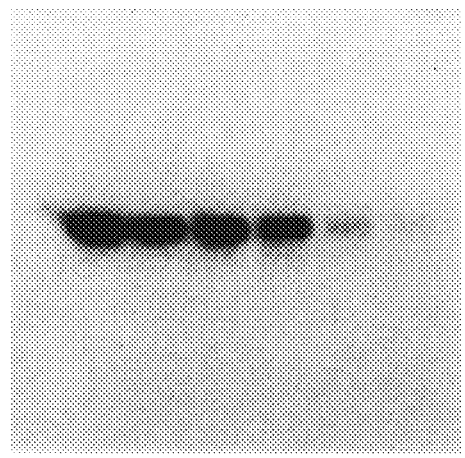
FIG. 13A shows the effect of calmodulin on $Ca^{2+}$-dependent autophosphorylation of lily CCaMK in the presence of $CaCl_2$ (0.5 mM) and increasing concentrations of calmodulin. Lane 1, +$CaCl_2$, (0.5 mM); lanes 2–6, +$CaCl_2$ (0.5 mM) and 60, 120, 240, 360, and 480 nM of calmodulin respectively.

To study autophosphorylation, CCaMK was incubated at 30° C. with 10 mM magnesium acetate, 1 mM [γ-$^{32}$P] ATP and 2.5 mM EGTA. In 30 min, approximately 0.098 mol $^{32}$P/mol of CCaMK was incorporated. This basal autophosphorylation was induced approximately 3.4 fold in the presence of 0.5 MM $CaCl_2$ (0.339 mol $^{32}$P/mol of CCaMK) (FIG. 12). Increasing the incubation time to 60 min did not improve the stoichiometry of $Ca^{2+}$-dependent autophosphorylation. $Ca^{2+}$-dependent autophosphorylation was inhibited to basal levels (0.061 mol $^{32}$P/mol of CCaMK) by the addition of 1 μM calmodulin (FIG. 12). Calmodulin inhibits $Ca^{2+}$- stimulated autophosphorylation in a concentration dependent manner (FIG. 13A). These results indicate that $Ca^{2+}$ and calmodulin have opposite effects on autophosphorylation of CCaMK. Phosphoamino acid analysis revealed that CCaMK autophosphorylates at the threonine residue(s) (FIG. 13B), and that autophosphorylation was stimulated by $Ca^{2+}$ and inhibited by $Ca^{2+}$/calmodulin.

Figure 14B:
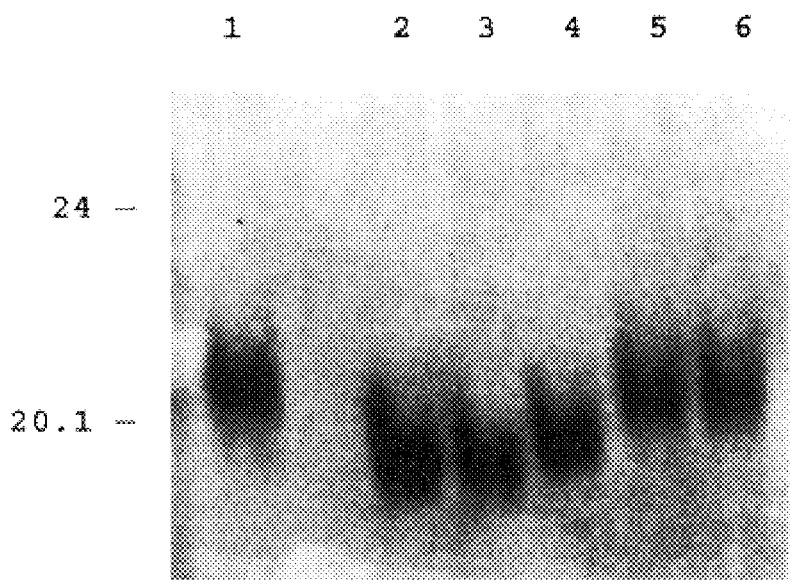
FIG. 14B shows the $Ca^{2+}$-dependent mobility shift of wild-type CCaMK and CCamKs mutated in the visinin-like domain in the presence of 2.5 mM EGTA (lane 1) or 0.5 mM $CaCl_2$ (lanes 2–6). Wild-type protein (lanes 1 and 2), proteins mutated in the EF hand I (lane 3), EF-hand II (lane 4), EF-hand III (lane 5), and all three EF hands (lane 6) are shown.

Apart from the calmodulin-binding domain, CCaMK has another regulatory domain nearer the C-terminus that has high homology to animal visinin-like proteins. The visinin-like domain of CCaMK contains three EF-hand motifs with conserved Ca²⁺-ligating amino acid residues (FIG. 14A). To study Ca²⁺-binding properties of the visinin-like domain of CCaMK, recombinant visinin-like domain protein was expressed in *E. coli*, using the pET14b expression vector. The visinin-like domain protein was expressed at high levels upon induction with 0.5 mM IPTG. Most of the protein was present in the soluble fraction. The expressed protein was purified using a Ni²⁺ resin column. Protein eluted from the column with 1M imidazole buffer was dialyzed in 50 mM Tris-Cl (pH 7.5) and used in a Ca²⁺-dependent mobility shift assay. Electrophoretic mobility of the recombinant visinin-like domain protein on a 14% SDS-polyacrylamide gel was just above the 20.1 kDa molecular-weight marker in the presence of 2.5 mM EGTA. Addition of Ca²⁺ shifted the electrophoretic mobility toward a lower molecular weight (FIG. 14B), suggesting that Ca²⁺ binding to the recombinant visinin-like domain protein induces a conformational change.

Figure 15:
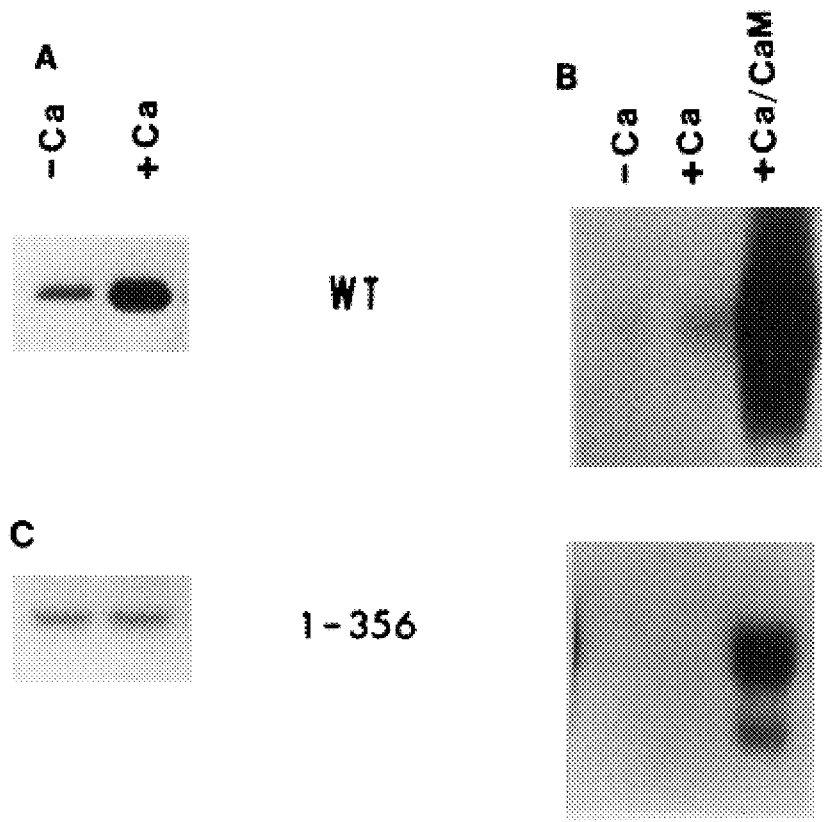
FIG. 15A–15D show a comparison of enzyme activity of wild-type (A and B) and a truncated lily CCaMK mutant (denoted 1-356) (C and D) with respect to $Ca^{2+}$-dependent autophosphorylation (A and C) and $Ca^{2+}$/calmodulin-dependent histone IIAS phosphorylation (B and D). The assays were carried out in the presence of 2.5 mM EGTA (−Ca), 0.5 mM $CaCl_2$ (+Ca) or 0.5 mM $CaCl_2$ and 1 μM calmodulin (+Ca/CaM).

To verify that the EF-hand motifs in the visinin-like domain are responsible for the Ca²⁺-dependent mobility shift, site-directed mutants of the visinin-like domain protein were created. Each of the EF-hands (I, II, and III) were mutated by replacing the amino acid residue at the −x position (D417 to A, S453 to A, and T495 to A) in the EF-hands (FIG. 14A), which are known to be primary determinants of the Ca²⁺ dissociation rate (Renner et al., *J. Biol. Chem.* 90:6493–6497, 1993). A mutant in which all three EF-hands are mutated was expressed in *E. coli*, purified, and analyzed by SDS-PAGE in the presence of Ca²⁺. The visinin-like protein mutated in the EF hand I migrated at a similar position to the native protein, suggesting that this site may not be functional. However, mutations in EF-hands II and III shifted the mobility of the protein toward the higher molecular weight. The mutant of the EF-hand III migrated to a similar position to the protein in which all three EF hands are mutated (FIG. 14B). The migration of EF-hand III mutant in the presence of Ca²⁺ was also similar to the native protein in the absence of Ca²⁺. These results suggest that Ca²⁺ binding to the EF-hands II and III contribute to the Ca²⁺-dependent mobility shift of the visinin-like domain protein. Removal of Ca²⁺ by EGTA causes the mobility of all the mutant proteins to shift upward to similar higher molecular weight positions. To study the role of the visinin-like domain in Ca²⁺-stimulated autophosphorylation, CCaMK mutant 1-356, which lacks the visinin-like domain, was used for autophosphorylation and substrate phosphorylation studies. Autophosphorylation of mutant 1-356 was not stimulated by Ca²⁺ (FIGS. 15A and 15C), but retained Ca²⁺/calmodulin-dependent kinase activity at a substantially reduced level (FIGS. 15B and 15D). This result indicates that the visinin-like domain is required for Ca²⁺-stimulated autophosphorylation as well as for maximal substrate phosphorylation.

Figure 16A:
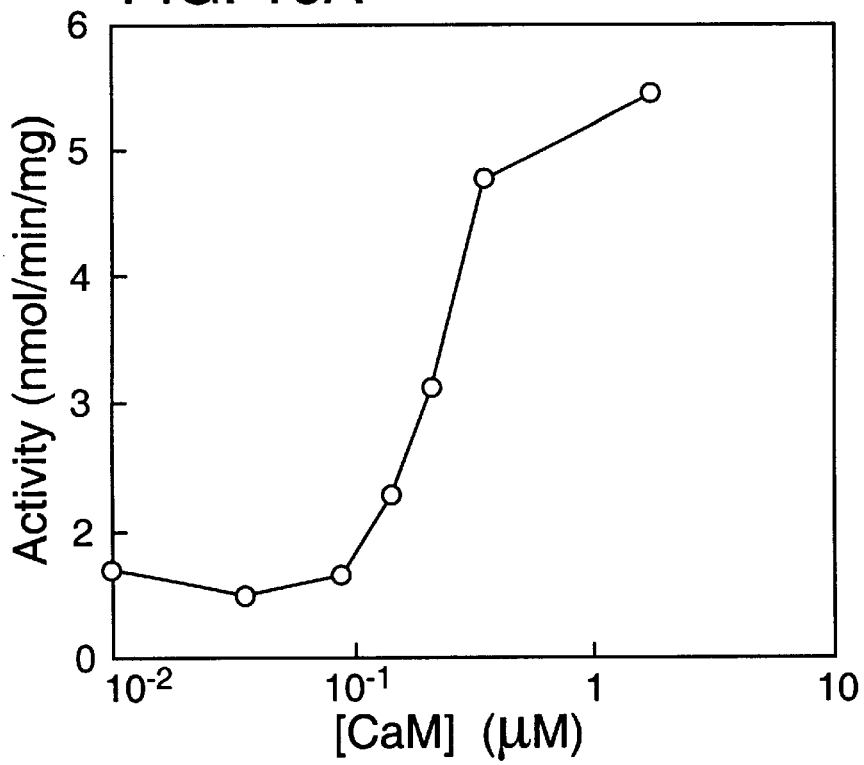
FIG. 16A shows the effect of increasing concentrations of calmodulin on the GS peptide phosphorylation by autophosphorylated lily CCaMK.

The significance of Ca²⁺-stimulated autophosphorylation on substrate phosphorylation by CCaMK was studied using histone IIAS and GS peptide as substrates. In the presence of histone IIAS, calmodulin did not suppress the Ca²⁺-dependent autophosphorylation of CCaMK, probably due to interaction of histone IIAS with acidic proteins such as calmodulin and the visinin-like domain of CCaMK. FIG. 16A shows the effect of increasing concentrations of calmodulin on the GS peptide phosphorylation by autophosphorylated CCaMK. The rate of phosphorylation of the GS peptide by unphosphorylated CCaMK was stimulated by increasing concentrations of calmodulin, but the maximal stimulation was only 3- to 4-fold as compared to the basal activity. However, when autophosphorylated CCaMK was used, calmodulin stimulated the rate of phosphorylation of the GS peptide with kinetics similar to histone IIAS (FIG. 16A).

Figure 16B:
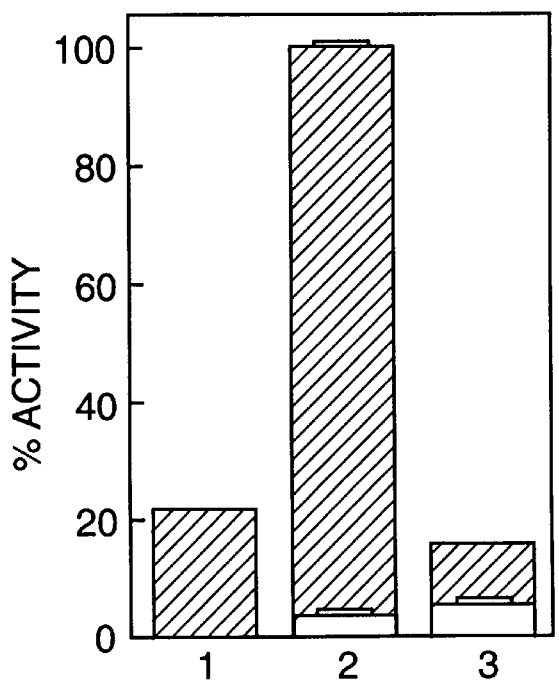
FIG. 16B shows the effect of CCaMK autophosphorylation on $Ca^{2+}$/calmodulin-dependent and calmodulin-independent activity. Column 1, CCaMK autophosphorylated in the presence of 0.5 mM $CaCl_2$ and used for $Ca^{2+}$/calmodulin-dependent GS peptide phosphorylation (hatched bar). Column 2, unphosphorylated enzyme used for $Ca^{2+}$/calmodulind-ependent GS peptide phosphorylation (hatched bar). Solid bars represent the activity of autophosphorylated CCaMK (column 1) and unphosphorylated CCaMK (column 2) in the presence of 2.5 mM EGTA.

To study the effect of autophosphorylation on kinase activity, the Ca²⁺/calmodulin-dependent and Ca²⁺/calmodulin-independent activities of autophosphorylated and unphosphorylated CCaMKs were compared using GS peptide as substrate. Autophosphorylated CCaMK exhibited approximately five-fold greater Ca²⁺/calmodulin-dependent kinase activity than unphosphorylated CCaMK. The maximal stimulation of autophosphorylated CCaMK by Ca²⁺/calmodulin was 20-fold to 25-fold compared to the EGTA control (FIG. 16B). Ca²⁺/calmodulin-independent activity was not significantly affected by autophosphorylation. These results show that Ca²⁺-induced autophosphorylation stimulates Ca²⁺/calmodulin dependent activity of CCaMK.

Figure 17A:
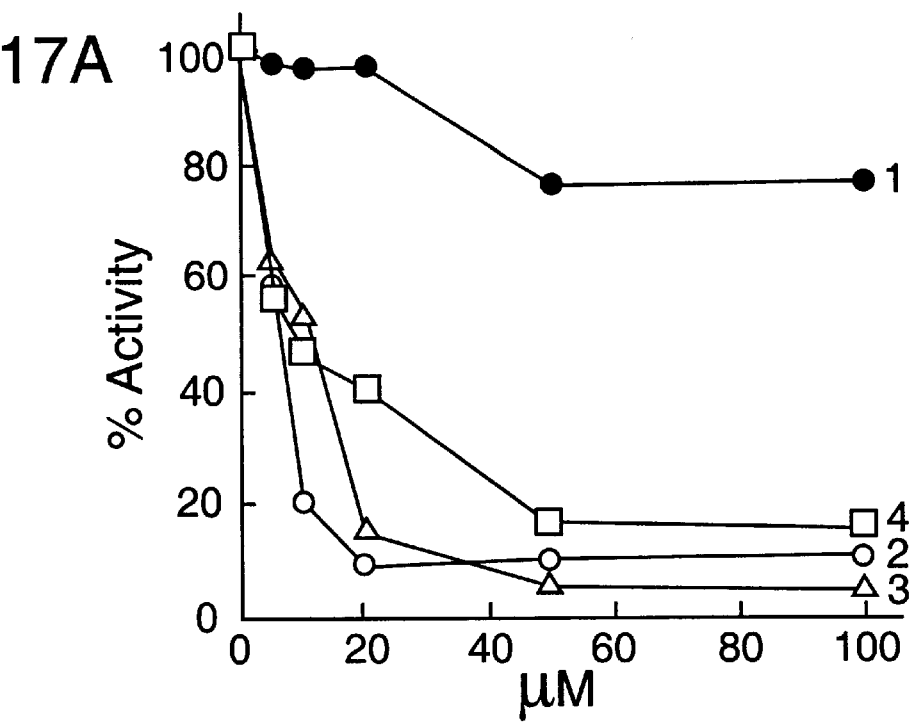
FIG. 17 shows the effects of increasing amounts of synthetic peptides derived from the CCaMK autoinhibitory domain (peptides 1–4: amino acid residues 328–340, 322–340, 317–340, and 311–340 of SEQ ID NO:1, respectively) on the activity of the constitutive mutant denoted 1-322.
Figure 17B:
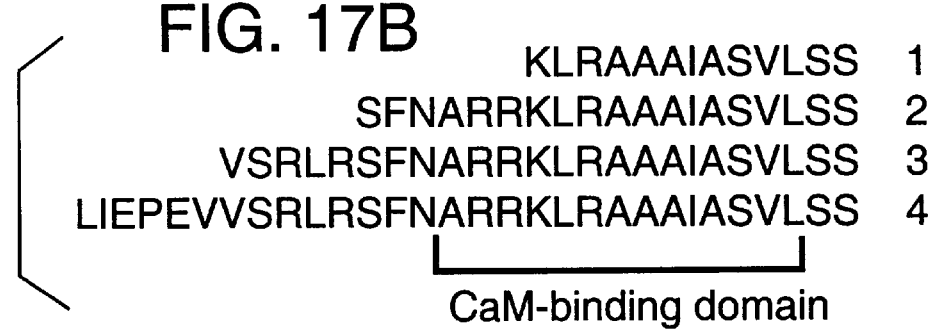
Figure 18A:
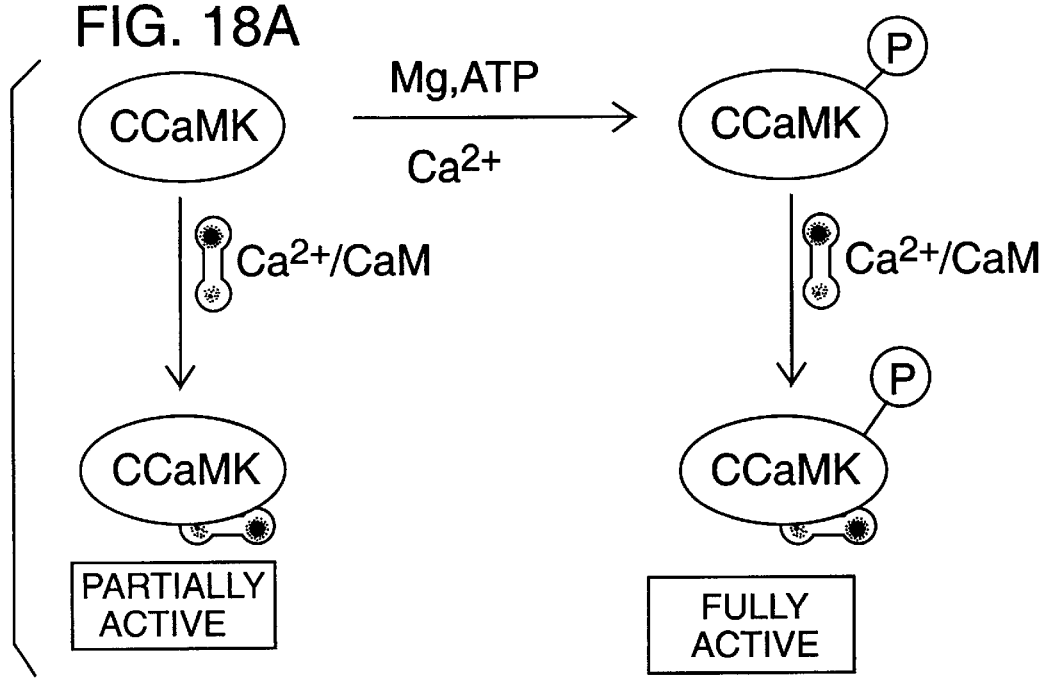
FIGS. 18A–18B shows models describing the regulation of CCaMK by $Ca^{2+}$ and $Ca^{2+}$/calmodulin (A) and the autoinhibitory domain (B).
Figure 18B:
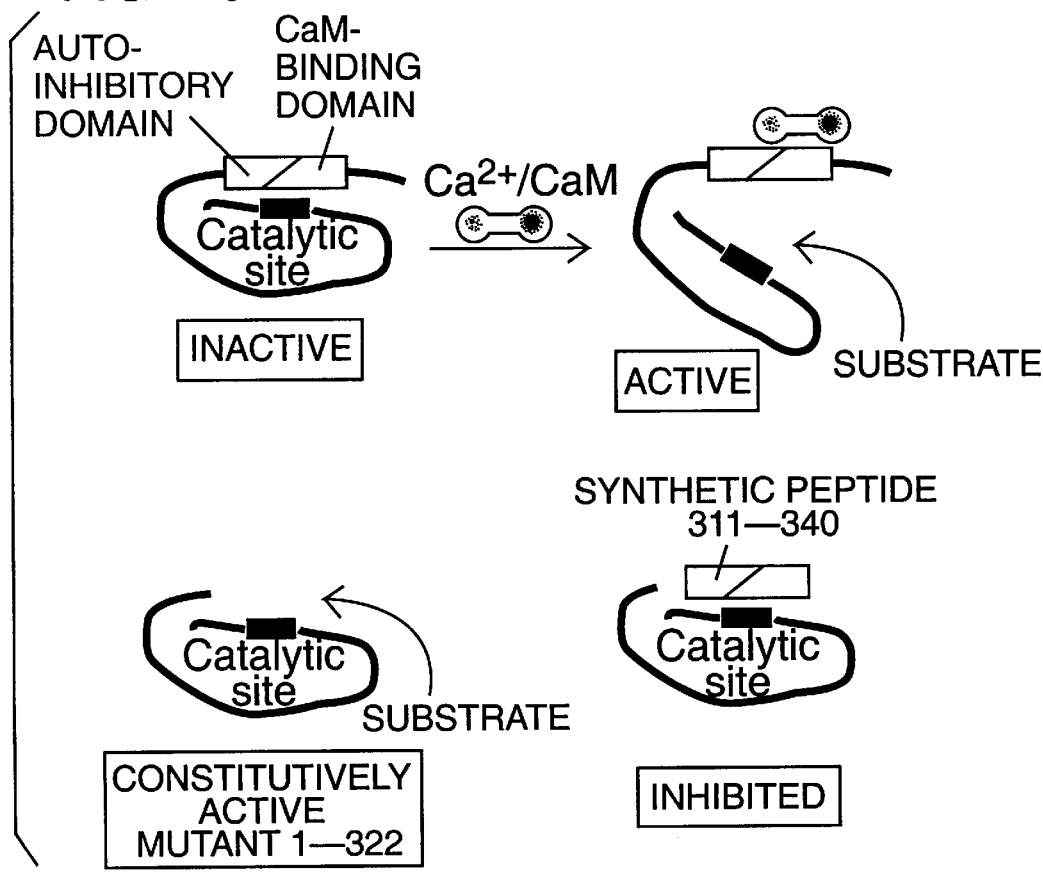

A deletion mutant (denoted 1-322) lacking both calmodulin-binding and visinin-like domains showed constitutive activity (Ca²⁺/calmodulin-independent), suggesting the presence of an autoinhibitory domain. Synthetic peptides derived from the putative autoinhibitory domain (amino acid residues 311–340 of SEQ ID NO:1) inhibited the activity of the constitutive mutant 1-322 (FIG. 17). Models describing the regulation of CCaMK by Ca²⁺ and Ca²⁺/calmodulin and the autoinhibitory domain are shown in FIG. 18. The autoinhibitory domain of CCaMK has similarity to the autoinhibitory domain of mammalian calmodulin kinase II (CaMKII) (Brickey et al., *J. Biol. Chem.* 269:29047–29054, 1994).

Discussion

These studies provide biochemical evidence for a Ca²⁺/calmodulin-dependent protein kinase in plants. Although several Ca²⁺/calmodulin-dependent kinases have been characterized from animal systems (Nairn and Picciotto, *Semin. Cancer Biol.* 5:295–303, 1994), CCaMK is the only plant kinase whose activity is regulated by both Ca²⁺ and Ca²⁺/calmodulin. Among the substrates tested, histone IIAS and synthetic GS peptide are the most efficient phosphate acceptors. CCaMK exhibits a higher Ka value (150–200 nM) for calmodulin (FIGS. 7A and 16A) compared to CaMKII (20–100 nM) (Schulman, *Adv. Second Messenger Phosphoprotein Res.* 22:39–112, 1988) and CaMKIV (26–150 nM) (Kameshita and Fujisawa, *J. Biochem.* (Tokyo) 113:583–590, 1993; Enslen et al., *J. Biol. Chem.* 269:15520–15527, 1994), indicating that plant kinase requires a higher concentration of calmodulin for its activity. This is probably due to a higher dissociation constant of calmodulin for CCaMK (55 nM) than for animal Ca²⁺/calmodulin-dependent protein kinases (1–10 nM) (Sikela and Hahn, *Proc. Natl. Acad. Sci. USA* 84:3038–3042, 1987). ³⁵S-labeled calmodulin binding and peptide binding assays revealed that the calmodulin-binding site of CCaMK is present between amino acid residues 322–340 of SEQ ID NO:1 (FIG. 9). This region has homology to animal CaMKII, with conserved basic (Arg-325, Arg-326, and Lys-327) as well as hydrophobic (Phe-323, Ala-325, Ala-332, and Leu-338) amino acid residues.

The visinin-like Ca²⁺-binding domain, a novel feature of CCaMK, is not known to exist in other protein kinases. The visinin-like domain contains three EF-hand motifs (FIG. 14A) similar to animal visinin-like proteins. Frequenin, neurocalcin, and visinin-like proteins are known to be members of Ca²⁺-sensitive guanylyl cyclase activators that are involved in cation channel regulation in neuronal tissues (Palczewski et al., *Neuron* 13:395–404, 1994). Visinin-like proteins typically contain three conserved EF-hand motifs, each with a different affinity for Ca²⁺ (Pongs et al., *Neuron*

11:15–28, 1993; Ames et al., *J. Biol. Chem.* 270:4526–4533, 1995). The $Ca^{2+}$-dependent mobility-shift assay suggests that binding of $Ca^{2+}$ to the EF-hands II and III is important for inducing conformational changes in the visinin-like domain of CCaMK (FIG. 14B). $Ca^{2+}$-induced conformational change in the visinin-like domain may be critical for regulation of CCaMK activity. The CCaMK mutant 1-356 lacking this domain did not show $Ca^{2+}$-dependent autophosphorylation. The mutant 1-356 also exhibited reduced activity as compared to the native enzyme, suggesting that the visinin-like domain is required for the maximal activation of CCaMK. It is unlikely that this reduced activity is due to lowered affinity of mutant 1-356 to calmodulin, since the saturation curve of $^{35}$S-calmodulin binding for mutant 1-356 indicated that it has a similar Kd (60 nM) for calmodulin. However, it is possible that the visinin-like domain may stabilize the conformation of CCaMK, which is indispensable for its maximal activity.

Figure 13B:
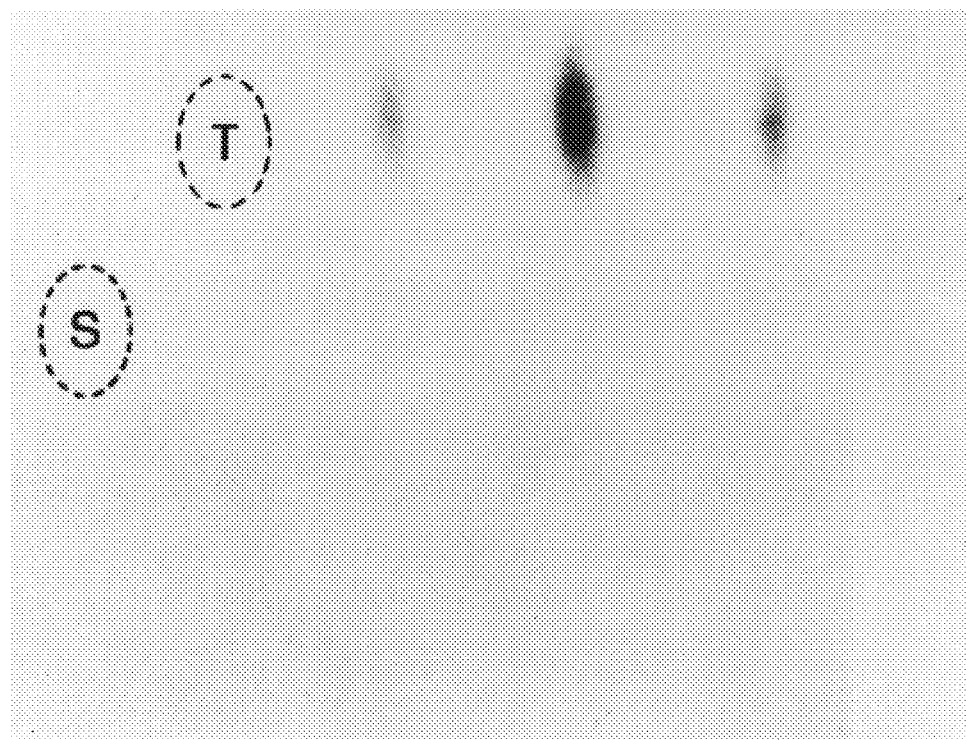
FIG. 13B shows phosphoamino acid analysis of autophosphorylated lily CCaMK (200 ng) either in the presence of 2.5 mM EGTA (−Ca), 0.5 mM $CaCl_2$ (+Ca), or 0.5 mM $CaCl_2$ plus 1 µM calmodulin (+Ca/CaM). The positions of phosphoserine (S) and phosphothreonine (T) are marked.

Phosphoamino acid analysis revealed that CCaMK autophosphorylatiothreonine the phosphorylation of the threonine residue(s) (FIG. 13B). Autophosphorylation of CCaMK increased its $Ca^{2+}$/calmodulin-dependent kinase activity by five-fold (FIG. 16B). $Ca^{2+}$/calmodulin-dependent autophosphorylation of animal CaMKII at Thr-286 $NH_2$-terminal to the calmodulin-binding site, is known to stimulate $Ca^{2+}$-independent activity (Colbran and Soderling, *Curr. Topics Cell. Regul.* 31:181–221, 1990; Theil et al., *Proc. Natl. Acad. Sci. USA* 85:6337–6341, 1988; Fong et al., *J. Biol. Chem.* 264:16759–16763, 1989). In contrast, $Ca^{2+}$/calmodulin-independent basal autophosphorylation at Thr-305 and 306 within the calmodulin-binding site inactivates CaMKII by inhibiting its ability to bind calmodulin (Leckteig et al., *J. Biol. Chem.* 263:19232–19239, 1988; Colbran, *J. Biol. Chem.* 268:7163–7170, 1993). Although the calmodulin binding region of CCaMK has similarity to the calmodulin-binding region of CaMKII, there are no threonine residues around this area (FIG. 9A). The inhibition of the $Ca^{2+}$-stimulated CCaMK autophosphorylation by calmodulin, may be due to the conformational change induced by the calmodulin binding to CCaMK (James et al., *Trends Biochem. Sci.* 20:38–42, 1995). Inhibition of autophosphorylation by calmodulin is also reported in smooth muscle MLCK (Tokui et al., *Biochemistry* 34:5173–5179, 1995), in which all three phosphorylated residues are present in proximity to the calmodulin-binding site. The absence of threonine residues around the calmodulin-binding region of CCaMK suggests that the mechanism of CCaMK regulation by autophosphorylation is different from MLCK and CaMKII.

Signal-induced changes in cytosolic $Ca^{2+}$ concentration are believed to be important for many cellular processes in plants (Gilroy and Trewavas, *Trends Genetics* 16:677–682, 1994; Bush, *Plant Physiol.* 103:7–13, 1993; Gilroy et al., *J. Cell. Sci.* 106:453–462, 1993). $Ca^{2+}$ has a dual effect on the stimulation of CCaMK activity. In the presence of calmodulin, $Ca^{2+}$ binds to calmodulin and stimulates CCaMK activity. In the absence of calmodulin, $Ca^{2+}$ alone stimulates autophosphorylation of CCaMK which further increases $Ca^{2+}$/calmodulin-dependent kinase activity (FIG. 16B).

Plants have multiple isoforms of calmodulin and their expression is developmentally regulated and responsive to environmental signals (Takezawa et al. *Plant Mol. Biol.* 27:693–703, 1995; Jena et al., *Proc. Natl. Acad. Sci. USA* 86:3644–3648, 1989; Braam and Davis, *Cell* 60:357–364, 1990). Plant calmodulin mRNA and protein are also reported to have a relatively rapid turnover rate in the cell (Perera and Zielinski, *Plant Physiol.* 100:812–819, 1992). Signal-induced expression and rapid turnover suggest that there is a dynamic regulation of calmodulin in vivo. Therefore, it is likely that CCaMK activity is differentially controlled by signal-induced transient changes in free $Ca^{2+}$ concentration and calmodulin. In plant cells, the $Ca^{2+}$ concentration required for $Ca^{2+}$-dependent autophosphorylation and the $Ca^{2+}$ concentration required for $Ca^{2+}$/calmodulin-dependent substrate phosphorylation may be different.

Example 3

Effects of CCaMK on Male Sterility

Materials and Methods

Plant Material. Tobacco (*Nicotiana tabacum* cv. Xanthi) and lily (*Lilium longiflorum* Thumb cv. Nellie White) plants were grown under normal greenhouse conditions.

In situ Hybridization. Different stages of lily anthers were cut and fixed overnight at 4° C. in a solution containing 25% paraformaldehyde, 1.25% glutaraldehyde, 50 mM Pipes (pH 7.2). The samples were processed and embedded in LR white. One $\mu$m-thick cross-sections were mounted on gelatin-coated slides, stained with safranin, and examined by light microscopy.

To obtain a CCaMK-specific probe, a 438-bp fragment (base pairs 2076 to 2514 in lily CCaMK[SEQ ID NO:1]; Patil et al., *Proc. Natl. Acad. Sci. USA* 92:4897–4901, 1995) was cloned into the pSPT18 plasmid (Boehringer Mannheim, DIG RNA Labeling Kit, cat. no. 1175025). Antisense and sense digoxigenin-labeled RNA was synthesized according to standard protocols (Boehringer Mannheim). After transcription, the RNA was hydrolyzed to approximately 150 bp by 0.2M $NaHCO_3/Na_2CO_3$ (pH 10.2) at 60° C.

Sections were treated with 5 $\mu$g/mL proteinase K for 30 min at 37° C. before hybridization. 15 $\mu$L hybridization solution (Panoskaltsis-Mortair et al., *BioTechniques* 18:300–307, 1995) containing the heat-denatured RNA probe were applied to each section, covered with a coverslip, sealed with rubber cement, and incubated in a humid chamber overnight at 48° C. The next day, the slides were washed in 2×SSC at room temperature for 5 min, then incubated in RNase A (40 $\mu$g/ml in STE) for 30 min at 37° C., washed with 2×SSC, 50% formamide at 50° C. for 5 min, with 1×SSC, 0.5×SSC, and 0.2×SSC at room temperature for 5 min each wash, then quickly rinsed with $H_2O$. Signals were detected by immunolocalization (Li et al., *Cell* 72:869–879, 1993) using gold-conjugated sheep anti-digoxigenin, silver enhanced at room temperature for 18 min, then stained with safranin for 30 sec.

Protein Extraction. Anther tissue was frozen in liquid nitrogen and ground using a mortar and pestle, then taken into 4 to 5 volumes (w/v) of extraction buffer (40 mM Tris pH 7.6, 1 mM DTT, 1 mM EDTA, 0.1% Triton X-100, 1 mM PMSF and 10 $\mu$g/mL each of antipain, pepstatin, and leupeptin). Powdered tissue was vortexed in the extraction buffer for 1 min and centrifuged at 12,000 g for 10 min at 4° C. The supernatant was used for phosphorylation assays.

Inactivation of Endogenous Kinases. The total protein extract was heated at 60° C. for 10 min, slowly cooled in water at room temperature, and centrifuged at 10,000 g for 10 min at 4° C. This method inactivates all endogenous kinases in plant extracts.

In vitro Phosphorylation of Proteins. For in vitro phosphorylation, 25 $\mu$g of heat inactivated total proteins were used. The assay (50 $\mu$L) was carried out for 10 min at 30° C. in 50 mM Hepes (pH 7.6), 1 mM DTT, 10 mM $Mg(Ac)_2$, 200 mM $\gamma$-$^{32}$P-ATP (1500–2000 cpm/pmol), 0.5 mM CaCl$_2$, 1 μM calmodulin and either with or without CCaMK (200 ng). The reaction was terminated by the addition of SDS-PAGE sample buffer and analyzed by SDS-PAGE using a 10% gel. Proteins were visualized by staining with Coomassie Brilliant Blue. The gels were dried and subjected to autoradiography.

Autophosphorylation of CCaMK. Four μg of CCaMK were autophosphorylated at 30° C. for 20 min in the presence of 50 mM Hepes (pH 7.5) containing 0.5 mM γ-$^{32}$P-ATP (8000–10,000 cpm/pmol), 10 mM Mg(Ac)$_2$, 1 mM DTT. Unincorporated ATP was removed by filtering the reaction mixture several times through a Microcon 10 filter (Amicon).

Gel Overlay Assay of CCaMK-binding Proteins. Protein samples (100 μg) from lily anthers at various stages of development were separated by SDS-PAGE using a 12% gel and transferred to a PVDF membrane (Millipore) at room temperature at 150 V for 3 hrs in transfer buffer (39 mM glycine, 48 mM Tris base, 0.037% SDS and 20% methanol). The gel overlay assay was performed using the method of Carr and Scott (*Trends Biochem. Sci.* 17:246–247, 1992). The membrane was blocked for 60 min in blocking buffer (50 mM Tris HCl/200 mM NaCl-TBS containing Tween 20 (3% v/v) and non-fat powdered milk (5% w/v)).

After washing the membrane with rinsing buffer (TBS containing Tween 20 (0.1% v/v) and non-fat powdered milk (5% w/v)) for 30 min, the membrane was incubated with autophosphorylated CCaMK ($^{32}$P-labeled) in rinse buffer for 2 hrs at room temperature with constant agitation. The membrane was washed extensively with a minimum of 4 to 5 changes of rinse buffer, dried, and subjected to autoradiography.

PCR. cDNA Library Screening, and Sequencing. A partial CCaMK cDNA clone (483 bp) was obtained from developing anthers of tobacco (*Nicotiana tabacum* SR1) by PCR using two degenerate oligonucleotide primers corresponding to two highly conserved regions of mammalian Ca$^{2+}$/calmodulin-dependent protein kinases (DLKPEN and FNARRKL [SEQ ID NO:12 and SEQ ID NO:13, respectively], Hanks et al., *Science* 241:42–52, 1988). A tobacco immature anther cDNA library was produced using the λ ZAPII vector according to manufacturer's protocol (Stratagene) and screened using the PCR-amplified fragment as a probe. The sequencing of the cDNA was carried out by using the dideoxynucleotide chain-termination method.

RT-PCR Analysis. First-strand cDNA was synthesized from 5 μg total RNA using a cDNA synthesis kit (Gibco BRL) and one out of 20 μL was used as template. Two tobacco CCaMK gene-specific oligonucleotide primers (3'-coding region, amino acid residues 290–296 and 512–518) and two calmodulin degenerate primers (Takezawa et al., *Plant Mol. Biol.* 27:693–703, 1995) were used in the same reaction. The cycling profile was 25 cycles of 94° C. for 30 sec, 50° C. for 1 min, and 72° C. for 1 min.

Southern Blot Analysis. Tobacco genomic DNA (5 μg) was digested with various restriction enzymes and transferred to a nylon membrane. Hybridization was by standard protocols (Sambrook et al., 1989). The membrane was washed twice in 2×SSC, 0.5% SDS at room temperature for 15 min and twice in 0.1×SSC, 0.1% SDS at 65° C., 20 min.

Plant Transformation. Binary plasmid pGA748 (An, *Meth. Enzymol.* 153:292–305, 1987) was used in preparing the sense and antisense constructs. To produce a sense construct, full-length cDNA (SEQ ID N:10) was used; to produce an antisense construct, a BamHI cut fragment (amino acid residues 110–517) was used. The two constructs were then transferred to A. tumefaciens strain LBA4404 using a direct DNA transfer method (An, *Meth. Enzymol.* 153:292–305, 1987). Leaf discs of N. tabacum xanthi were transformed according to the method of Horsch (*Science* 227:1229–1231, 1985). Transformants were selected on media containing kanamycin (100 mg/L).

Slot-Blot Analysis. Different tobacco parts and tobacco anthers from different stages were collected and the RNA was isolated as described by Verwoerd (*Nucl. Acids Res.* 17:2362, 1989). Slot blot analysis was performed by using 5 μg total RNA from different tobacco parts or anthers from different stages. A 330-bp fragment (5' coding region, amino acid residues 1-109, FIG. 11) was used as a probe. Hybridization was performed at 42° C. overnight in a solution containing 50% formamide, 6×SSPE, 5×Denhardt's solution, 0.5% SDS, 100 μg/mL denatured herring sperm DNA and >10$^9$ cpm/μg of $^{32}$P-labeled cDNA probe. The membrane was washed once in 2×SSC, 0.5% SDS at room temperature for 15 min and two times for 10 min each in 0.2×SSC, 0.1% SDS at 55° C., and exposed to film. After the film was exposed, the membrane was washed in 0.1×SSC, 0.1% SDS at 90° C. for 5 min to remove the probe, then re-hybridized to $^{32}$P-labeled PCM6 calmodulin cDNA, which shows the least changes during development (Takezawa et al., *Plant Mol. Biol.* 27:693–703, 1995) to confirm that the loaded RNA was the same amount.

Scanning Electron Microscopy. Pollen grains from mature anthers were collected, freeze-dried, coated with gold and observed under a scanning electron microscope at 15 KV or 20 KV.

Histochemical Localization of Callose. Dehisced tobacco pollen grains were tapped directly into a 0.01% aqueous solution of water-soluble aniline blue made up in 0.15M K$_2$HPO$_4$. After 30 min, samples were observed using a microscope fitted with a fluorescence attachment as described by Worrall et al. (*Plant Cell* 4:759–771, 1992).

Pollen Germination. Dehisced tobacco pollen grains were collected and incubated at room temperature in a medium containing 10% sucrose, 0.0017 g/L KH$_2$PO$_4$, 0.025 g/L H$_3$BO$_3$, and 10 mM CaCl$_2$. After 2 hrs incubation, the pollen suspension was mixed with diphenylboric acid 2-aminoethyl ester (0.5% in 50% MeOH, Sigma) and photographed.

Cross Pollination. Anthers in antisense plants were removed before they matured, pollen grains from dehisced wild-type anthers were collected and applied to pistils of antisense plants.

Results

Figure 19:
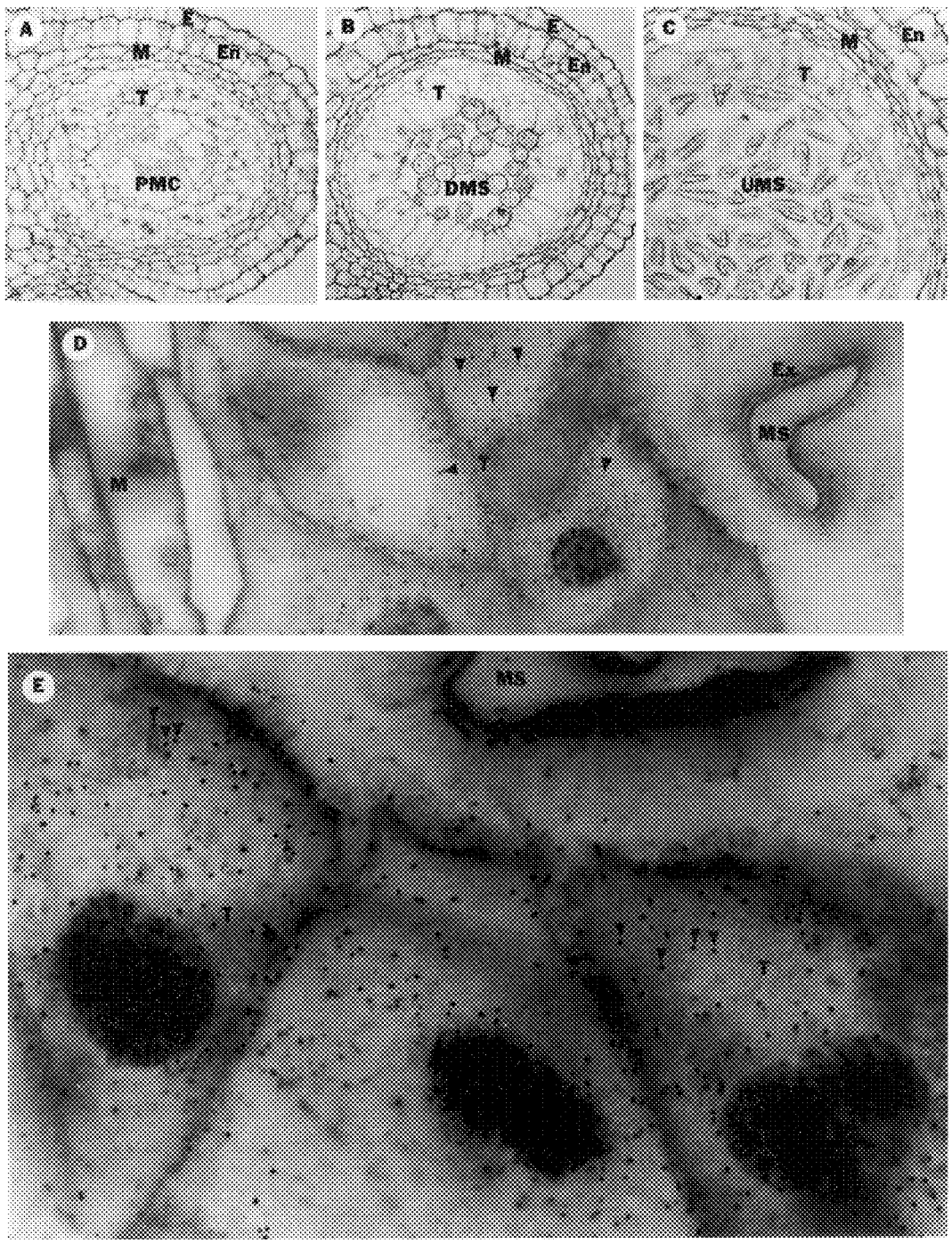
FIGS. 19A–19C show cross-sections of lily anthers demonstrating progressive development of tapetal cells and microspores. A. Pollen mother cell stage (2.0 cm bud), 97×. B. Meiosis stage I (2.5 cm bud), 97×. C. Uninucleate microspore stage (3.5 cm bud), 97×. Abbreviations: E, epidermis; En, endothecium; M, middle layers; PMC, pollen mother cells; DMS, dividing microspores; UMS, uninucleate microspores; T. tapetal cells.
FIGS. 19D–19E show the results of in situ hybridization showing localization of CCaMK in tapetal cells. Abbreviations: Exine (Ex), microspore (MS) (3.5 cm bud). Magnification: 19D, 865×; 19E, 1600×. Arrows indicate hybridization signals.

CCaMK is Expressed in Anther in a Stage-specific Manner. Micrographs in FIGS. 19A–C show the progressive development of microspores in lily anther. FIG. 19A shows the pollen mother cells (bud size 2.0 cm), FIG. 19B shows stage I of meiosis (bud size 2.5 cm), and FIG. 19C shows the uninucleate microspores (bud size 3.5 cm). In order to investigate the cellular localization of CCaMK, in situ hybridization experiments were performed. Thin sections of developing lily anthers were hybridized with an antisense or sense CCaMK RNA probe labeled with digoxigenin and detected by gold-conjugated sheep anti-digoxigenin. The antisense probe yielded hybridization signals mostly in tapetum and locules when the bud was 2.5 to 3.5 cm (FIGS. 19D and 19E). In contrast, epidermis, endothecium and middle layers showed little or no expression, while the sense control did not show hybridization in any tissues. Expression of CCaMK was specific to stages that coincided with meiosis and the uninucleate microspore stage (FIGS. 19B and 19C).

Figure 20:
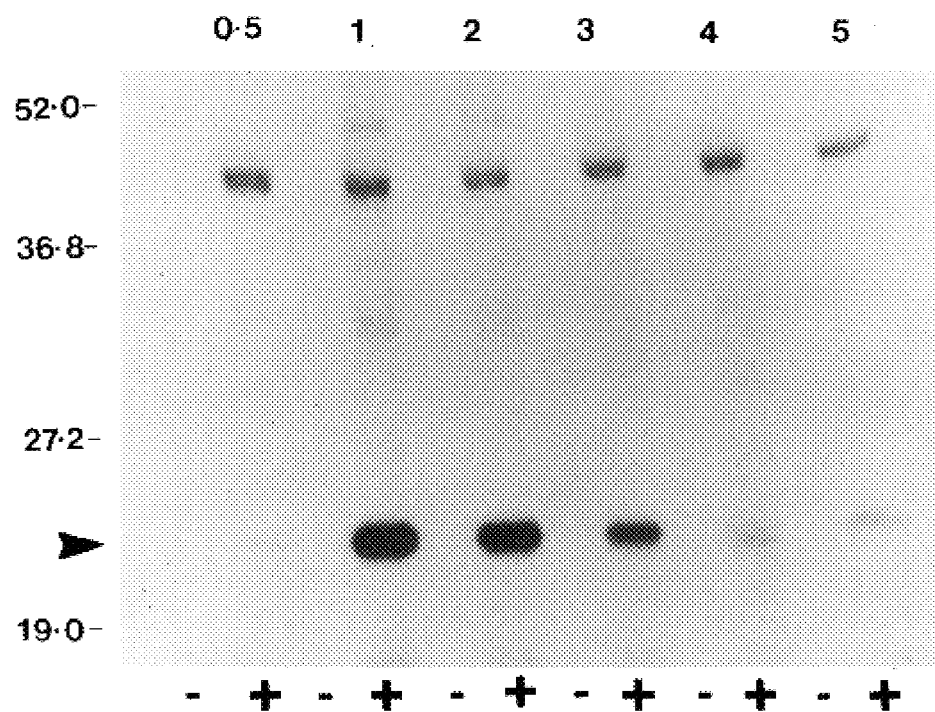
FIG. 20 shows $Ca^{2+}$/calmodulin-dependent phosphorylation of heat-inactivated lily anther proteins in the presence (+) or absence of CCaMK (−) at different stages of development. Numbers on top indicate the sizes of flower buds in cm from which the anthers were used for protein extraction. Molecular weight markers (kDa) are indicated on the left. Arrow indicates 24 kDa protein showing high levels of phosphorylation when buds are 1.0–3.0 cm.

Identification of CCaMK Substrates in Lily Anthers. In order to identify substrates for CCaMK, total protein isolated from various stages of developing lily anthers was heated to inactivate endogenous kinases and subjected to $Ca^{2+}$/calmodulin-dependent phosphorylation in the presence or absence of E. coli-expressed and purified CCaMK. The proteins were then separated on a 10% SDS-polyacrylamide gel and the gel was dried was subjected to autoradiography. Several endogenous proteins were phosphorylated in a $Ca^{2+}$/calmodulin-dependent manner by CCaMK (FIG. 20). These proteins were shown to be present when the buds were 1.0 to 3.0 cm (fully opened lily flower is about 15 cm), coinciding with the pollen mother cell stage to the uninucleate microspore stages of lily anther development. The amount of these substrate proteins decreased in later stages of anther development and were absent in fully mature anthers and other parts of the plant, indicating the anther- and developmental stage-specificity of these substrates.

A polypeptide of approximately 24 kDa that was present at an extremely low level was phosphorylated to a very high level (FIG. 20), indicating its high specificity for CCaMK. The phosphorylation of this 24-kDa protein is $Ca^{2+}$/calmodulin-dependent, since the addition of EGTA, a $Ca^{2+}$ chelator or W-7 (Sigma), a calmodulin inhibitor, prevented its phosphorylation by CCaMK.

Figure 21:
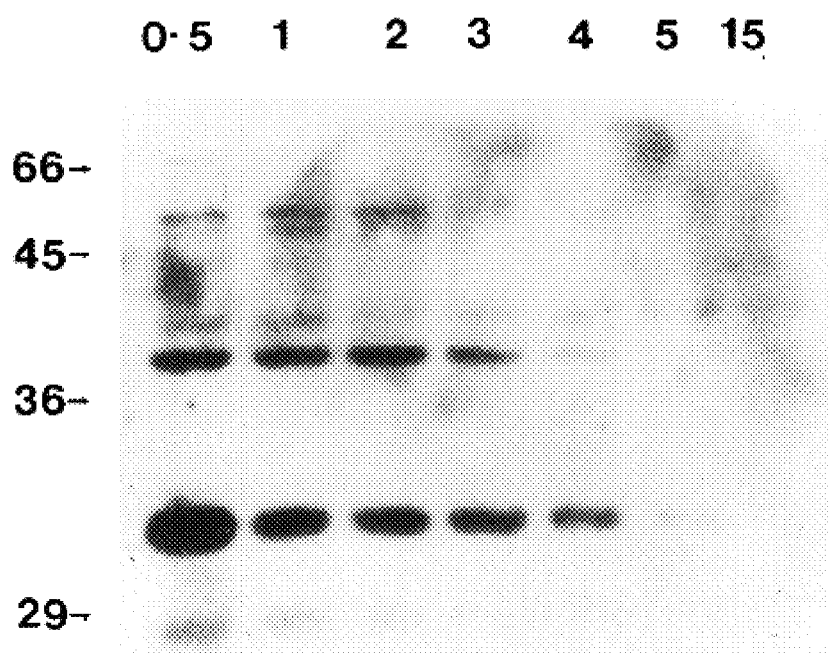
FIG. 21 shows the expression pattern of CCaMK-binding proteins at different stages of lily anther development. The numbers indicate the sizes of flower buds in cm from which the anthers were used for protein extraction. Molecular weight markers (kDa) are indicated on the left.

Binding Proteins of CCaMK. Autophosphorylated CCaMK ($^{32}$P-labeled) was used in a gel overlay assay to identify the proteins interacting with CCaMK. Total protein (100 μg) from various stages of lily anthers and other parts of the plant were separated on SDS-PAGE, transferred to a PVDF membrane, and probed with autophosphorylated CCaMK ($^{32}$P-labeled) CCaMK. The dried membrane was then subjected to autoradiography. As shown in FIG. 21, several proteins that bind specifically to CCaMK were present only when the bud size was between 0.5 cm to 3.0 cm, coinciding with the pollen mother cell stage to the uninucleate microspore stage. There was a progressive decrease in binding proteins at later stages of anther development and a total absence in fully mature anthers. These proteins were not detected in other parts of the plant. These results indicate that CCaMK bids various proteins in developing anthers in an anther- and stage-specific manner.

Cloning and Sequence Analysis of a Tobacco CCaMK cDNA. A full-length (1776 bp including a 55-bp poly-A sequence (after "1776 bp")) cDNA clone from tobacco (Nicotiana tabacum SRI) was obtained by screening an immature tobacco anther cDNA library using a PCR-amplified fragment (483 bp, corresponding to amino acid residues 164–325) as a probe. The nucleotide sequence of tobacco CCaMK cDNA is shown in FIG. 22 (SEQ ID NO:10).

The coding region of the tobacco CCaMK cDNA encodes a 517 amino acid polypeptide and is flanked by a 19 bp 5'-untranslated region and a 203 bp 3'-untranslated region. FIG. 23A shows the comparison of amino acid sequences of tobacco and lily CCaMKs. Both tobacco and lily CCaMKs contain all 11 major conserved subdomains of serine/threonine protein kinases (Hanks et al., Science 241:42–52, 1988), the calmodulin-binding domain and the visinin-like $Ca^{2+}$-binding domain (FIGS. 23A and 23B). Tobacco CCaMK and lily CCaMK share 71% identity and 82% similarity, with 66% identity and 79% similarity in the kinase domain (amino acid residues 1-307). The 3' visinin-like domain (amino acid residues 339–517) is highly conserved, sharing 79% identity and 87% similarity, suggesting that the visinin-like domain is functionally conserved and plays an important role in regulating CCaMK activity. The calmodulin-binding domain (amino acid residues 320 to 335) is also conserved.

The helical wheel projection of the calmodulinbinding domain of tobacco and lily CCaMKs formed a basic amphipathic α-helix (O'Neill et al., Trends Biochem Sci. 15:59–64, 1990), a characteristic feature of calmodulin-binding sites.

Figure 24:
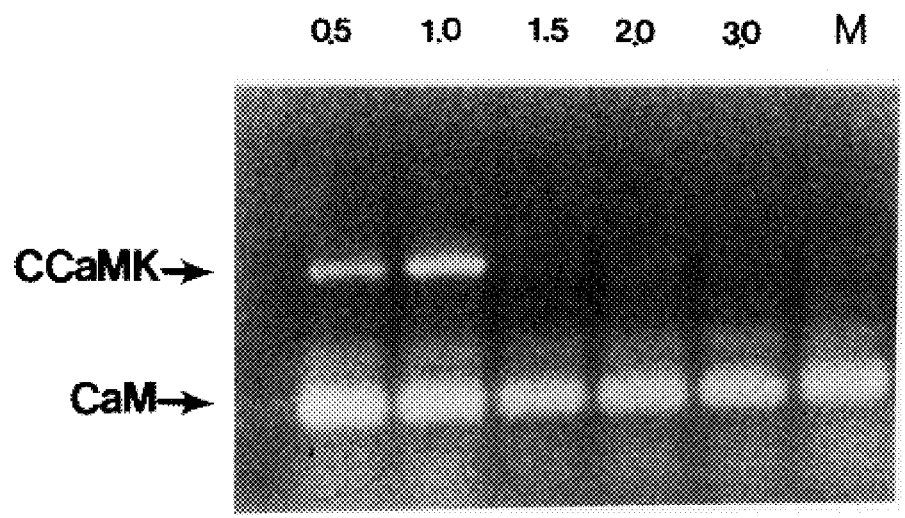
FIG. 24 shows the results of RT-PCR showing the expression pattern of tobacco CCaMK at different stages of anther development. Numbers on top of each lane indicate bud size in cm, "M" indicates mature anther. Lower band in each lane shows calmodulin (CaM) control.

Expression Pattern of CCaMK in Tobacco. As shown in FIG. 24, CCaMK mRNA was detected during meiosis (bud size 0.5–0.8 cm), and peaked following meiosis (bud size about 1.0 cm; when fully opened, the tobacco flower is approximately 4.5 cm). The message became undetectable at later stages of development. The CCaMK gene was preferentially expressed during flower stage 3 to stage 2 of anther development (Koltunow et al., Plant Cell 2:1201–1224, 1990). RNA slot-blot analysis confirmed this result. No expression was detected in other tissues (including leaf, stem, root, pistil, ovary, and petal), indicating that CCaMK is expressed in an anther-specific and stage-specific manner during microsporogenesis.

Figure 25:
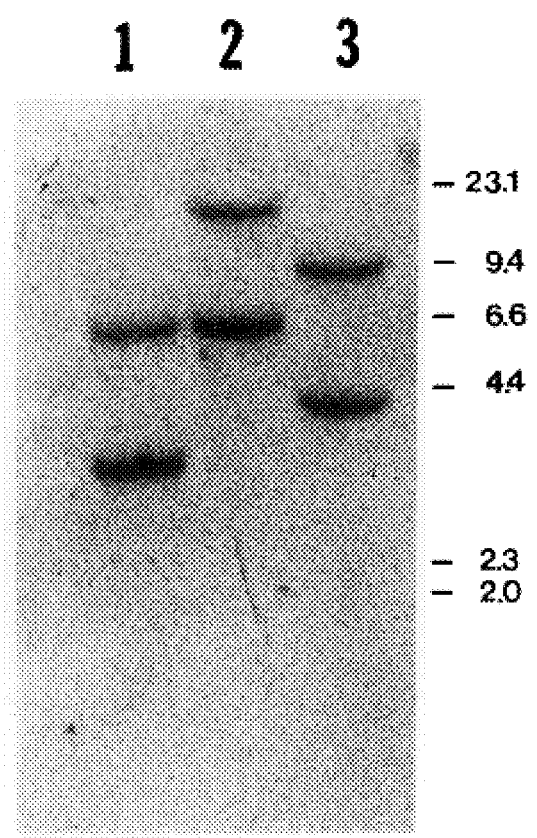
FIG. 25 shows a Southern blot of tobacco genomic DNA digested with various restriction enzymes and probed with CCaMK. Lanes: 1, EcoRI; 2, EcORV; 3, HindIII. Sizes in kb are shown on the right.

Genomic Organization of CCaMK in Tobacco. To determine the approximate copy number of tobacco CCaMK, Southern blot analysis was carried out using a 600-bp fragment (amino acid residues 123–325) as a probe (FIG. 25). Two hybridization bands were observed in tobacco genomic DNA digested with EcoRI, EcoRV and HindIII. Because the tobacco CCaMK cDNA sequence has one internal site for all three restriction enzymes, it is likely that tobacco CCaMK is encoded by a single copy gene.

In order to obtain a tobacco CCaMK genomic clone, a tobacco genomic library (Clontech) was screened with a probe consisting of the 5'-untranslated region of the tobacco CCaMK cDNA. A clone showing positive hybridization under stringent conditions was subcloned and sequenced. FIG. 26 (SEQ ID NO:11) shows the nucleotide sequence of the promoter region of the tobacco CCaMK genomic sequence.

Figure 27:
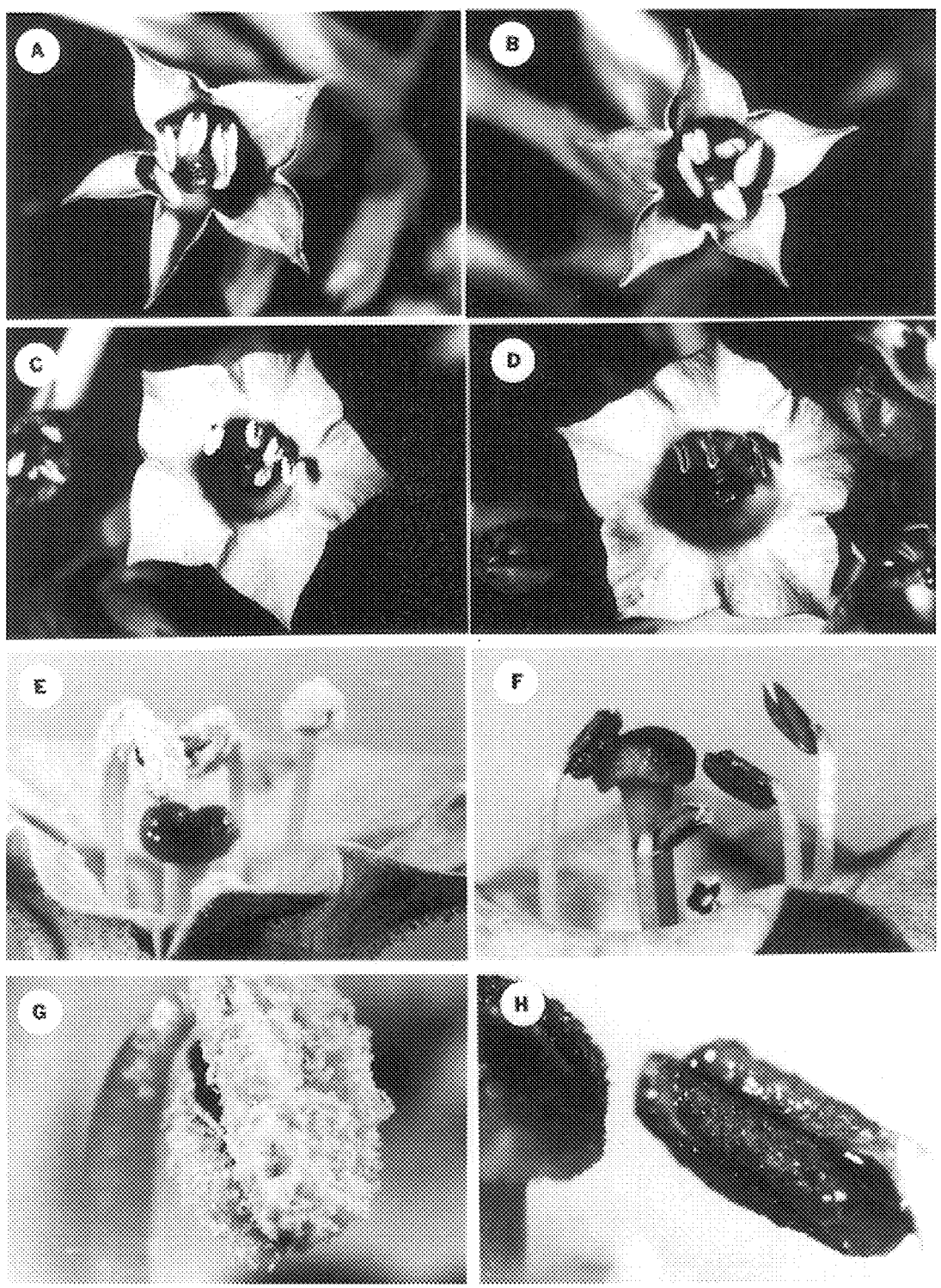
FIGS. 27A–27H show tobacco flowers from wild-type and male sterile antisense plants. A. Wild-type flower before dehiscence. B. Antisense flower before dehiscence. (Note: there are no obvious differences between wild-type and antisense flower prior to dehiscence.) C. Wild-type flower after dehiscence. D. Antisense flower after dehiscence. Note: the wild-type anthers are white and fluffy, while the antisense anthers are bare. E. Enlarged view of the wild-type anther, 5×. F. Enlarged view of antisense anther, 5×. G. Enlarged view of wild-type anther, 20×. H. Enlarged view of antisense anther, 20×.

Plants Carrying CCaMK Antisense Construct Are Male Sterile. To study the function of CCaMK in vivo, sense and antisense constructs of tobacco CCaMK were fused to the CaMV 35S promoter and transgenic tobacco plants were produced. Seventeen antisense and 59 sense kanamycin-resistant transgenic plants were produced. Four of the 17 antisense plants (A3, A4, A14, A17) showed extreme abnormality in anther development. Control plants (transformed with vector pGA748 alone) showed normal development as compared to wild-type untransformed plants. Southern-blot analysis, using a 687-bp fragment of tobacco CCaMK (3' coding region, amino acid residues 289–517) as a probe, revealed that all of the antisense plants were transgenic. The anthers in transgenic plants looked normal until anthesis (FIGS. 27A and 27B). At stage 12 (Koltunow et al., Plant Cell 2:1201–1224, 1990), when the anthers dehisced, wild-type anthers were fluffy with pollen, anthers in A3, A4, A14, and A17 plants were mostly bare (FIGS. 27D, 27F and 27H).

Figure 28:
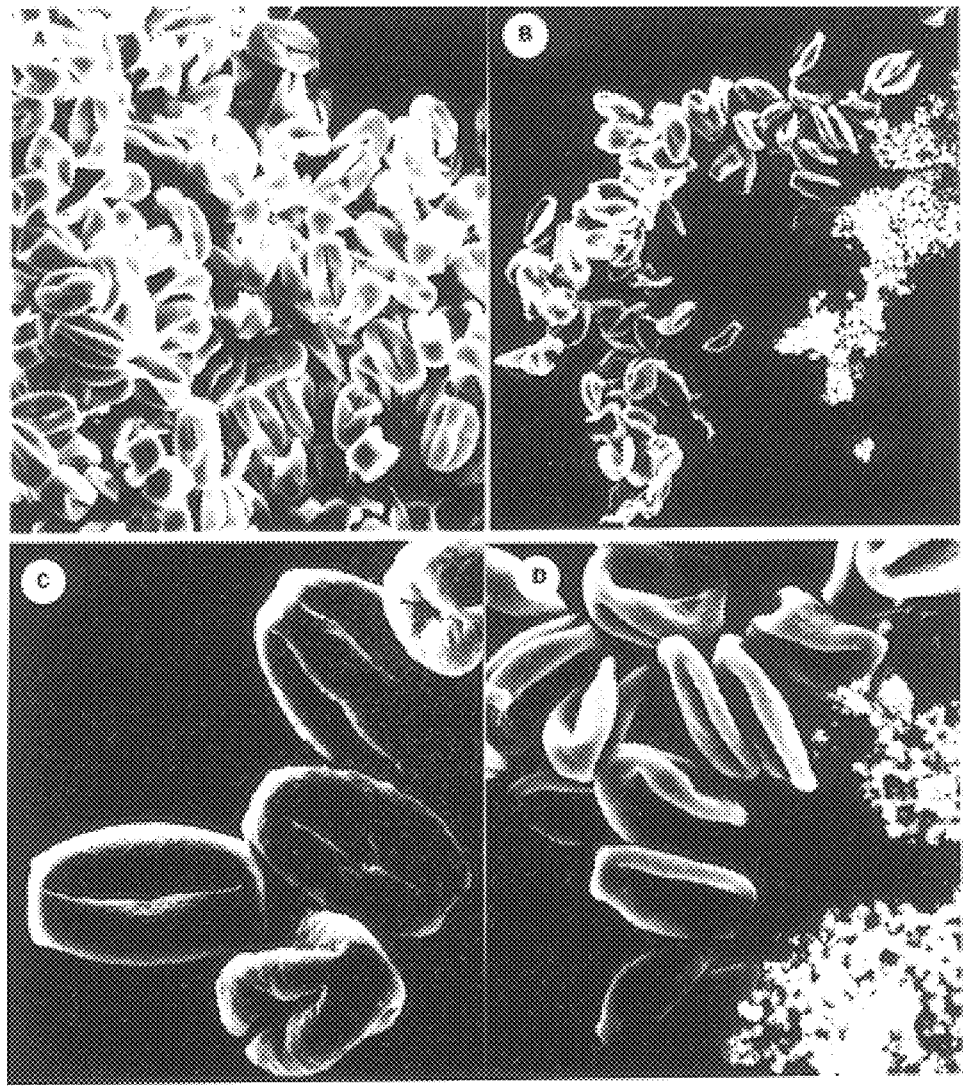
FIGS. 28A–28D show scanning electron micrographs showing wild-type and antisense pollen grains. A. Wild-type 300×. B. Antisense, 300×. C. Wild-type, 100,000×. D. Antisense, 100,000×. Note: antisense pollen grains are smaller and shriveled in contrast to wild-type. The whitish granular structures on the right of FIGS. 24B and 24D are remnants of pollen grains that have failed to develop.

Morphological differences between transgenic and wild-type pollen grains were determined using a scanning electron microscope (FIG. 28). In general, the antisense pollen grains were much smaller and malformed as compared to wild-type pollen grains.

Figure 29:
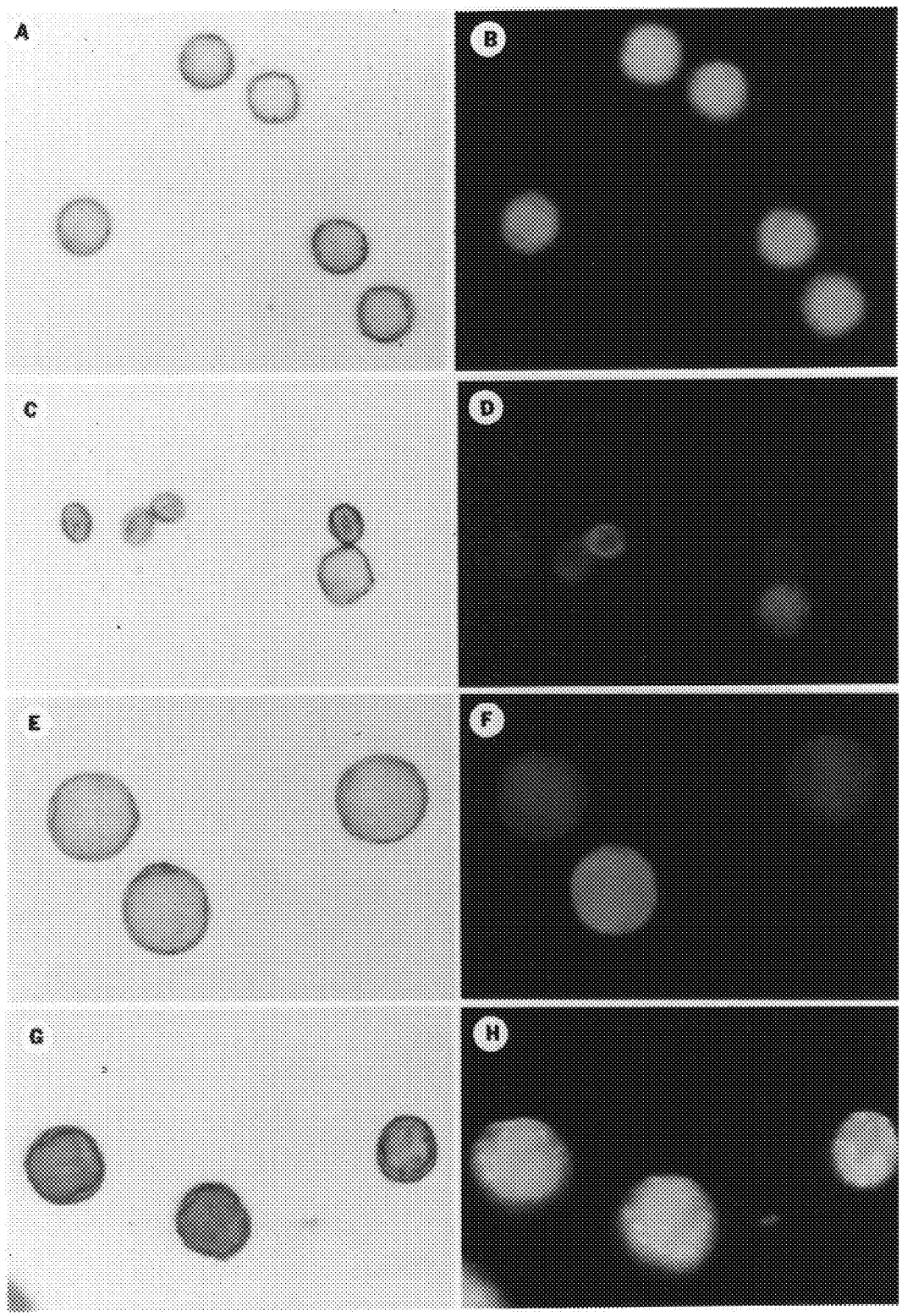
FIGS. 29A–29H show histochemical localization of callose in the outer walls of pollen grains from wild-type and antisense plants. On the left are the bright field images. On the right are the same respective views under blue excitation to highlight callose. A, B. Wild-type pollen grains, 300×. C, D. Antisense pollen grains, 300×. E, F. Wild-type pollen grains, 480×. G, H. Antisense pollen grains, 480×. Note: the pollen wall is not smooth and callose granules are unevenly distributed in antisense plants.

Histochemical localization of callose in the outer walls of pollen grains was compared between antisense and wild-type plants. The amount of callose in the outer walls of pollen grains was higher in the antisense plants. Callose distribution was uneven on the surface of the antisense pollen grains (FIG. 29H). Bright field micrographs revealed that wild-type pollen had a very smooth ring-like wall (FIG. 29E); antisense pollen were misshapen and lacked uniformity (FIG. 29G).

Figure 30:
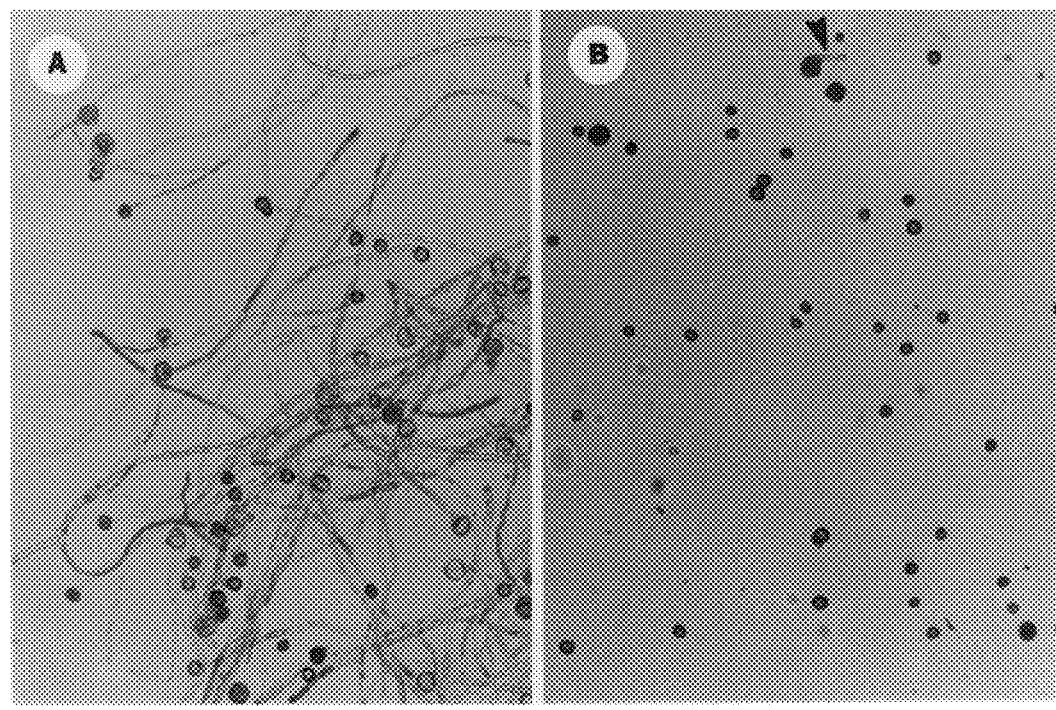
FIGS. 30A–30B show pollen germination. A. Wild-type pollen, 139×. B. Antisense pollen, 139×.

A drastically reduced number of pollen grains were observed in the four antisense plants. Although remnants of pollen-like structures were observed in antisense plants (FIG. 29B and 29D), they were not viable. Germination tests demonstrated that the frequency of pollen germination of wild-type and transgenic plants transformed with vector alone was more than 95%. The frequency of germination of antisense pollen was around 1–7% (Table 1 and FIG. 30). Furthermore, pollen from antisense plants that did germinate showed drastically retarded pollen tube growth as compared to wild-type pollen (FIG. 30).

The four antisense plants failed to produce fruit capsules and seeds in self crosses, but when these plants were cross-pollinated with wild-type pollen, normal fruit capsules and seeds developed, indicating that these transgenic plants were male sterile. Pistils in these antisense plants recognize and transmit pollen normally.

TABLE 1

Germination of pollen grains from antisense and control plants

| Type of Plant | Germination (%) |
|---|---|
| Wild Type | >95.0 |
| Control* | >95.0 |
| A3 | <1.0 |
| A4 | <1.5 |
| A14 | ~7.0 |
| A17 | ~5.0 |

*Vector DNA Alone

Figure 31:
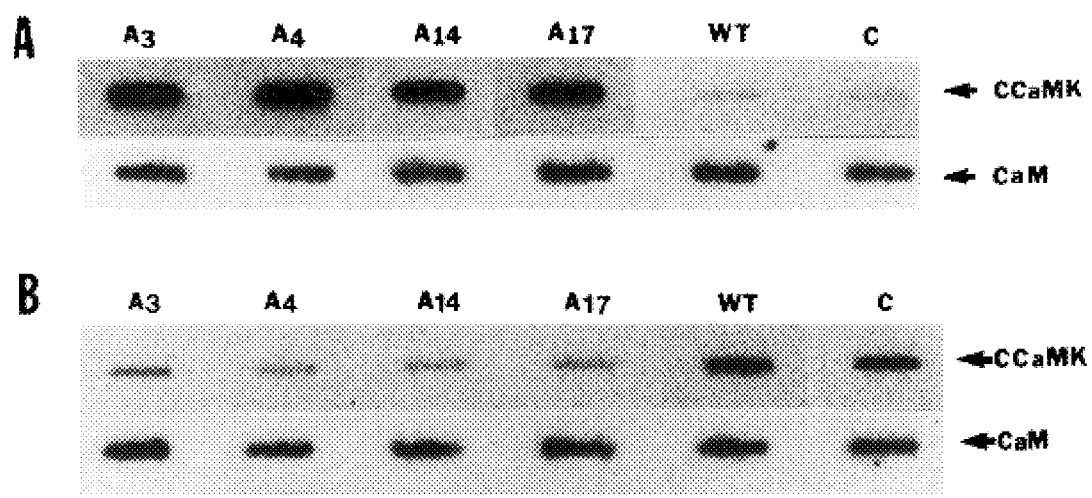
FIGS. 31A–31B.

RNA slot-blot hybridization was conducted to test the expression of CCaMK in antisense plants. RNA from 1.0 cm bud size anthers was hybridized with a $^{32}$P-labeled 330 bp probe (5' coding region, amino acid residues 1–109). Antisense plants (A3, A4, A14, and A17) showed high levels of CCaMK antisense RNA compared to wild-type plants and plants transformed with vector alone. Anthers from 1.0 cm buds (the stage at which CCaMK had the highest expression level, FIG. 24) were collected from antisense plants as well as control plants. Endogenous CCaMK mRNA isolated from A3, A4, A14, and A17 anthers was suppressed as compared to wild-type plants (FIG. 31). RT-PCR analysis using tobacco CCaMK gene-specific primers confirmed these results.

Anther development of antisense plants was compared to about 50 other transgenic tobacco plants as well as to transgenic plants with vector DNA alone. None of the antisense plants showed similar changes during anther development, suggesting that the observed male sterility is the result of suppression of CCaMK mRNA and not an artifact of the point of insertion of the CCaMK transgene or tissue culture manipulation.

Discussion

Although several anther-specific genes have been cloned, their role in microsporogenesis is not completely understood (Mascarenhas, *Annu. Rev. Plant Physiol. Plant Mol. Biol.* 41:317–338, 1990; McCormick, *Plant Cell* 5:1265–1275, 1993). CCaMK is a novel $Ca^{2+}$/calmodulin-dependent protein kinase expressed in an anther- and stage-specific manner during microsporogenesis.

The CCaMK gene of tobacco, a dicot, is similar in structure to the CCaMK gene of lily, a monocot, including the kinase catalytic domain, calmodulin-binding domain, and the visinin-like $Ca^{2+}$-binding domain. Tobacco and lily CCaMK share 71% identity and 82% similarity. High homology in the visinin-like domain (79% identity, 87% similarity) indicates that the visinin-like domain is conserved and controls CCaMK activity. The plant visinin-like domain contains three EF-hand motifs (FIGS. 22A and 22B), similar to animal visinin-like proteins such as frequenin, recoverin, and neurocalcin. These visinin-like proteins are members of $Ca^{2+}$-sensitive guanylyl cyclase activators involved in cation channel regulation in neuronal tissues (Palczewski et al., *Neuron* 13:395–404 1994). In animals, visinin-like proteins are restricted to specialized tissues such as neurons. CCaMK, which has a visinin-like domain, is also expressed in an anther- and stage-specific manner during microsporogenesis. The CCaMK mutant lacking the visinin-like domain did not show $Ca^{2+}$-dependent autophosphorylation. However, this mutant retained reduced activity as compared to the native enzyme, suggesting that the visinin-like domain is crucial for maximal activation of CCaMK (Takezawa et al., *J. Biol. Chem.* 271:8126–8132, 1996).

Transient signal-induced changes in free $Ca^{2+}$ concentration are known to switch on a series of biochemical changes, ultimately leading to a physiological response (Poovaiah and Reddy, *CRC Crit. Rev. Plant Sci.* 12:185–211, 1993). $Ca^{2+}$-induced conformational change in the visinin-like domain is believed to be critical for regulation of CCaMK activity. Furthermore, biochemical characterization has revealed that autophosphorylation is $Ca^{2+}$-dependent; a CCaMK mutant lacking this visinin-like domain did not show $Ca^{2+}$-dependent autophosphorylation. In contrast, substrate phosphorylation requires both $Ca^{2+}$ and calmodulin, suggesting a dual mode of regulation by $Ca^{2+}$ and calmodulin.

Plants are known to have multiple isoforms of calmodulin, some of which are signal-responsive and developmentally regulated (Jena, et al., *Proc. Natl. Acad. Sci. USA* 86:3644–3648, 1989; Braam and Davis, *Cell* 60:357–364, 1990; Ling et al., *Plant Physiol.* 96:1196–1202, 1991; Botella and Arteca, *Plant Mol. Biol.* 24:757–766, 1994; Takezawa, et al., *Plant Mol. Biol.* 27:693–703, 1995). Plant calmodulin mRNA and protein are known to have a relatively rapid turnover rate in the cell (Perera and Zelinski, *Plant Mol. Biol.* 19:649–664, 1992). Signal-induced changes in the calmodulin level and a rapid turnover rate in plants suggests that there is a dynamic regulation of calmodulin in vivo. Hence, it is likely that CCaMK activity is differentially controlled by signal-induced transient changes in free $Ca^{2+}$ concentration and calmodulin. The $Ca^{2+}$-dependent autophoshorylation of CCaMK is suppressed by calmodulin, indicating that both the messenger ($Ca^{2+}$) and the primary transducer of the $Ca^{2+}$ signal (calmodulin) control the function of CCaMK, which in turn regulates the function of key anther proteins such as the 24-kDa protein (FIG. 20).

In plants, protein phosphorylation has been implicated in signal transduction (Poovaiah and Reddy, *CRC Crit. Rev. Plant Sci.* 12:185–211, 1993; Stone et al., *Plant Physiol.* 108:451–457, 1995). Calcium controls CCaMK activity directly or indirectly through the action of calmodulin. The $Ca^{2+}$ signal is amplified through $Ca^{2+}$/calmodulin-dependent protein phosphorylation mediated by CCaMK. The coordinated regulation of CCaMK, its substrates, and binding proteins suggest that there is a cascade of events that are switched on by changes in the $Ca^{2+}$ level within the target cells. This transient change in $Ca^{2+}$ and possibly calmodulin leads to the dual regulation of CCaMK either through the autophosphorylation of CCaMK or through the phosphorylation of substrate(s) in a $Ca^{2+}$/calmodulin-dependent manner. Together, this coordinated regulation shows that CCaMK has a role in controlling the $Ca^{2+}$-mediated signaling cascade during microsporogenesis.

The developmental events leading to pollen development and release are precisely timed and regulated. Events that occur in the tapetum profoundly affect microspore development. Cell differentiation and dehiscence events occur in an exact chronological order that correlates with floral bud size in tobacco (Koltunow et al., *Plant Cell* 2:1201–1224, 1990). The CCaMK gene is expressed in anther in a stage-specific manner, being detectable during meiosis, reaching highest levels following meiosis, then becoming undetectable in later stages of development (FIG. 24). This programmed regulation, anther-specific expression, and induction of male sterility upon suppression of CCaMK message together indicate that CCaMK plays a role in microsporogenesis, affecting the deposition or degradation of callose in the outer wall of pollen.

Our attempts to suppress the CCaMK message using the CaMV 35S promoter have resulted in the production of male sterile plants. Plegt and Bino (*Mol. Gen. Genet.* 216:321–327, 1989) have shown that during premeiosis and meiosis, the 35S promoter is not active in the tapetum. Because there is high endogenous GUS activity at later stages of anther development, it is uncertain whether the 35S promoter is active in the tapetum at later stages of anther development. To maximize the effect of CCaMK suppression, the CCaMK promoter or other well-known plant promoters can be used.

Example 4

Transgenic Plants

Figure 32:
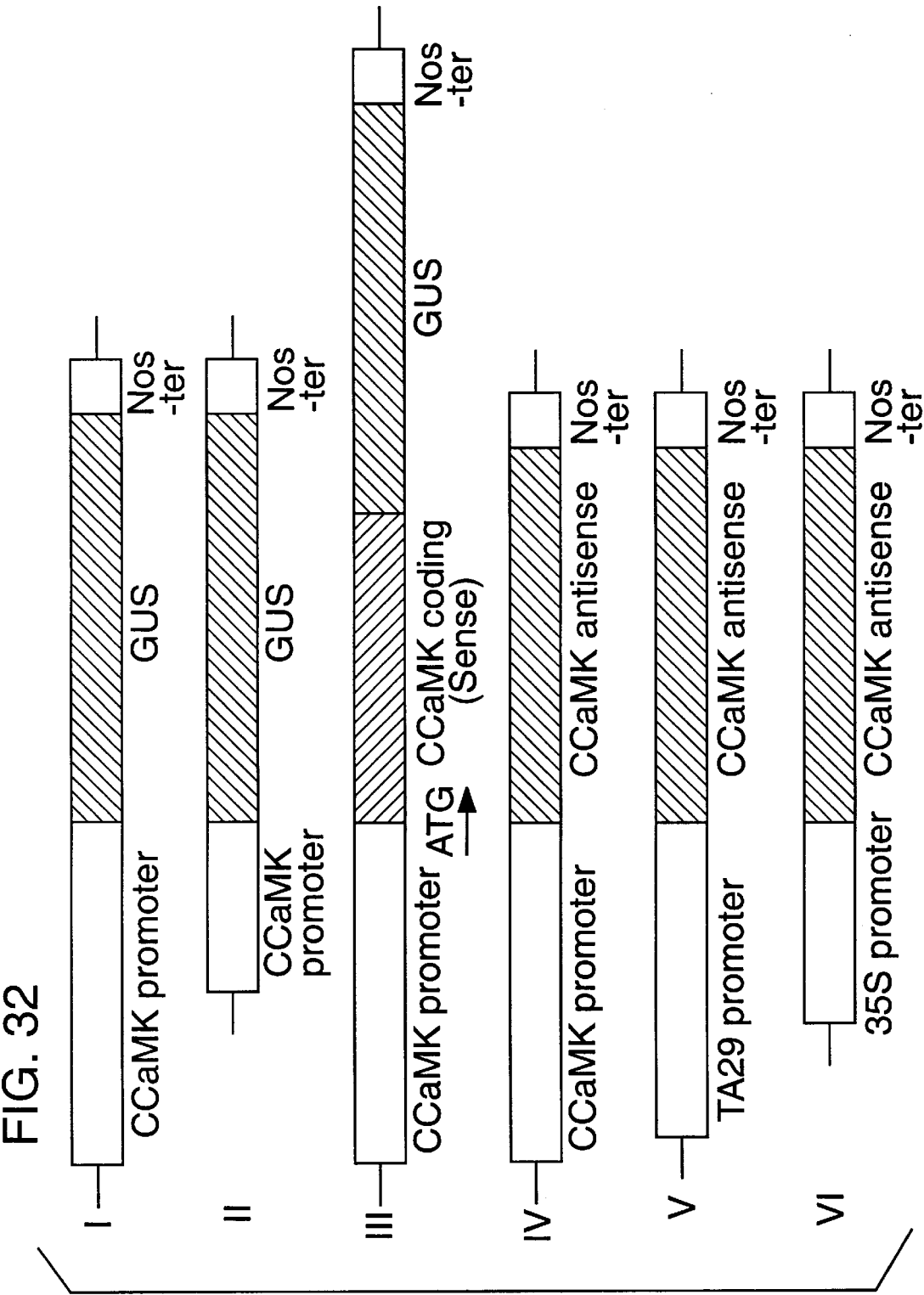
FIG. 32 shows GUS and antisense CCaMK constructs for transformation of plants. I. Transcriptional fusion of the tobacco CCaMK promoter to the β-glucuronidase (GUS)

As mentioned above, the tobacco CCaMK genomic clone has been obtained. FIG. 32 shows various constructs that have been introduced into tobacco to produce transgenic tobacco plants as described above. In order to construct a transcriptional fusion, a tobacco CCaMK promoter fragment of either 1.7 kb (FIG. 32, constructs I, III, and IV) or 0.6 kb (FIG. 32, construct II) was fused to the β-glucuronidase (GUS) reporter gene (FIG. 32, constructs I and II) or the tobacco CCaMK coding region in the antisense orientation (FIG. 32, construct IV). A perfect translational fusion was created between the tobacco CCaMK promoter (1.7 kb) and the tobacco CCaMK cDNA coding region in the sense orientation, to the 3'-end of which was fused the GUS reporter gene. For comparison purposes, transcriptional fusions were produced between the tobacco TA29 promoter (FIG. 32, construct V) or the CaMV 35S promoter (FIG. 32, construct VI) and the tobacco CCaMK coding region in the antisense orientation. All constructs included the *Agrobacterium tumefaciens* nopaline synthase terminator sequence (Nos-ter). Transgenic plants including each of the constructs shown in FIG. 32 have been produced.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. An isolated nucleic acid molecule encoding a protein having CCaMK protein biological activity, and comprising an amino acid sequence selected from the group consisting of:
   (a) the amino acid sequence shown in SEQ ID NO:1;
   (b) the amino acid sequence shown in SEQ ID NO:10;
   (c) the amino acid sequences that differ from that specified in (a) by one or more conservative amino acid substitutions: and (d) amino acid sequences that differ from that specified in (b) by one or more conservative amino acid substitutions.

2. An isolated nucleic acid molecule according to claim 1, wherein the molecule comprises a sequence selected from the group consisting of:
   (a) SEQ ID NO:1; and
   (b) SEQ ID NO:10.

3. An isolated nucleic acid molecule encoding a protein having an amino acid sequence having at least 70% sequence identity to an amino acid sequence according to claim 1, and having CCaMK protein biological activity.

4. A recombinant nucleic acid molecule comprising a promoter sequence operably linked to a nucleic acid sequence according to claim 3.

5. A recombinant nucleic acid molecule comprising a promoter sequence operably linked to a nucleic acid sequence according to claim 1.

6. A cell transformed with a recombinant nucleic acid molecule according to claim 5.

7. A transgenic plant comprising a recombinant nucleic acid molecule according to claim 5.

8. A cell transformed with a recombinant nucleic acid molecule according to claim 4.

9. A transgenic plant comprising a recombinant nucleic acid molecule according to claim 4.

10. An isolated nucleic acid molecule encoding a polypeptide having CCaMK protein biological activity, and comprising an amino acid sequence comprising:
    (a) a protein kinase domain;
    (b) a calmodulin-binding domain;
    (c) a visinin-like $Ca^{2+}$-binding domain; and
    (d) at least 70% sequence identity to amino acids 1–520 of SEQ ID NO:1.

11. An isolated nucleic acid molecule encoding a polypeptide having CCaMK protein biological activity, and comprising an amino acid sequence comprising:
    (a) a protein kinase domain;
    (b) a calmodulin-binding domain;
    (c) a visinin-like $Ca^{2+}$-binding domain; and
    (d) at least 70% sequence identity to amino acids 1–517 of SEQ ID NO:10.

12. An isolated nucleic acid molecule that:
    (a) hybridizes with a nucleic acid probe comprising nucleotides encoding amino acids 164–325 of SEQ ID NO:10 under wash conditions of room temperature, 2×SSC, and 0.5% SDS; then wash conditions of 65° C., 0.1×SSC, and 0.1% SDS; and
    (b) encodes a protein having CCaMK protein biological activity.

13. A recombinant nucleic acid molecule comprising a promoter sequence operably linked to a nucleic acid sequence according to claim 12.

14. An isolated nucleic acid molecule that:
    (a) hybridizes with a nucleic acid probe comprising nucleotides encoding amino acids 289–517 of SEQ ID NO:10 under wash conditions of room temperature, 2×SSC, and 0.5% SDS; then wash conditions of 65° C., 0.1×SSC, and 0.1% SDS; and
    (b) encodes a protein having CCaMK protein biological activity.

15. A recombinant nucleic acid molecule comprising a promoter sequence operably linked to a nucleic acid sequence according to claim 14.

16. A method for producing a male-sterile plant, comprising the steps:
    (a) providing a nucleotide sequence as recited in any one of claims 1, 3, 4, 5, 10, 11, 12, 13, 14, and 15;
    (b) providing an antisense construct of the nucleotide sequence;
    (c) introducing the construct of (b) into a plant cell to thereby produce a transformed plant cell; and
    (d) growing a plant from the transformed plant cell.

* * * * *

UNITED STATES PATENT AND TRADEMARK OFFICE
CERTIFICATE OF CORRECTION

PATENT NO. : 6,077,991
DATED : June 20, 2000
INVENTOR(S) : Poovaiah et al.

It is certified that error appears in the above-identified patent and that said Letters Patent is hereby corrected as shown below:

Title page,
Item [56], References Cited, "Fong et al., "Studies of the regulatory mechanism of Ca2+/ calmodulin-dependent protein kinase II," *J. Biol. Chem.*, 264:16759-16763, 1989." should read -- Fong et al., Studies of the regulatory mechanism of $Ca^{2+}$/ calmodulin-dependent protein kinase II," *J. Biol. Chem.*, 264:16759-16763, 1989. --.
"Harper et al., "A calcium-dependent protein kinases with a regulatory domain similar to calmodulin," *Science,* 252:951-252, 1991." should read -- Harper et al., "A calcium-dependent protein kinase with a regulatory domain similar to calmodulin," *Science,* 252:951-954, 1991. --
"O'Neil et al., "How calmoduin binds its targets: Sequence independent recognition of amphophilic α-helices," *TIBS*, 15:59-64, 1990." should read -- O'Neil et al., "How calmodulin binds its targets: Sequence independent recognition of amphophilic α-helices," *TIBS*, 15:59-64, 1990.

Column 1,
Line 26, "*Plant Mol. Biold.*" should read -- *Plant Mol. Biol.* --.
Line 27, "*Trewavas*" should read -- Trewavas --.

Column 2,
Line 18, "formation to reduced" should read -- formation to reduce --.

Column 3,
Line 15, "SEQ ID NO:1) DLKPEN" should read -- SEQ ID NO:1); DLKPEN --.
Line 16, "SEQ ID NO:1) SIDYVSPE" should read -- SEQ ID NO:1); SIDYVSPE --.

Column 4,
Line 28, "ASEQ" should read -- SEQ --.

Column 5,
Line 4, "CCamKs" should read -- CCaMKs --.
Line 28, "calmodulind-ependent" should read -- calmodulin-dependent --.

Column 9,
Line 53, "Homoloqs" should read -- Homologs --.

Column 11,
Line 34, "poly-petide" should read -- polypeptide --.
Line 61, "Polweptides" should read -- Polypeptides --.

UNITED STATES PATENT AND TRADEMARK OFFICE
CERTIFICATE OF CORRECTION

PATENT NO.    : 6,077,991
DATED         : June 20, 2000
INVENTOR(S)   : Poovaiah et al.

It is certified that error appears in the above-identified patent and that said Letters Patent is hereby corrected as shown below:

Column 12,
Line 18, "Madison, Wis.)." should read -- Madison, Wis. --.
Line 23, ""Isolated."" should read -- "Isolated," --.

Column 14,
Lines 12-13, "expressing recombinant a" should read -- expressing a recombinant --.

Column 15,
Line 12, "potent" should read -- totipotent --.
Line 41, "Tag" should read -- Taq --.
Line 41, "100 $\mu$l" should read -- 100 $\mu$L --.

Column 16,
Line 34, "$^{45}$Ca-Bindinq" should read -- $^{45}$Ca-Binding --.

Column 18,
Line 39, "1984))." should read -- 1984). --.

Column 20,
Line 22, "oligo" should read -- Oligo --.

Column 25,
Lines 19-20, "autophosphorylatiothreonine the" should read -- autophosphorylation is due to the --.

Column 27,
Line 33, "PCR. cDNA" should read -- PCR, cDNA --.
Line 65, "(SEQ ID N:10)" should read -- SEQ ID NO:10) --.

Column 29,
Line 6, "dried was subjected" should read -- dried and subjected --.
Line 30, "CCaMK ($^{32}$P-labeled) CCaMK." should read -- CCaMK ($^{32}$P-labeled). --.
Line 43, "sequence (after "1776 bp"))" should read -- sequence) --.
Line 44, "SRI)" should read -- SR1) --.

UNITED STATES PATENT AND TRADEMARK OFFICE
CERTIFICATE OF CORRECTION

PATENT NO. : 6,077,991
DATED : June 20, 2000
INVENTOR(S) : Poovaiah et al.

It is certified that error appears in the above-identified patent and that said Letters Patent is hereby corrected as shown below:

Column 30,
Line 1, "calmodulinbinding" should read -- calmodulin-binding --.

Column 32,
Line 7, "404 1994)." should read -- 404, 1994). --.

Column 57,
Lines 34-35, "substitutions: and" should read -- substitutions; and --.

Signed and Sealed this

Tenth Day of September, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 2514 base pairs
      (B) TYPE: nucleic acid
      (C) STRANDEDNESS: double stranded
      (D) TOPOLOGY: linear (ii) MOLECULE TYPE: cDNA to mRNA
      (A) DESCRIPTION: Lily CCaMK cDNA and deduced amino-acid sequence (xi) SEQUENCE DESCRIPTION: SEQ ID NO:1:

```
GCTGGCTTTA TTCCTCTGCT ACCAATTTAG TATAATACCT CTCCCCATCC ATCATCATCT        60

TGACGTCCCT AGCTCCCCAT TTTTTCTTTT TTTAAAATCC GTGAGTCAAT TTCTTGTTTT       120

CATACTCCCC ACATTCACAC CAACCCCTAT CCAACCCCTT ACTCCCCATT CCAAAATCTG       180

AGTTCTTCTC AGATTCTTGA TAAGAGTAAA GGTTGTCCAG AATTGATATT TTCTTCAATA       240

CCATATTCCA GTTTCTGGAT TACTTGATTC CAATATTAAG CTTGATTGAT GATATGAGCA       300

AAGGGGTTGT CTGTAATTAA GCTTAAGCTT GTCTTCAATA CCCATATTTC AGTTTCTGGA       360

TTTCTGTCGG AATTTTCGTA TCAGGATTCC GATATTGACC TTGATTCTTG ATTCAAGCAA       420

AAGGTAGTCC GGATTGCTGG ATTCCAATAT TGACCTTGAT TCTTGATCAA GCAAAGGGTT       480

GTTCGGTGTA CTGGCAAAGG ATTGTCAGGA TTACTGCTCC GAATTTCACA CACATTTGGG       540
```

```
TAAATTACAG TAGAAGGTAC TGAGTCCTTG AAATTGAATG TTGTTCTCTT GAAAGTGGGA       600

TTGTGAGTTG GAGGTGGCAT TTAACCCAGG CTTG                                  634

ATG TCG AGG CAT GAG AGC AGA AAG CTC TCG GAT GAT TAT GAA GTG GTT        682
Met Ser Arg His Glu Ser Arg Lys Leu Ser Asp Asp Tyr Glu Val Val
              5                  10                  15

GAT GTT CTT GGA AAA GGC GGA TTC TCG GTT GTA AGG AGA GGA ATC AGC        730
Asp Val Leu Gly Lys Gly Gly Phe Ser Val Val Arg Arg Gly Ile Ser
             20                  25                  30

AAA TCA AGA GGG AAG AAC AAT GAT GTT GCT ATC AAG ACC TTG AGA AGA        778
Lys Ser Arg Gly Lys Asn Asn Asp Val Ala Ile Lys Thr Leu Arg Arg
         35                  40                  45

TAC GGG TAC ACG CTT CCG GGG GCG CAG CGG AGC CAA CCT GGG CAG AGG        826
Tyr Gly Tyr Thr Leu Pro Gly Ala Gln Arg Ser Gln Pro Gly Gln Arg
     50                  55                  60

GGG TTG TCT CCT TTA GGA ATG CCC ACA CTG AAG CAA GTT TCT GTT TCG        874
Gly Leu Ser Pro Leu Gly Met Pro Thr Leu Lys Gln Val Ser Val Ser
 65                  70                  75                  80

GAT GCG TTG CTC ACG AAT GAA ATT CTG GTC ATG AGG AGA ATA GTG GAG        922
Asp Ala Leu Leu Thr Asn Glu Ile Leu Val Met Arg Arg Ile Val Glu
                 85                  90                  95

GAT GTT TCT CCT CAC CCT AAT GTG ATC CAC CTG CAT GAT GTG TAT GAA        970
Asp Val Ser Pro His Pro Asn Val Ile His Leu His Asp Val Tyr Glu
            100                 105                 110

GAT GCA AAT GGA GTT CAT CTT GTG CTG GAG CTT TGC TCT GGC GGG GAG       1018
Asp Ala Asn Gly Val His Leu Val Leu Glu Leu Cys Ser Gly Gly Glu
        115                 120                 125

TTG TTT GAT CGG ATA GTT GCG CAG GAT CGG TAT TCG GAA TCA GAG GCG       1066
Leu Phe Asp Arg Ile Val Ala Gln Asp Arg Tyr Ser Glu Ser Glu Ala
    130                 135                 140

GCT GAA GTG GTC CAG CAG ATA GCG AGT GGG TTA GCT GCA CTT CAT AAA       1114
Ala Glu Val Val Gln Gln Ile Ala Ser Gly Leu Ala Ala Leu His Lys
145                 150                 155                 160

TCC ACT ATC ATT CAT CGC GAT TTG AAG CCA GAG AAT TGT TTG TTT CTG       1162
Ser Thr Ile Ile His Arg Asp Leu Lys Pro Glu Asn Cys Leu Phe Leu
                165                 170                 175

AAT CAA GAG AAA CGT TCT ACT CTG AAA ATA ATG GAC TTT GGT CTA AGT       1210
Asn Gln Glu Lys Arg Ser Thr Leu Lys Ile Met Asp Phe Gly Leu Ser
            180                 185                 190

TCT GTG GAA GAT TTT ACT GAT CCT ATA GTT GCT CTG TTT GGT TCG ATT       1258
Ser Val Glu Asp Phe Thr Asp Pro Ile Val Ala Leu Phe Gly Ser Ile
        195                 200                 205

GAT TAT GTT TCT CCT GAA GCT TTG TCT CAG CGT CAA GTT AGC TCA GCT       1306
Asp Tyr Val Ser Pro Glu Ala Leu Ser Gln Arg Gln Val Ser Ser Ala
    210                 215                 220

AGC GAC ATG TGG TCT CTT GGG GTG ATA TTG TAT ATC CTT CTC TCC GGA       1354
Ser Asp Met Trp Ser Leu Gly Val Ile Leu Tyr Ile Leu Leu Ser Gly
225                 230                 235                 240

TGC CCA CCT TTT CAT GCA CCA TCA AAT CGG GAA AAG CAG CAG CGG ATA       1402
Cys Pro Pro Phe His Ala Pro Ser Asn Arg Glu Lys Gln Gln Arg Ile
                245                 250                 255

CTG GCA GGT GAT TTC AGC TTT GAG GAG CAC ACG TGG AAG ACC ATA ACT       1450
Leu Ala Gly Asp Phe Ser Phe Glu Glu His Thr Trp Lys Thr Ile Thr
            260                 265                 270

TCA TCA GCA AAG GAT TTG ATT TCC AGT CTT TTG TCT GTT GAT CCT TAC       1498
Ser Ser Ala Lys Asp Leu Ile Ser Ser Leu Leu Ser Val Asp Pro Tyr
        275                 280                 285

AAA AGA CCA ACT GCT AAT GAT CTT TTG AAG CAT CCT TGG GTG ATA GGG       1546
Lys Arg Pro Thr Ala Asn Asp Leu Leu Lys His Pro Trp Val Ile Gly
```

```
            290                 295                 300
GAC TCT GCC AAA CAG GAA CTA ATT GAA CCA GAG GTT GTT TCT AGA CTG       1594
Asp Ser Ala Lys Gln Glu Leu Ile Glu Pro Glu Val Val Ser Arg Leu
305                 310                 315                 320

CGA AGT TTC AAT GCT CGG CGG AAA TTA CGT GCA GCT GCA ATA GCC AGT       1642
Arg Ser Phe Asn Ala Arg Arg Lys Leu Arg Ala Ala Ala Ile Ala Ser
                    325                 330                 335

GTT TTG AGT AGC AAA GTT TTG TTG AGA ACA AAG AAA CTG AAG AAT TTG       1690
Val Leu Ser Ser Lys Val Leu Leu Arg Thr Lys Lys Leu Lys Asn Leu
                340                 345                 350

CTT GGA TCC CAT GAT ATG AAA TCG GAG GAA CTT GAA AAT CTC CGA GCT       1738
Leu Gly Ser His Asp Met Lys Ser Glu Glu Leu Glu Asn Leu Arg Ala
            355                 360                 365

CAC TTT AAG AGA ATA TGT GCA AAT GGA GAC AAT GCG ACA CTA CCG GAG       1786
His Phe Lys Arg Ile Cys Ala Asn Gly Asp Asn Ala Thr Leu Pro Glu
        370                 375                 380

TTC GAG GAA GTT CTT AAA GCG ATG AAA ATG AAT TCT CTA ATC CCT CTT       1834
Phe Glu Glu Val Leu Lys Ala Met Lys Met Asn Ser Leu Ile Pro Leu
385                 390                 395                 400

GCG CCT CGG GTA TTT GAC CTA TTT GAC AAC AAC CGT GAT GGA ACT ATA       1882
Ala Pro Arg Val Phe Asp Leu Phe Asp Asn Asn Arg Asp Gly Thr Ile
                    405                 410                 415

GAC ATG AGA GAG ATA TTA TGT GGG TTG TCG AAT CTT AGG AAC TCA CAA       1930
Asp Met Arg Glu Ile Leu Cys Gly Leu Ser Asn Leu Arg Asn Ser Gln
                420                 425                 430

GGC GAT GAT GCT CTC CAG CTC TGT TTT CAG ATG TAT GAT GCC GAC AGG       1978
Gly Asp Asp Ala Leu Gln Leu Cys Phe Gln Met Tyr Asp Ala Asp Arg
            435                 440                 445

TCT GGA TGT ATC AGC AAG GAG GAA TTA GCA TCA ATG CTT AGG GCC TTG       2026
Ser Gly Cys Ile Ser Lys Glu Glu Leu Ala Ser Met Leu Arg Ala Leu
        450                 455                 460

CCC GAG GAT TGT GTT CCT GCC GAT ATA ACA GAG CCA GGA AAG TTG GAC       2074
Pro Glu Asp Cys Val Pro Ala Asp Ile Thr Glu Pro Gly Lys Leu Asp
465                 470                 475                 480

GAG ATC TTT GAT CAG ATG GAC GCC AAC AGT GAT GGA GTT GTC ACG TTC       2122
Glu Ile Phe Asp Gln Met Asp Ala Asn Ser Asp Gly Val Val Thr Phe
                    485                 490                 495

GAC GAG TTC AAA GCC GCT ATG CAA AGA GAC AGC TCC CTG CAA GAC GTG       2170
Asp Glu Phe Lys Ala Ala Met Gln Arg Asp Ser Ser Leu Gln Asp Val
                500                 505                 510

GTT CTA TCT TCG CTG CGA ACG ATA TAG                                   2197
Val Leu Ser Ser Leu Arg Thr Ile
            515                 520

TCCTCTCTGG TCCTTCCCTT ACGAATCAGT GGTGTGCAGG TCACAGATCG TAGGGTGGAA    2257

TAACAATCAA TATTTTAGCT TCTATCATAA ATCATCTGAG AGGTGTAAAA CATTATGTAC    2317

AGTATAGAGA ACAAGCATGT GTTTATGATC TGTCATATGA AATCGATGTC TCAGTGACTC    2377

ATAACCTTTG TCACGAAATG TATCAGAGAG AACTTTCCCA ATTTAGGCTA TTGTAGTTCT    2437

ATCGACTTTT GTATCTAACT AAATGAATCA TCTAAGCCTG TCCTTGATGT GTAAGGGATT    2497

ATGTGCTTAC AGTTTCT                                                    2514
```

(2) INFORMATION FOR SEQ ID NO: 2:

(i) SEQUENCE CHARACTERISTICS:
        (A) LENGTH: 193 amino acids
        (B) TYPE: amino acid
        (D) TOPOLOGY: linear (ii) MOLECULE TYPE: protein (A) DESCRIPTION: Region of rat hippocalcin (Gen2:Ratp23K)
with homology to lily CCaMK (xi) SEQUENCE DESCRIPTION: SEQ ID NO:2:

Met Gly Lys Gln Asn Ser Lys Leu Arg Pro Glu Met Leu Gln Asp Leu
                 5                  10                  15

Arg Glu Asn Thr Glu Phe Ser Glu Leu Glu Leu Gln Glu Trp Tyr Lys
                20                  25                  30

Gly Phe Leu Lys Asp Cys Pro Thr Gly Ile Leu Asn Val Asp Glu Phe
             35                  40                  45

Lys Lys Ile Tyr Ala Asn Phe Phe Pro Tyr Gly Asp Ala Ser Lys Phe
 50                  55                  60

Ala Glu His Val Phe Arg Thr Phe Asp Ile Asn Ser Asp Gly Thr Ile
 65                  70                  75                  80

Asp Phe Arg Glu Phe Ile Ile Ala Leu Ser Val Thr Ser Arg Gly Arg
                 85                  90                  95

Leu Glu Gln Lys Ile Met Trp Ala Phe Ser Met Tyr Asp Leu Asp Gly
                100                 105                 110

Asn Gly Tyr Ile Ser Arg Glu Glu Met Leu Glu Ile Val Gln Ala Ile
                115                 120                 125

Tyr Lys Met Val Ser Ser Val Met Lys Met Pro Glu Asp Glu Ser Thr
 130                 135                 140

Pro Glu Lys Arg Thr Glu Lys Ile Phe Arg Gln Met Asp Ile Asn Asn
 145                 150                 155                 160

Asp Gly Lys Leu Ser Leu Glu Glu Phe Ile Arg Gly Ala Lys Ser Asp
                165                 170                 175

Pro Ser Ile Val Arg Leu Leu Gln Cys Asp Pro Ser Ser Ala Ser Gln
                180                 185                 190

Phe (2) INFORMATION FOR SEQ ID NO: 3:

(i) SEQUENCE CHARACTERISTICS:
        (A) LENGTH: 193 amino acids
        (B) TYPE: amino acid
        (D) TOPOLOGY: linear (ii) MOLECULE TYPE: protein
        (A) DESCRIPTION: Region of rat neural visinin-like protein
            (Gen2:Ratnvp3) with homology to lily CCaMK (xi) SEQUENCE DESCRIPTION: SEQ ID NO:3:

Met Gly Lys Gln Asn Ser Lys Leu Arg Pro Glu Val Leu Gln Asp Leu
                 5                  10                  15

Arg Glu His Thr Glu Phe Thr Asp His Glu Leu Gln Glu Trp Tyr Lys
                20                  25                  30

Gly Phe Leu Lys Asp Cys Pro Thr Gly His Leu Thr Val Asp Glu Phe
             35                  40                  45

Lys Lys Ile Tyr Ala Asn Phe Phe Pro Tyr Gly Asp Ala Ser Lys Phe
 50                  55                  60

Ala Glu His Val Phe Arg Thr Phe Asp Ile Asn Ser Asp Gly Thr Ile
 65                  70                  75                  80

Asp Phe Arg Glu Phe Ile Ile Ala Leu Ser Val Thr Ser Arg Gly Lys
                 85                  90                  95

Leu Glu Gln Lys Ile Lys Trp Ala Phe Ser Met Tyr Asp Leu Asp Gly
                100                 105                 110

Asn Gly Tyr Ile Ser Arg Ser Glu Met Leu Glu Ile Val Gln Ala Ile

-continued

```
            115                 120                 125
Tyr Lys Met Val Ser Ser Val Met Lys Met Pro Glu Asp Glu Ser Thr
        130                 135                 140
Pro Glu Lys Arg Thr Asp Lys Ile Phe Arg Gln Met Asp Ile Asn Asn
145                 150                 155                 160
Asp Gly Lys Leu Ser Leu Glu Glu Phe Ile Lys Gly Ala Lys Ser Asp
                165                 170                 175
Pro Ser Ile Val Arg Leu Leu Gln Cys Asp Pro Ser Ser Ala Ser Gln
                180                 185                 190
Phe
```

(2) INFORMATION FOR SEQ ID NO: 4:

(i) SEQUENCE CHARACTERISTICS:
        (A) LENGTH: 193 amino acids
        (B) TYPE: amino acid
        (D) TOPOLOGY: linear (ii) MOLECULE TYPE: protein
        (A) DESCRIPTION: Region of bovine neurocalcin
        (Gen2:Bovpcaln) with homology to lily CCaMK (xi) SEQUENCE DESCRIPTION: SEQ ID NO:4:

```
Met Gly Lys Gln Asn Ser Lys Leu Arg Pro Glu Val Met Gln Asp Leu
                5                  10                  15
Leu Glu Ser Ile Asp Phe Thr Glu His Glu Ile Gln Glu Trp Tyr Lys
                20                  25                  30
Gly Phe Leu Arg Asp Cys Pro Ser Gly His Leu Ser Met Glu Glu Phe
                35                  40                  45
Lys Lys Ile Tyr Gly Asn Phe Phe Pro Tyr Gly Asp Ala Ser Lys Phe
50                  55                  60
Ala Glu His Val Phe Arg Thr Phe Asp Ala Asn Gly Asp Gly Thr Ile
65                  70                  75                  80
Asp Phe Arg Glu Phe Ile Ile Ala Leu Ser Val Thr Ser Arg Gly Lys
                85                  90                  95
Leu Glu Gln Lys Ile Lys Trp Ala Phe Ser Met Tyr Asp Leu Asp Gly
                100                 105                 110
Asn Gly Tyr Ile Ser Lys Ala Glu Met Leu Glu Ile Val Gln Ala Ile
                115                 120                 125
Tyr Lys Met Val Ser Ser Val Met Lys Met Pro Glu Asp Glu Ser Thr
        130                 135                 140
Pro Glu Lys Arg Thr Glu Lys Ile Phe Arg Gln Met Asp Ile Asn Arg
145                 150                 155                 160
Asp Gly Lys Leu Ser Leu Glu Glu Phe Ile Arg Gly Ala Lys Ser Asp
                165                 170                 175
Pro Ser Ile Val Arg Leu Leu Gln Cys Asp Pro Ser Ser Ala Gly Gln
                180                 185                 190
Phe
```

(2) INFORMATION FOR SEQ ID NO: 5:

(i) SEQUENCE CHARACTERISTICS:
        (A) LENGTH: 191 amino acids
        (B) TYPE: amino acid
        (D) TOPOLOGY: linear (ii) MOLECULE TYPE: protein
        (A) DESCRIPTION: Region of rat neural visinin-like protein
        (Gen2:Ratnvp1) with homology to lily CCaMK (xi) SEQUENCE DESCRIPTION: SEQ ID NO:5:

Met Gly Lys Gln Asn Ser Lys Leu Ala Pro Glu Val Met Glu Asp Leu
              5                   10                  15

Val Lys Ser Thr Glu Phe Asn Glu His Glu Leu Lys Gln Trp Tyr Lys
             20                  25                  30

Gly Phe Leu Lys Asp Cys Pro Ser Gly Arg Leu Asn Leu Glu Glu Phe
             35                  40                  45

Gln Gln Leu Tyr Val Lys Phe Phe Pro Tyr Gly Asp Ala Ser Lys Phe
 50                  55                  60

Ala Gln His Ala Phe Arg Thr Phe Asp Lys Asn Gly Asp Gly Thr Ile
 65                  70                  75                  80

Asp Phe Arg Glu Phe Ile Cys Ala Leu Ser Ile Thr Ser Arg Gly Ser
                 85                  90                  95

Phe Glu Gln Lys Leu Asn Trp Ala Phe Asn Met Tyr Asp Leu Asp Gly
                100                 105                 110

Asp Gly Lys Ile Thr Arg Val Glu Met Leu Glu Ile Ile Glu Ala Ile
            115                 120                 125

Tyr Lys Met Val Gly Thr Val Ile Met Met Lys Met Asn Glu Asp Gly
130                 135                 140

Leu Thr Pro Glu Gln Arg Val Asp Lys Ile Phe Ser Lys Met Asp Lys
145                 150                 155                 160

Asn Lys Asp Asp Gln Ile Thr Leu Asp Glu Phe Lys Glu Ala Ala Lys
                165                 170                 175

Ser Asp Pro Ser Ile Val Leu Leu Leu Gln Cys Asp Ile Gln Lys
                180                 185                 190

(2) INFORMATION FOR SEQ ID NO: 6:

(i) SEQUENCE CHARACTERISTICS:
       (A) LENGTH: 191 amino acids
       (B) TYPE: amino acid
       (D) TOPOLOGY: linear (ii) MOLECULE TYPE: protein
       (A) DESCRIPTION: Region of chicken visinin-like protein
       (Gen2:Ggvilip) with homology to lily CCaMK (xi) SEQUENCE DESCRIPTION: SEQ ID NO:6:

Met Gly Lys Gln Asn Ser Lys Leu Ala Pro Glu Val Met Glu Asp Leu
              5                   10                  15

Val Lys Ser Thr Glu Phe Asn Glu His Glu Leu Lys Gln Trp Tyr Lys
             20                  25                  30

Gly Phe Leu Lys Asp Cys Pro Ser Gly Arg Leu Asn Leu Glu Glu Phe
             35                  40                  45

Gln Gln Leu Tyr Val Lys Phe Phe Pro Tyr Gly Asp Ala Ser Lys Phe
 50                  55                  60

Ala Gln His Ala Phe Arg Thr Phe Asp Lys Asn Gly Asp Gly Thr Ile
 65                  70                  75                  80

Asp Phe Arg Glu Phe Ile Cys Ala Leu Ser Ile Thr Ser Arg Gly Ser
                 85                  90                  95

Phe Glu Gln Lys Leu Asn Trp Ala Phe Asn Met Tyr Asp Leu Asp Gly
                100                 105                 110

Asp Gly Lys Ile Thr Arg Val Glu Met Leu Glu Ile Ile Glu Ala Ile
            115                 120                 125

Tyr Lys Met Val Gly Thr Val Ile Met Met Lys Met Asn Glu Asp Gly
130                 135                 140

Leu Thr Pro Glu Gln Arg Val Asp Lys Ile Phe Ser Lys Met Asp Lys
145                 150                 155                 160

Asn Lys Asp Asp Gln Ile Thr Leu Asp Glu Phe Lys Glu Ala Ala Lys
                165                 170                 175

Ser Asp Pro Ser Ile Val Leu Leu Gln Cys Asp Ile Gln Lys
            180                 185                 190

(2) INFORMATION FOR SEQ ID NO: 7:

(i) SEQUENCE CHARACTERISTICS:
        (A) LENGTH: 191 amino acids
        (B) TYPE: amino acid
        (D) TOPOLOGY: linear (ii) MOLECULE TYPE: protein
        (A) DESCRIPTION: Region of rat neural visinin-like protein
        (Gen2:Ratnvp2) with homology to lily CCaMK (xi) SEQUENCE DESCRIPTION: SEQ ID NO:7:

Met Gly Lys Asn Asn Ser Lys Leu Ala Pro Glu Glu Leu Glu Asp Leu
                5                   10                  15

Val Gln Asn Thr Glu Phe Ser Glu Gln Glu Leu Lys Gln Trp Tyr Lys
                20                  25                  30

Gly Phe Leu Lys Asp Cys Pro Ser Gly Ile Leu Asn Leu Glu Glu Phe
            35                  40                  45

Gln Gln Leu Tyr Ile Lys Phe Phe Pro Tyr Gly Asp Ala Ser Lys Phe
50                  55                  60

Ala Gln His Ala Phe Arg Thr Phe Asp Lys Asn Gly Asp Gly Thr Ile
65                  70                  75                  80

Asp Phe Arg Glu Phe Ile Cys Ala Leu Ser Val Thr Ser Arg Gly Ser
                85                  90                  95

Phe Glu Gln Lys Leu Asn Trp Ala Phe Glu Met Tyr Asp Leu Asp Gly
            100                 105                 110

Asp Gly Arg Ile Thr Arg Leu Glu Met Leu Glu Ile Ile Glu Ala Ile
            115                 120                 125

Tyr Lys Met Val Gly Thr Val Ile Met Met Arg Met Asn Gln Asp Gly
130                 135                 140

Leu Thr Pro Gln Gln Arg Val Asp Lys Ile Phe Lys Lys Met Asp Gln
145                 150                 155                 160

Asp Lys Asp Asp Gln Ile Thr Leu Glu Glu Phe Lys Glu Ala Ala Lys
                165                 170                 175

Ser Asp Pro Ser Ile Val Leu Leu Gln Cys Asp Met Gln Lys
            180                 185                 190

(2) INFORMATION FOR SEQ ID NO: 8:

(i) SEQUENCE CHARACTERISTICS:
        (A) LENGTH: 186 amino acids
        (B) TYPE: amino acid
        (D) TOPOLOGY: linear (ii) MOLECULE TYPE: protein
        (A) DESCRIPTION: Region of Drosophila frequenin
        (Gen2:Drofreq) with homology to lily CCaMK (xi) SEQUENCE DESCRIPTION: SEQ ID NO:8:

Met Gly Lys Lys Ser Ser Lys Leu Lys Gln Asp Thr Ile Asp Arg Leu
                5                   10                  15

Thr Thr Asp Thr Tyr Phe Thr Glu Lys Glu Ile Arg Gln Trp His Lys
                20                  25                  30

```
Gly Phe Leu Lys Asp Cys Pro Asn Gly Leu Leu Thr Glu Gln Gly Phe
         35                  40                  45

Ile Lys Ile Tyr Lys Gln Phe Phe Pro Gln Gly Asp Pro Ser Lys Phe
 50                  55                  60

Ala Ser Leu Val Phe Arg Val Phe Asp Glu Asn Asn Asp Gly Ser Ile
65                  70                  75                  80

Glu Phe Glu Glu Phe Ile Arg Ala Leu Ser Val Thr Ser Lys Gly Leu
                 85                  90                  95

Asp Glu Lys Leu Gln Trp Ala Phe Arg Leu Tyr Asp Val Asp Asn Asp
                100                 105                 110

Gly Tyr Ile Thr Arg Glu Glu Met Tyr Asn Ile Val Asp Ala Ile Tyr
                115                 120                 125

Gln Met Val Gly Gln Gln Pro Gln Ser Glu Asp Glu Asn Thr Pro Gln
130                 135                 140

Lys Arg Val Asp Lys Ile Phe Asp Gln Met Asp Lys Asn His Asp Gly
145                 150                 155                 160

Lys Leu Thr Leu Glu Glu Phe Arg Glu Gly Ser Lys Ala Asp Pro Arg
                165                 170                 175

Ile Val Gln Ala Leu Ser Leu Gly Gly Gly
                180                 185
```

(2) INFORMATION FOR SEQ ID NO: 9:

(i) SEQUENCE CHARACTERISTICS:
        (A) LENGTH: 30 amino acids
        (B) TYPE: amino acid
        (D) TOPOLOGY: linear (ii) MOLECULE TYPE: protein
        (A) DESCRIPTION: Putative calmodulin-binding site of alpha
            subunit of mammalian calmodulin kinase II
            (amino acids 281-310)

(xi) SEQUENCE DESCRIPTION: SEQ ID NO:9:

```
Met His Arg Gln Glu Thr Val Asp Cys Leu Lys Lys Phe Asn Ala Arg
                285                 290                 295

Arg Lys Leu Lys Gly Ala Ile Leu Thr Thr Met Leu Ala Thr
                300                 305                 310
```

(2) INFORMATION FOR SEQ ID NO: 10:

(i) SEQUENCE CHARACTERISTICS:
        (A) LENGTH: 1776 base pairs
        (B) TYPE: nucleic acid
        (C) STRANDEDNESS: double stranded
        (D) TOPOLOGY: linear (ii) MOLECULE TYPE: cDNA to mRNA
        (A) DESCRIPTION: Tobacco CCaMK cDNA and deduced amino-acid
            sequence (ix) FEATURE:
        (A) NAME/KEY: protein-coding sequence (not including
            stop codon)
        (B) LOCATION: nucleotides 20-1570

(xi) SEQUENCE DESCRIPTION: SEQ ID NO:10:

```
TAATTAACCT TTCTCTCTC                                                  19

ATG GGA CAA AGG GAA GAT GGA AAA ACT CTA AGT GAT GAA TAT GAA GTG       67
Met Gly Gln Arg Glu Asp Gly Lys Thr Leu Ser Asp Glu Tyr Glu Val
          5                  10                  15

ACA GAT ATA CTT GGA AGA GGA GGG TTT TCA GTA GTG AGG AGA GGA ACA      115
```

-continued

```
Thr Asp Ile Leu Gly Arg Gly Gly Phe Ser Val Val Arg Arg Gly Thr
         20                      25                      30

AGA AGA AGA ACA CTA CAT TCG GGT CAA CAT CAT GAA GTT GTT GCC ATT        163
Arg Arg Arg Thr Leu His Ser Gly Gln His His Glu Val Val Ala Ile
             35                      40                      45

AAA ACC CTC CGG CGG TTC GGG CCA CCA CCG GCG CCG GAG AAG AAG TCT        211
Lys Thr Leu Arg Arg Phe Gly Pro Pro Pro Ala Pro Glu Lys Lys Ser
 50                      55                      60

CTT AAT AAA TCT CGA GTA CCA CAG GCG GCT TTG ATA TCC GAA ACT CTA        259
Leu Asn Lys Ser Arg Val Pro Gln Ala Ala Leu Ile Ser Glu Thr Leu
 65                      70                      75                80

CTG ACG AAC GAG CTG TTA GTC ATG ATT AAG ATC GTC GAA GAT GTT TCT        307
Leu Thr Asn Glu Leu Leu Val Met Ile Lys Ile Val Glu Asp Val Ser
                 85                      90                      95

CCT CAT CCT AAC GTC ATT CAT CTC TAC GAC GTT TGT GAG GAT CCT TCT        355
Pro His Pro Asn Val Ile His Leu Tyr Asp Val Cys Glu Asp Pro Ser
                100                     105                     110

GGA GTT CAT CTC ATT TTG GAG CTT TGC TCT GGT GGT GAG CTC TTT GAT        403
Gly Val His Leu Ile Leu Glu Leu Cys Ser Gly Gly Glu Leu Phe Asp
            115                     120                     125

CGG ATT GCT GGG CAA GCA AGG TAT AAT GAG GCT GGG GCT GCT GCT GTG        451
Arg Ile Ala Gly Gln Ala Arg Tyr Asn Glu Ala Gly Ala Ala Ala Val
        130                     135                     140

GTG AGA CAG ATA GCT AAG GGG CTA GAG GCG CTA CAC GGG GCA AGT ATA        499
Val Arg Gln Ile Ala Lys Gly Leu Glu Ala Leu His Gly Ala Ser Ile
145                     150                     155                 160

GTT CAC AGG GAC TTG AAA CCA GAG AAC TGT CTA TTC TTG AAC AAG GAT        547
Val His Arg Asp Leu Lys Pro Glu Asn Cys Leu Phe Leu Asn Lys Asp
                165                     170                     175

GAG AAT TCA CCG TTG AAG ATT ATG GAT TTT GGG CTG AGT TCT ATT GAG        595
Glu Asn Ser Pro Leu Lys Ile Met Asp Phe Gly Leu Ser Ser Ile Glu
            180                     185                     190

GAT TTT GCA AAT CCA GTG GTT GGT TTG TTT GGT TCC ATA GAT TAT GTA        643
Asp Phe Ala Asn Pro Val Val Gly Leu Phe Gly Ser Ile Asp Tyr Val
        195                     200                     205

TCA CCA GAA GCA CTT TCA AGG GAA AAT ATC ACC ACT AAA AGT GAT ATT        691
Ser Pro Glu Ala Leu Ser Arg Glu Asn Ile Thr Thr Lys Ser Asp Ile
    210                     215                     220

TGG TCA CTT GGT GTT ATC CTT TAC ATT CTC CTC TCT GGG TAC CCA CCT        739
Trp Ser Leu Gly Val Ile Leu Tyr Ile Leu Leu Ser Gly Tyr Pro Pro
225                     230                     235                 240

TTC ATC GCG CCG TCC AAT CGA AAA AAG CAA CAA ATG ATA TTA AAT GGG        787
Phe Ile Ala Pro Ser Asn Arg Lys Lys Gln Gln Met Ile Leu Asn Gly
                245                     250                     255

CAG TTC AGT TTT GAT GAG AAA ACC TGG AAA AAC ATA TCT TCA TCG GCA        835
Gln Phe Ser Phe Asp Glu Lys Thr Trp Lys Asn Ile Ser Ser Ser Ala
            260                     265                     270

AAA CAA CTA ATT TCC AGT CTC TTG AAA GTT GAT CCT AAC ATG AGG CCT        883
Lys Gln Leu Ile Ser Ser Leu Leu Lys Val Asp Pro Asn Met Arg Pro
        275                     280                     285

ACT GCT CAA GAG ATA CTT GAA CAT CCA TGG GTG ACA GGA GAT TTG GCA        931
Thr Ala Gln Glu Ile Leu Glu His Pro Trp Val Thr Gly Asp Leu Ala
    290                     295                     300

AAG CAA GAA CAG ATG GAC GCC GAG ATT GTT TCC CGT CTC CAA AGC TTC        979
Lys Gln Glu Gln Met Asp Ala Glu Ile Val Ser Arg Leu Gln Ser Phe
305                     310                     315                 320

AAC TCT CGG CGC AAG TTC AGG GCA GCA GCT ATG GCC AGT GTC TTG AGC       1027
Asn Ser Arg Arg Lys Phe Arg Ala Ala Ala Met Ala Ser Val Leu Ser
                325                     330                     335
```

```
AGC AGC TTT TCC TTG CGA ACT AAG AAA TTG AAG AAA TTG GTT GGT TCA    1075
Ser Ser Phe Ser Leu Arg Thr Lys Lys Leu Lys Lys Leu Val Gly Ser
        340                 345                 350

TAT GAC TTG AAG CCT GAA GAA TTA CAA AAC CTT AGC CAC AAT TTC AAG    1123
Tyr Asp Leu Lys Pro Glu Glu Leu Gln Asn Leu Ser His Asn Phe Lys
            355                 360                 365

AAA ATA TGC AAA AAT GGA GAA AAT TCA ACT TTA CTG GAA TTC GAA GAG    1171
Lys Ile Cys Lys Asn Gly Glu Asn Ser Thr Leu Leu Glu Phe Glu Glu
    370                 375                 380

GTC CTC AAA GCT ATG GAA ATG TCA TCT TTA GTG CCT TTA GCT CCC AGA    1219
Val Leu Lys Ala Met Glu Met Ser Ser Leu Val Pro Leu Ala Pro Arg
385                 390                 395                 400

ATA TTT GAT CTA TTT GAC AAT AAC CGT GAT GGA ACA GTA GAC ATG AGA    1267
Ile Phe Asp Leu Phe Asp Asn Asn Arg Asp Gly Thr Val Asp Met Arg
                405                 410                 415

GAA ATA ATT GGT GGC TTC TCA AGC CTC AAG TAT TCC CAA GGG GAT GAC    1315
Glu Ile Ile Gly Gly Phe Ser Ser Leu Lys Tyr Ser Gln Gly Asp Asp
            420                 425                 430

GCA CTT CGT CTT TGT TTC CAG ATG TAT GAT ACA GAT CGA TCA GGC TGC    1363
Ala Leu Arg Leu Cys Phe Gln Met Tyr Asp Thr Asp Arg Ser Gly Cys
        435                 440                 445

ATT AGC AAG GAA GAA GTT GCG TCC ATG TTG AGA GCA CTT CCT GAA GAC    1411
Ile Ser Lys Glu Glu Val Ala Ser Met Leu Arg Ala Leu Pro Glu Asp
    450                 455                 460

TGC CTT CCA ATT AAT ATA ACA GAA CCA GGA AAA CTT GAC GAG ATA TTT    1459
Cys Leu Pro Ile Asn Ile Thr Glu Pro Gly Lys Leu Asp Glu Ile Phe
465                 470                 475                 480

GAT TTA ATG GAT GCA AAC AGT GAT GGT AAA GTT ACT TTT GAT GAG TTC    1507
Asp Leu Met Asp Ala Asn Ser Asp Gly Lys Val Thr Phe Asp Glu Phe
                485                 490                 495

AAA GCT GCT ATG CAA AGA GAT AGT TCC CTT CAA GAT GTA GTC CTC TCT    1555
Lys Ala Ala Met Gln Arg Asp Ser Ser Leu Gln Asp Val Val Leu Ser
            500                 505                 510

TCT CTT CGT CCC TCT TAA                                            1573
Ser Leu Arg Pro Ser
        515

TTAATTCCTT TATTGAATTT TTGCCTCTTT TAATTTGTAA TAACACGCTA ATTCTATTAA  1633

TATCTCTAAC TTTCTATGAC AATGCATTTA TTATTTTTAT CACTACTCGT AAAAAGATCC  1693

TTTAAATTAA TTCGGAAGCC TTTATGGTAA AAAAAAAAAA AAAAAAAAAA AAAAAAAAAA  1753

AAAAAAAAAA AAAAAAAAAA AAA                                          1776

(2) INFORMATION FOR SEQ ID NO: 11:

(i) SEQUENCE CHARACTERISTICS:
        (A) LENGTH: 1720 base pairs
        (B) TYPE: nucleic acid
        (C) STRANDEDNESS: double stranded
        (D) TOPOLOGY: linear (ii) MOLECULE TYPE: Genomic DNA
        (A) DESCRIPTION: Tobacco CCaMK promoter (xi) SEQUENCE DESCRIPTION: SEQ ID NO:11:

GTCGACCTTC TGCGTTGTTT GGTTTGTAGG AGCACCGGGA GGAACTGGAC CTCGCCTAGT    60

TGCTTTATTG GAAGTACCCG ATATCGCCTG TTTCAGTTCT GTCATTACCG TATCCTGTCG   120

TGTGAGATGG CCTAGAATGG ACTCTTATTG CGCTTGCAGG ACCCTTACCG CTTCGACGAC   180

GTGCTCCTCT TCAGCATCCT TGGGAGTCAC TTCTCGAACA TGTCGGGGGT ATCGCCTTCC   240

ATGGACCGGT GTGGCCTCAT TTCCCCCGCT GCGGGTATCG CTGATCAAAT CCTCATTCTG   300
```

-continued

```
AGGTTAATTT CCTTGGGACT CAAGGTTTTA TGTGTTGTTA ACATCATTAT CTGCCATTTT      360

CTATGATTTT TTGCTTAGAA CAAATAATCA AACACGTTAG AAAGAGACAA GGACCAACTT      420

AATCACACAA CTATCTAAGC CACACGATGG GCGCCAAACT GTTTACCCGT AAAACGGTAC      480

AATTAAATAT ATGTGGTTTA TAGACAAGTG AATTAATTTA ATCCTAAAAT AATAGAAGAA      540

TTAGATAAAA ATGTAATATT TAGCCTTGAG ATTGAGATGA AATAGTAGAA ATAGTAATTC      600

CGGGAGCAAG ACTTCCGGGC ACAACGACAA TGATATCAAA GGACAAGAAG ATAAAATTAT      660

ATTAAACTTT GAATAGAGTG TAATGTATGT TGCTAGAAAA ATTCATGTCC TTCACAATGA      720

TAATAGAGCT CACTATTTAT AGCTCCACCT AAGGAAAGAT CCTAGGATCA AGCCCCTCTT      780

TAATGTCAAT TATGAGGGCC ATTGAAGAAT TTGTAACGTG GCAGTGAATG CCATATTTCT      840

TGTAACGGAC ATATACTTAA TGTTGTAGAA TATTCTTCAT TAGATGCTAC TGGATGACAA      900

ACATTTATTT TATCTTTATG AGTATCATTC TCTTCGGTAA CGGACGGGAT CGTTGCCTTT      960

GGTTTCAACT ATCTTATGTC TTCGGCCACA CATATCATTT CCTCGTGCGA TCATTTAATA     1020

TAACATATTT TAGCCTATAC AATATTATTT TATCTAATTT TTCACGGATA ACATCTTGTA     1080

TTTTCTTTAA TTCAAGTTAA CTTTTAATCA GCTAGATGAT AGAGATTATC ATTTTATTCA     1140

TGGAAAGCTT GTTATTCATA AGTTATAAAA TAGCTTATAT AGCAAATCTT TACTTGTGAT     1200

TTAGTATATA TATGAACTAA AGACTACAAA GAAATCTTGT GAGCCCCTCG CTAAAGAGGA     1260

TGATGATGGA GGAAACGAGT ACACTTGATC GATTATGAAA GAAACCATCC TTAAAAAAAC     1320

CAAATTAAGA CCAAACAGTA AAGGTAAATT ATGCGTAGAA AGCAAGAAAT TTGTACTTGC     1380

CTATCTACAT GATTGGAGGC ATCTTATAAT AATCTTATTG AGAGAGATGC ATCTCAAGAA     1440

CAAAGAGAAT TAACATAATT AATCTGAAAG AAGATTAGTT TGACTAAGTC AATTGTATAT     1500

TATTATTAGC CTTCTTCCCC TTTGTTGCCA TTTGCTTATA TTTCATGGCC CACACCAACC     1560

CGCCCGGCCA ACAAAAATTA TAAATTAAAA ACCCTTTTAA AACTCATGAT CATCAGTTTG     1620

ATGATGTAAC TACGTGTATA CCCACCTCAA TAATACTGTA CCTCATTTCC TTATTAATTC     1680

CATCCTAATA TTCGTCAAAC ACAATTAACC TTTCTCTCTC                           1720
```

(2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide
        (A) DESCRIPTION: Highly conserved region of mammalian
            calcium/calmodulin-dependent protein kinases (xi) SEQUENCE DESCRIPTION: SEQ ID NO:12:

Asp Leu Lys Pro Glu Asn
            5

(2) INFORMATION FOR SEQ ID NO: 13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide
        (A) DESCRIPTION: Highly conserved region of mammalian
            calcium/calmodulin-dependent protein kinases (xi) SEQUENCE DESCRIPTION: SEQ ID NO:13:

```
Phe Asn Ala Arg Arg Lys Leu
            5
```

(2) INFORMATION FOR SEQ ID NO: 14:

(i) SEQUENCE CHARACTERISTICS:
        (A) LENGTH:  12 amino acids
        (B) TYPE:  amino acid
        (D) TOPOLOGY:  linear (ii) MOLECULE TYPE:  peptide
        (A) DESCRIPTION:  GS peptide (xi) SEQUENCE DESCRIPTION:  SEQ ID NO:14:

```
Pro Leu Ser Arg Thr Leu Ser Val Ala Ala Lys Lys
            5                   10
```

(2) INFORMATION FOR SEQ ID NO: 15:

(i) SEQUENCE CHARACTERISTICS:
        (A) LENGTH:  11 amino acids
        (B) TYPE:  amino acid
        (D) TOPOLOGY:  linear (ii) MOLECULE TYPE:  Peptide
        (A) DESCRIPTION:  MBP peptide (xi) SEQUENCE DESCRIPTION:  SEQ ID NO:15:

```
Gln Lys Arg Pro Ser Gln Arg Ser Lys Tyr Leu
            5                   10
```

(2) INFORMATION FOR SEQ ID NO: 16:

(i) SEQUENCE CHARACTERISTICS:
        (A) LENGTH:  19 base pairs
        (B) TYPE:  nucleic acid
        (C) STRANDEDNESS:  single stranded
        (D) TOPOLOGY: linear (ii) MOLECULE TYPE:  Other nucleic acid
        (A) DESCRIPTION:  Oligonucleotide primer for site-directed
            mutagenesis to accomplish EF-hand I mutation (xi) SEQUENCE DESCRIPTION:  SEQ ID NO:16:

CTCTCATGGC TATAGTTCC                                          19

(2) INFORMATION FOR SEQ ID NO: 17:

(i) SEQUENCE CHARACTERISTICS:
        (A) LENGTH:  19 base pairs
        (B) TYPE:  nucleic acid
        (C) STRANDEDNESS:  single stranded
        (D) TOPOLOGY: linear (ii) MOLECULE TYPE:  Other nucleic acid
        (A) DESCRIPTION:  Oligonucleotide primer for site-directed
            mutagenesis to accomplish EF-hand II mutation (xi) SEQUENCE DESCRIPTION:  SEQ ID NO:17:

CCTCCTTGGC GATACATCC                                          19

(2) INFORMATION FOR SEQ ID NO: 18:

(i) SEQUENCE CHARACTERISTICS:
        (A) LENGTH:  18 base pairs
        (B) TYPE:  nucleic acid
        (C) STRANDEDNESS:  single stranded
        (D) TOPOLOGY: linear -continued

```
   (ii) MOLECULE TYPE:  Other nucleic acid
        (A) DESCRIPTION:  Oligonucleotide primer for site-directed
             mutagenesis to accomplish EF-hand III mutation (xi) SEQUENCE DESCRIPTION:  SEQ ID NO:18:

GTCGAACGCG ACAACTCC                                                   18

(2) INFORMATION FOR SEQ ID NO: 19:

(i) SEQUENCE CHARACTERISTICS:
         (A) LENGTH:  21 base pairs
         (B) TYPE:  nucleic acid
         (C) STRANDEDNESS:  single stranded
         (D) TOPOLOGY:  linear (ii) MOLECULE TYPE:  other nucleic acid
        (A) DESCRIPTION:  Oligonucleotide primer for site-directed
             mutagenesis to create an NdeI site at
             amino acid residue 358 (Met) of SEQ ID NO:1

(xi) SEQUENCE DESCRIPTION:  SEQ ID NO:19:

GGATCCCATC ATATGAAATC G                                               21
```